US010195455B2

(12) United States Patent
Stubbeman

(10) Patent No.: US 10,195,455 B2
(45) Date of Patent: Feb. 5, 2019

(54) METHOD AND SYSTEM FOR THERAPEUTIC BRAIN STIMULATION USING ELECTROMAGNETIC PULSES

(71) Applicant: William F. Stubbeman, Los Angeles, CA (US)

(72) Inventor: William F. Stubbeman, Los Angeles, CA (US)

(73) Assignee: William F. Stubbeman, Los Angeles, CA (US)

( * ) Notice: Subject to any disclaimer, the term of this patent is extended or adjusted under 35 U.S.C. 154(b) by 443 days.

(21) Appl. No.: 14/675,111

(22) Filed: Mar. 31, 2015

(65) Prior Publication Data

US 2016/0008620 A1 Jan. 14, 2016

Related U.S. Application Data

(60) Provisional application No. 61/973,827, filed on Apr. 1, 2014.

(51) Int. Cl.
*A61N 2/00* (2006.01)
*A61N 1/36* (2006.01)
(Continued)

(52) U.S. Cl.
CPC ............ *A61N 2/006* (2013.01); *A61B 5/4848* (2013.01); *A61N 1/36082* (2013.01);
(Continued)

(58) Field of Classification Search
CPC ...... A61N 2/004; A61N 2/02; A61N 1/36082; A61N 1/36021; A61N 1/36025;
(Continued)

(56) References Cited

U.S. PATENT DOCUMENTS 7,024,247 B2 * 4/2006 Gliner .................. A61N 1/0531
607/48
7,236,830 B2 * 6/2007 Gliner ................ A61N 1/36082
607/45

(Continued)

FOREIGN PATENT DOCUMENTS

WO 2013172981 A1 11/2013

OTHER PUBLICATIONS

Paulus et al.; Lasting influence of repetitive transcranial magnetic stimulation on intracortical excitability in human subjects; Neuroscience Letters 287 (2000) 37-40.*

(Continued)

*Primary Examiner* — Navin Natnithithadha
*Assistant Examiner* — Sunita Reddy
(74) *Attorney, Agent, or Firm* — Ben J. Yorks; Irell and Manella, LLP

(57) ABSTRACT

A therapeutic or diagnostic system comprises a non-invasive brain stimulation device (such as a TMS stimulation device) or other neuromodulation device configured to stimulate a patient's brain or nervous system by emitting electromagnetic pulses according to stimulation parameters, such as a pulse frequency or burst repetition frequency or other parameters, that provides surprising improvements in responsiveness and/or may require only a relatively short train of pulses to achieve high efficacy. In particular, stimulation pulses may be delivered at a frequency of between 12 and 40 Hertz with a 3 to 5 ratio as compared with burst repetition frequency, or at other specific patterns within that range. The stimulation parameters may be pre-stored and customized to individual patients, being identified through an automated search routine during which patient feedback is monitored. A user interface may be provided to allow an (Continued)

operator to conveniently select the appropriate parameters for the desired treatment.

16 Claims, 43 Drawing Sheets

(51) Int. Cl.
*A61B 5/00* (2006.01)
*A61B 5/04* (2006.01)
*A61B 5/0476* (2006.01)

(52) U.S. Cl.
CPC ............ *A61N 2/004* (2013.01); *A61B 5/0059* (2013.01); *A61B 5/04008* (2013.01); *A61B 5/0476* (2013.01); *A61B 5/4094* (2013.01); *A61N 1/36021* (2013.01); *A61N 1/36025* (2013.01)

(58) Field of Classification Search
CPC .. A61N 2/006; A61B 5/0059; A61B 5/04008; A61B 5/0476; A61B 5/4848; A61B 5/4094
USPC .......................................... 600/9, 14; 607/45
See application file for complete search history.

(56) References Cited

U.S. PATENT DOCUMENTS

| | | |
|---|---|---|
| 2010/0256438 A1 | 10/2010 | Mishelevich |
| 2012/0197163 A1 | 8/2012 | Mishelevich |
| 2013/0281890 A1 | 10/2013 | Mishelevich |
| 2014/0031605 A1 | 1/2014 | Schneider |
| 2014/0058189 A1 | 2/2014 | Stubbeman |

OTHER PUBLICATIONS

Schindler et al.;Theta burst transcranial magnetic stimulation is associated with increased EEG synchronization in the stimulated relative to unstimulated cerebral hemisphere; Neuroscience Letters 436 (2008) 31-34.*

Maeda et al.; Interindividual variability of the modulatory effects of repetitive transcranial magnetic stimulation on cortical excitability; Exp Brain Res (2000) 133:425-430.*

Written Opinion of the International Searching Authority, dated Oct. 8, 2015.

International Search Report, dated Jul. 24, 2015.

Chistyakov, A., et al., "Safety, tolerability and preliminary evidence for antidepressant efficacy of theta-burst transcranial magnetic stimulation in patients with major depression," International Journal of Neuropsychopharmacology, (2010) 13(3), 387-393.

Cho, S. S., et al., "Continuous theta burst stimulation of right dorsolateral prefrontal cortex induces changes in impulsivity level," Brain stimulation, (2010) 3(3), 170-176.

De Ridder, D., et al., "Theta, alpha and beta burst transcranial magnetic stimulation: brain modulation in tinnitus," International journal of medical sciences, (2007) 4(5), 237.

George, M. S., et al., "Daily left prefrontal transcranial magnetic stimulation therapy for major depressive disorder: a sham-controlled randomized trial," Archives of general psychiatry, (2010) 67(5), 507-516.

Holzer, M., et al., "Intermittent theta burst stimulation (iTBS) ameliorates therapy-resistant depression: a case series," Brain stimulation, (2010) 3(3), 181-183.

Huang, Y. Z., et al., "Theta burst stimulation of the human motor cortex," Neuron, (2005) 45(2), 201-206.

O'Reardon, et al., "Efficacy and safety of transcranial magnetic stimulation in the acute treatment of major depression: a multisite randomized controlled trial," (2007) Biological psychiatry, 62(11), 1208-1216.

Speer, Andrew M. et al., Antidepressant Efficacy of High and Low Frequency rTMS at 110% of Motor Threshold versus Sham Stimulation over Left Prefrontal Cortex, Brain Stimulation 7 (2014) 36-41, www.brainstimjrnl.com Aug. 6, 2013.

Stern, William M. Stern, Antidepressant Effects of High and Low Frequency Repetitive Transcranial Magnetic Stimulation to the Dorsolateral Prefrontal Cortex: A Double-Blind, Randomized, Placebo-Controlled Trial, J Neuropsychiatry Clin Neurosci 19:179-186, Spring 2007, American Psychiatric Publishing, Inc. Dec. 13, 2000.

Fitzgerald, Paul B., A randomized trial of low-frequency right-prefrontal-cortex transcranial magnetic stimulation as augmentation in treatment-resistant major depression; International Journal of Neuropsychopharmacology (2006), 9, 655-666 Sep. 7, 2006.

Nahas, Ziad et al., Left prefrontal transcranial magnetic stimulation (TMS) treatment of depression in bipolar affective disorder: a pilot study of acute safety and efficacy, Bipolar Disorders 2003: 5: 40-47 Oct. 29, 2002.

Padberg, Frank, M.D. et al, Repetitive Transcranial Magnetic Stimulation (rTMS) in Major Depression; Relation between Efficacy and Stimulation Intensity, Neuropsychopharmacology 2002, vol. 27, No. 4 Mar. 25, 2002.

Avery, David H. et al., A Controlled Study of Repetitive Transcranial Magnetic Stimulation in Medication-Resistant Major Depression, Biol Psychiatry 2006; 59:187-194 Jun. 21, 2005.

Loo, Colleen K. et al., A sham-controlled trial of the efficacy and safety of twice-daily rTMS in major depression, Psychological Medicine, 2007, 37, 341-349 Dec. 19, 2006.

Eranti, Savitha, M.D, et al., A Randomized, Controlled Trial With 6-Month Follow-Up of Repetitive Transcranial Therapy for Severe Depression, Am J Psyschiatry 164:1, Jan. 2007 Jan. 2007.

O'Reardon, John P. et al., Efficacy and Safety of Transcranial Megnetic Stiumulation in the Acute Treatment of Major Depression: A Multisite Randomized Controlled Trial, Biol Psychiatry 2007; 62:1208-1216 Jan. 19, 2007.

Mogg, A. et al, A randomized controlled trial with 4-month follow-up adjunctive repetitive transcranial magnetic stimulation of the left prefrontal cortex for depression, Psychological Medicine (2008) 38, 323-333 Oct. 15, 2007.

Holtzheimer, Paui E, III, M.D. et al., Accelerated Repetitive Transcranial Magnetic Stimulation for Treatment-Resistant Depression, Depression and Anxiety, 27:960-963 (2010) Jun. 24, 2010.

Blumberger, Daniel M., A randomized double-blind sham-controlled comparison of unilateral and bilateral repetitive transcranial magnetic stimulation for treatment-resistant major depression, The World Journal of Biological Psychiatry, 2012; 13: 423-435 Mar. 29, 2011.

George, Mark S. et al., Daily Left Prefrontal Transcranial Magnetic Stimulation Therapy for Major Depressive Disorder, (Reprinted) Arch. Gen Psychiatry, vol. 67, (No. 5), May 2010 May 3, 2010.

Rossini, David, Transcranial magnetic stimulation in treatment-resistant depressed patients: A double-blind, placebo-controlled trial, Psychiatry Research 137 (2005) 1-10 Jun. 13, 2005.

George, Mark S., M.D. et al., Mood improvement Following Daily Left Prefrontal Repetitive Transcranial Magnetic Stimulation in Patients With Depression: A Placebo-Controlled Crossover Trial, Am J Psychiatry Dec. 1997; 154:1752-1756 Dec. 1997.

Bakim, Bahadir et al., The Combination of Antidepressant Drug Therapy and High-Frequency Repetitive Transcranial Magnetic Stimulation in Medication-Resistant Depression, Bulletin of Clinical Psychopharmocology, vol. 22, N.:3, 2012 Aug. 7, 2012.

Fitzgerald, Paul B. et al., A Randomized, Controlled Trial of Sequential Bilateral Repetitive Transcranial Magnetic Stimulation for Treatment-Resistant Depression, Am J Psychiatry 2006; 163:88-94 Jan. 2006.

Plewnia, Christian et al., Treatment of major depression with bilateral theta burst stimulation; A randomized controlled pilot trial, Journal of Affective Disorders 156 (2014) 219-223 Dec. 28, 2013.

\* cited by examiner

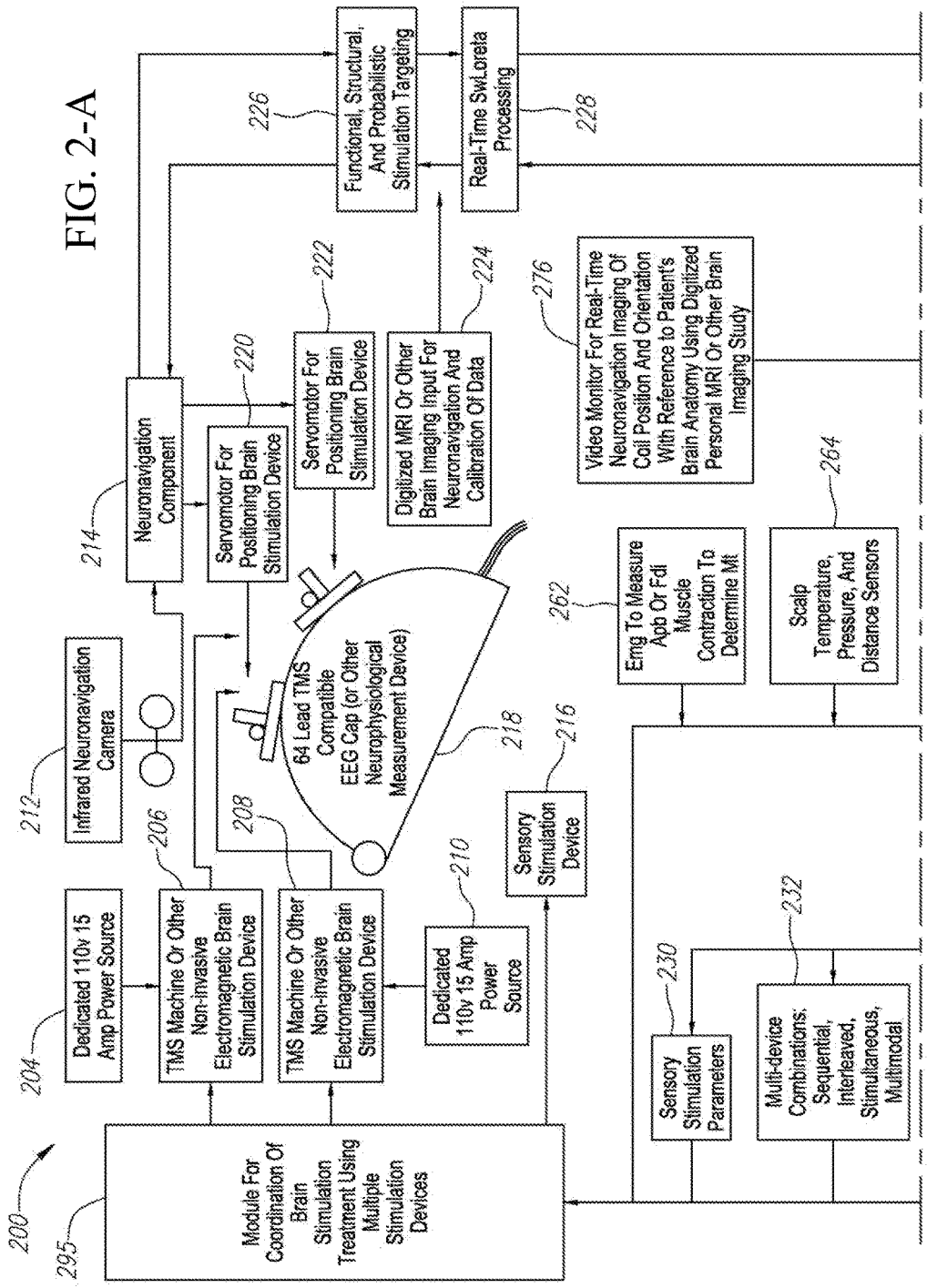
FIG. 2-A

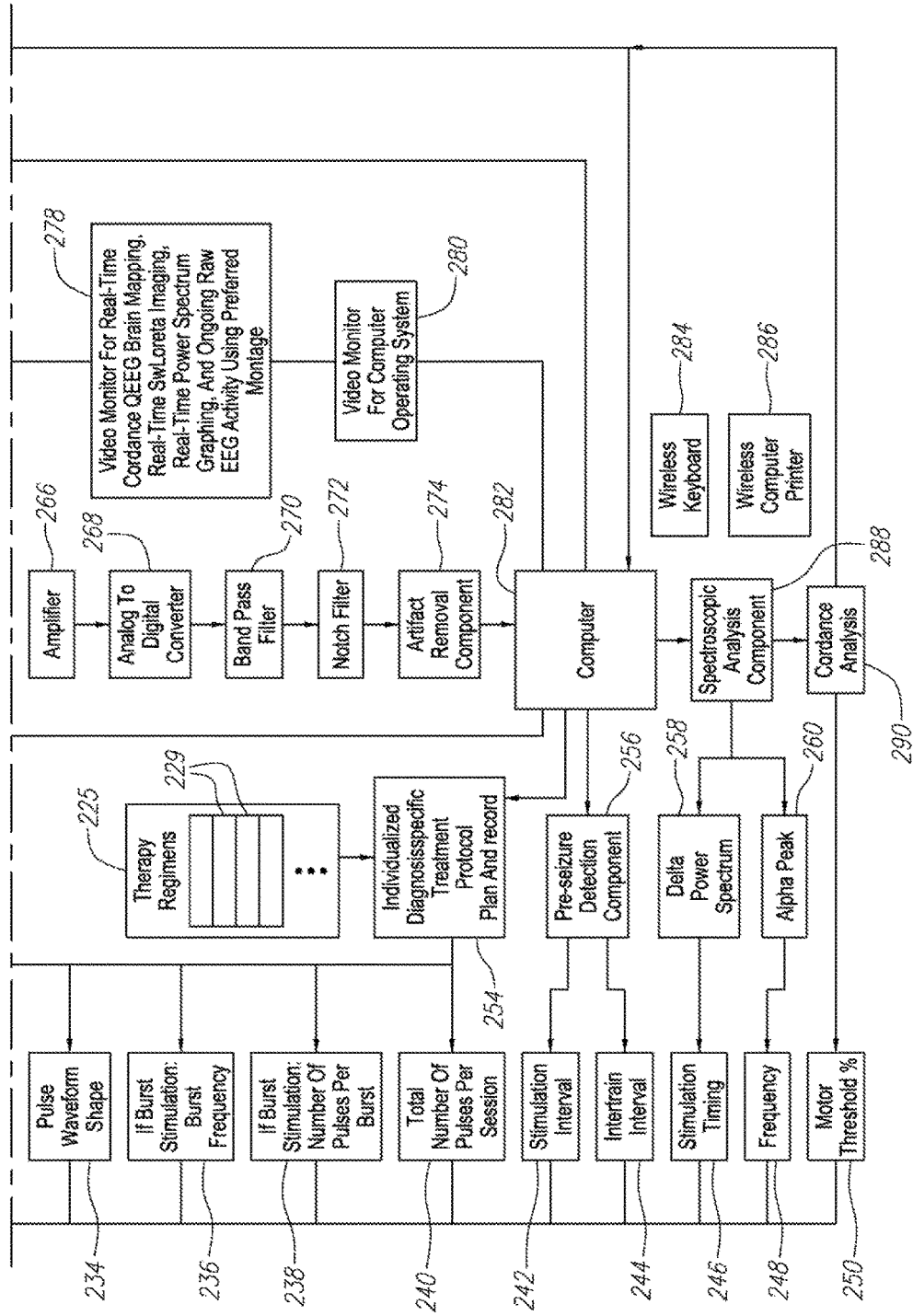
FIG. 2-B

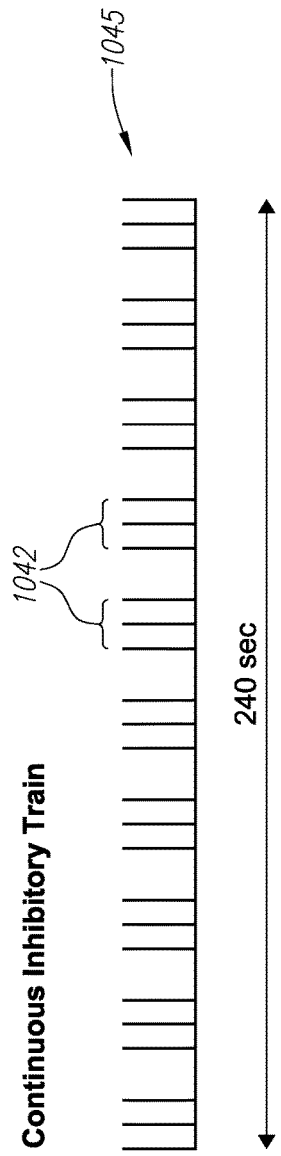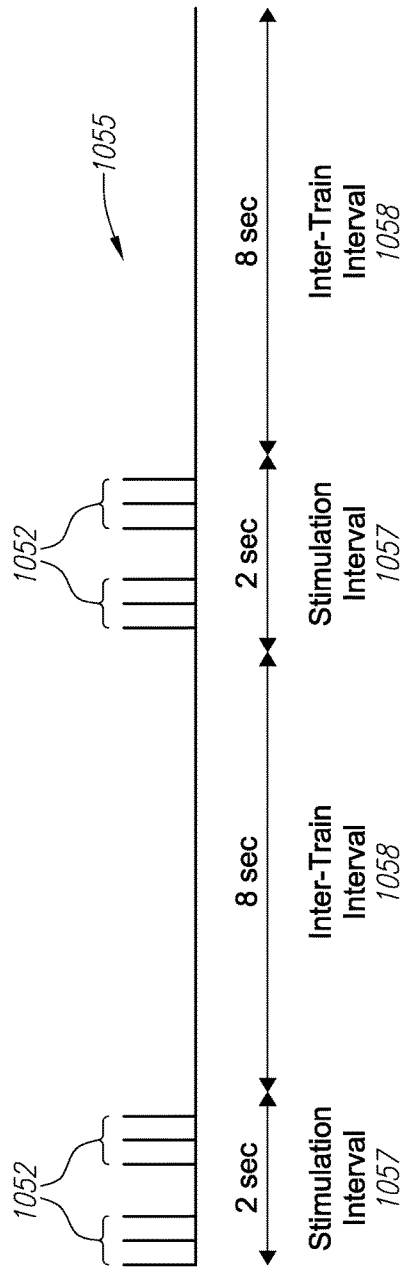

| Figure 2. Sequence of TBS Treatment Parameters ||||| 
|---|---|---|---|---|
| Patient | LDLPFC TBS 50Hz | Bilateral Sequential TBS 50Hz | LDLPFC TBS 20Hz | Bilateral Sequential TBS 20Hz |
| 1 | →  | → | → | → |
| 2 |  | → | → | → |
| 3 |  |  | → | → |
| 4 |  |  | → |  |

Sequence of treatment algorithm from left to right. Patients initially presenting with severe anxiety symptoms began treatment with Bilateral Sequential TBS 50Hz while patients initially presenting without severe anxiety symptoms began with LDLPFC TBS 50 Hz. Patients were advanced through the algorithm after not improving for two consecutive weeks, or reaching a BDI II Rating Scale Score of < 10.

FIG. 11

| Treatment Days Spent by Each Patient in Each Protocol |||||| 
|---|---|---|---|---|---|
| Patient ID | Unilateral | Bilateral | Unilateral | Bilateral | Total |
| Patient (Number) | Tx Days | Tx Days | Tx Days | Tx Days | Tx Days |
| 1 | 16 | 4 | 36 | 11 | 67 |
| 2 | 47 | 27 | 17 |  | 91 |
| 3 |  | 18 | 73 | 12 | 103 |
| 4 |  | 41 | 10 |  | 51 |
| Mean | 31.5 | 22.5 | 34.0 | 11.5 | 78.0 |
| SD | 21.9 | 15.5 | 28.2 | 0.7 | 23.4 |
| ANOVA p value: 0.644 |||||| 
| Conclusion: Number of treatment days in each protocol is not significantly different ||||||

Table 1. Demographics/Clinical Characteristics

| Patient | Age | Gender | Handedness | Diagnosis and Comorbid Diagnosis (DSM-IV) | Duration of Illness (Years) | Total Number of Failed Psychiatric Medications | Duration of Current Episode (Years) | Psychiatric Medication Taken Concurrently with TBS Treatment* | BDI II Rating Scale Scores | | |
|---|---|---|---|---|---|---|---|---|---|---|---|
| | | | | | | | | | Baseline | Final | Absolute Difference | % Difference |
| 1 | 62 | M | Right | Major Depressive Disorder, Recurrent, Severe without Psychotic Features | 7 | 10 | 7 | LIOTHYRONINE SODIUM<br><br>LAMOTRIGINE MELATONIN NEFAZODONE FLUOXETINE QUETIAPINE ZALEPLON TEMAZEPAM | 33 | 6 | 27 | 81.8 |
| 2 | 23 | M | Right | Major Depressive Disorder, Recurrent, Severe without Psychotic Features<br><br>Social Phobia<br><br>Cocaine Dependence, In Remission<br><br>Opiod Type Dependence, In Remission | 5 | 14 | 5 | ARIPIPRAZOLE<br><br>ZOLPIDEM DIVALPROEX SODIUM RISPERIDONE<br><br>LISDEXAMFETAMINE DIMESYLATE | 36 | 6 | 30 | 83.3 |

| | | | | | | | | |
|---|---|---|---|---|---|---|---|---|
| 3 | 22 | M | Right | Major Depressive Disorder, Recurrent, Severe without Psychotic Features Generalized Anxiety Disorder Combinations of Drug Dependence Excluding Opioid Type Drug, Unspecified | 10 | 8 | 4 | LAMOTRIGINE | 38 | 8 | 32 | 78.9 |
| 4 | 54 | M | Right | Major Depressive Disorder, Recurrent, Severe without Psychotic Features | 30 | 9 | 30 | ARIPIPRAZOLE PROPRNLOL LAMOTRIGINE | 26 | 6 | 20 | 75.9 |
| MEAN: | 42.8 | | | | 13.0 | 10.3 | 11.5 | | 33.3 | 6.5 | 27.3 | 80.3 |
| SD: | 23.4 | | | | 11.5 | 2.6 | 12.4 | | 5.3 | 1.0 | 5.3 | 2.9 |

*Patient 1 had a gap of seven months between Bilateral Sequential TBS 50Hz and LDLPFC TBS 20Hz phases of treatment due to the fact that TBS 20Hz was not available; patient 1 tapered off lamictal and Prozac in the weeks leading to TBS 20Hz treatment, then restarted both at the same doses in the first two weeks of TBS 20Hz treatment. Seroquel was added for insomnia by his primary psychiatrist during TBS 20Hz treatment.
Patient 4 tapered off Lamictal in the weeks leading to TBS 50Hz treatment, then restarted Lamictal in the first two weeks at the same dose.

FIG. 13-B

| Protocol | Stimulation Site | Pulse # | % MT | Pulses/Burst | Burst Hz | Pulse Hz | SI (s) | ITI (s) | Music | Ear Plugs |
|---|---|---|---|---|---|---|---|---|---|---|
| L TBS 50 Hz | 1. LDLPFC | 4950 | 90% | 3 | 5 | 50 | 2 | 8 | X | |
| B TBS 50 Hz | 1. RDLPFC | 3600 | 90% | 3 | 5 | 50 | 239 | 0 | | X |
| | 2. LDLPFC | 4950 | 90% | 3 | 5 | 50 | 2 | 8 | X | |
| L TBS 20 Hz | 1. LDLPFC | 4950 | 90% | 3 | 5 | 20 | 239 | 0 | X | |
| B TBS 20 Hz | 1. RDLPFC | 3600 | 90% | 3 | 5 | 20 | 239 | 0 | | X |
| | 2. LDLPFC | 4950 | 90% | 3 | 5 | 20 | 2 | 8 | X | |

FIG. 14

Initial and Final BDI Scale Scores for Each Protocol Transition

| Patient (Number) | Unilateral Theta 50 | | Bilateral Theta 50 | | Unilateral Theta 20 | | Bilateral Theta 20 | | Overall Decrease | | Followup |
|---|---|---|---|---|---|---|---|---|---|---|---|
| | Initial | Final | Initial | Final | Initial | Final | Initial | Final | Initial | Final | |
| 1 | 33 | 18 | 18 | 17 | 44 | 23 | 23 | 7 | 33 | 6 | 9 |
| 2 | 36 | 16 | 16 | 15 | 15 | 6 | | | 36 | 6 | 5 |
| 3 | | | 38 | 31 | 31 | 12 | 12 | 8 | 38 | 8 | 8 |
| 4 | | | 26 | 14 | 14 | 6 | | | 26 | 6 | 9 |

Average Normalized Parameter MEP Amplitude Change

| | 1 | 4 | 5 | 6 | 7 | 20 |
|---|---|---|---|---|---|---|
| Overall Average Ratio 3 pulses | | | | | | |
| 1 | -0.1 | | | | | |
| 6 | | | 0.11 | | | |
| 10 | | | | | | |
| 16 | | -0.09 | 0.6 | | | |
| 18 | | | 0.02 | | | |
| 20 | | -0.14 | -0.5 | -0.59 | | -0.37 |
| 22 | | | -0.26 | | | |
| 24 | | | 0.07 | -0.26 | | |
| 28 | | | 0.26 | | | |
| 30 | | | | 0.31 | | |
| 50 | | | -0.09 | | | |
| Overall Average Ratio 2 pulses | | | | | | |
| 20 | | | -0.18 | | | |
| 22 | | | -0.35 | | | |
| 24 | | 0.16 | 0.87 | 0.65 | | |
| 25 | | | -0.18 | | | |
| 28 | | | | | -0.42 | |
| Average MEP Change 4+ pulses | | | | | | |
| 25 Hz/4 pulses | | | -0.08 | | | |
| 30 Hz/5 pulses | | | 0.07 | | | |
| Average MEP Change With Triple Pulsed Bursts | | | | | | |
| TBS 20 Hz with 1 Burst | | | 4% | | | |
| TBS 20 Hz with 2 Bursts | | | -27% | | | |
| TBS 20 Hz with 4 Bursts | | | -50% | | | |
| TBS 20 Hz with 10 Bursts | | | 23% | | | |
| TBS 20 Hz with 13 Bursts | | | 14% | | | |

| Parameter Decreases MEP |
|---|
| Parameter Increases MEP |

- 2013: Overall Average Ratio 3 pulses
- 2015: Overall Average Ratio 2 pulses
- 2018: Average MEP Change 4+ pulses
- 2020: Average MEP Change With Triple Pulsed Bursts

FIG. 20B

Corresponding Parameter p-value

| | 1 | 4 | 5 | 6 | 7 | 20 |
|---|---|---|---|---|---|---|
| Overall Average Ratio 3 pulses | | | | | | |
| 1 | 0.490 | | | | | |
| 6 | | | 0.700 | | | |
| 10 | | | | | | |
| 16 | | 0.590 | 0.040 | | | |
| 18 | | | 0.920 | | | |
| 20 | | 0.320 | 0.020 | 0.00003 | | 0.002 |
| 22 | | | 0.063 | | | |
| 24 | | | 0.716 | 0.090 | | |
| 28 | | | 0.460 | 0.253 | | |
| 30 | | | | | | |
| 50 | | | 0.870 | | | |
| Overall Average Ratio 2 pulses | | | | | | |
| 20 | | | 0.230 | | | |
| 22 | | | 0.018 | | | |
| 24 | | 0.457 | 0.010 | 0.028 | | |
| 25 | | | 0.330 | | | |
| 28 | | | | | 0.001 | |
| Average MEP Change 4+ pulses | | | | | | |
| 25 Hz/4 pulses | | | 0.725 | | | |
| 30 Hz/5 pulses | | | 0.740 | | | |
| Average MEP Change With Triple Pulsed Bursts | | | | | | |
| TBS 20 Hz with 1 Burst | | | NS | | | |
| TBS 20 Hz with 2 Bursts | | | NS | | | |
| TBS 20 Hz with 4 Bursts | | | NS | | | |
| TBS 20 Hz with 10 Bursts | | | NS | | | |
| TBS 20 Hz with 13 Bursts | | | NS | | | |

| Statistically Significant $p < .05$ |
|---|
| Not Significant (NS) |

- 2033: Overall Average Ratio 3 pulses
- 2035: Overall Average Ratio 2 pulses
- 2038: Average MEP Change 4+ pulses
- 2040: Average MEP Change With Triple Pulsed Bursts

|  | TBS 20 Hz 5/20/3/12 | TBS 50 Hz 5/50/3/12 |
|---|---|---|
| 0 | 718.1 | 591.3 |
| 5 | 442.4 | 382.5 |
| 10 | 415.2 | 442.1 |
| 15 | 148.2 | 706.3 |
| 20 | 160.2 | 558.8 |
| 25 | 453.6 | 583.0 |
| 30 | 555.4 | 546.5 |
| Average | 362.5 | 536.5 |
| Standard Dev | 168.2 | 113.3 |
| p value | 0.083 | |

*FIG. 26B*

|  | TBS 20 Hz 5/20/3/12 | TBS 50 Hz 5/50/3/12 |
|---|---|---|
| 0 | 100.0% | 100.0% |
| 5 | 61.6% | 64.7% |
| 10 | 57.8% | 74.8% |
| 15 | 20.6% | 119.4% |
| 20 | 22.3% | 94.5% |
| 25 | 63.2% | 98.6% |
| 30 | 77.3% | 92.4% |
| Average | 50.5% | 90.7% |
| Standard Dev | 23.4% | 19.2% |
| p value | 0.011 | |

*FIG. 26C*

|  | TBS 20 Hz 5/20/3/12 | TBS 50 Hz 5/50/3/12 |
|---|---|---|
| 0 | 0.0% | 0.0% |
| 5 | -38.4% | -35.3% |
| 10 | -42.2% | -25.2% |
| 15 | -79.4% | 19.4% |
| 20 | -77.7% | -5.5% |
| 25 | -36.8% | -1.4% |
| 30 | -22.7% | -7.6% |
| Average | -49.5% | -9.3% |
| Standard Dev | 23.4% | 19.2% |
| p value | 0.011 | |

*FIG. 26D*

| Protocol | TBS 20 x 3 | TBS 20 x 6 | TBS 20 x 12 | TBS 20 x 30 | TBS 20 x 39 |
|---|---|---|---|---|---|
| 0 | 0.0% | 0.0% | 0.0% | 0.0% | 0.0% |
| 5 | 7.2% | -27.3% | -38.4% | -9.2% | 6.9% |
| 10 | -38.8% | -49.3% | -42.2% | 8.1% | 49.3% |
| 15 | 17.3% | -30.9% | -79.4% | 28.7% | 29.8% |
| 20 | 34.1% | 2.2% | -77.7% | 55.8% | -28.6% |
| 25 | 27.7% | -23.3% | -36.8% | 31.4% | 5.9% |
| 30 | -26.0% | -30.1% | -22.7% | 23.3% | 18.1% |

Table 1. Demographics/Clinical Characteristics

| Patient | Age | Gender | Handedness | Diagnosis and Comorbid Diagnoses (DSM-IV) | Duration of Illness (Years) | Total Number of Failed Psychiatric Medications | Duration of Current Episode (Years) | Psychiatric Medications Taken Concurrently with Theta Burst Treatment* |
|---|---|---|---|---|---|---|---|---|
| 1 | 62 | M | Right | Major Depressive Disorder | 7 | 10 | 7 | Liothyronine Sodium, Lamotrigine, Melatonin, Nefazodone, Fluoxetine, Quetiapine, Zaleplon, Temazepam |
| 2 | 23 | M | Right | Major Depressive Disorder Social Phobia; Cocaine Dependence, in Remission; Opioid Dependence, in Remission | 5 | 14 | 5 | Aripiprazole, Zolpidem, Divalproex Sodium, Risperidone, Lisdexamfetamine Dimesylate |
| 3 | 22 | M | Right | Major Depressive Disorder, Generalized Anxiety Disorder; Polysubstance Abuse in Remission | 10 | 8 | 4 | Lamotrigine |
| 4 | 64 | M | Right | Major Depressive Disorder | 30 | 9 | 30 | Aripiprazole, Propranolol, Lamotrigine |
| 5 | 83 | M | Right | Major Depressive Disorder, Obsessive Compulsive Disorder | 50 | 10 | 3 | Zolpidem, Lamotrigine, Zaleplon, Sertraline |
| 6 | 46 | M | Right | Major Depressive Disorder | 20 | 20 | 0.5 | Sertraline, Bupropion Hydrochloride, Vortioxetine, Temazepam Clonazepam |
| 7 | 47 | M | Right | Major Depressive Disorder, Obsessive Compulsive Disorder, Alcohol Dependence in Remission | 8 | 4 | 5 | Paroxetine, Ziprasidone, Divalproex Sodium, Gabapentin |
| 8 | 56 | F | Right | Major Depressive Disorder | 24 | 6 | 6 | Fluoxetine |
| 9 | 83 | F | Right | Major Depressive Disorder | 38 | 40 | 38 | Lorazepam, Paroxetine, Levothyroxine |
| 10 | 36 | M | Right | Major Depressive Disorder, Obsessive Compulsive Disorder, Alcohol Dependence in Remission | 18 | 10 | 18 | Escitalopram, Trazodone, Disulfiram, Lorazepam |
| Mean | 52.2 | | | | 21.0 | 13.1 | 11.7 | |
| SD: | 21.7 | | | | 14.8 | 10.4 | 12.8 | |

Theta Burst Treatment Sequence

| Patient | Unilateral TBS 50 Hz | Bilateral TBS 50 Hz | Unilateral TBS 20 Hz | Bilateral TBS 20 Hz | Final Outcome |
|---|---|---|---|---|---|
| 1 | →———|———//———|———→ | | Remission |
| 2 | →———|———→ | | | Remission |
| 3 | | →———|———→ | | Remission |
| 4 | | →———→ | | | Remission |
| 5 | | | →———→ | | Non-remission |
| 6 | | | →———→ | | Remission |
| 7 | | | | →  | Remission |
| 8 | | | | →  | Remission |
| 9 | | | | →  | Remission |
| 10 | | ←······|——— | | Remission |

*FIG. 33*

Table 2: Protocol Parameters

| Protocol | Stimulation Site | Number of Pulses | Motor Threshold | Pulse Frequency (Hz) | Pulses/ Burst | Burst Frequency (Hz) | Stimulation Interval (Sec) | Intertrain Interval (Sec) | Emotionally Uplifting Music | Earplugs |
|---|---|---|---|---|---|---|---|---|---|---|
| Left Theta Burst 50 Hz | 1. LDLPFC | 4950 | 90% | 50 | 3 | 5 | 2 | 8 | x | |
| Bilateral Theta Burst 50 Hz | 1. RDLPFC | 3600 | 90% | 50 | 3 | 5 | 239 | 0 | | x |
| | 2. LDLPFC | 4950 | 90% | 50 | 3 | 5 | 2 | 8 | x | |
| Left Theta Burst 20 Hz | 1. LDLPFC | 4950 | 90% | 20 | 3 | 5 | 2 | 8 | x | |
| Bilateral Theta Burst 20 Hz | 1. RDLPFC | 3600 | 90% | 20 | 3 | 5 | 239 | 0 | | x |
| | 2. LDLPFC | 4950 | 90% | 20 | 3 | 5 | 2 | 8 | x | |

*FIG. 35*

Treatment Days Spent by Each Patient in Each Protocol

| Patient ID | Unilateral TBS 50Hz | Bilateral TBS 50Hz | Total TBS 50Hz | Unilateral TBS 20Hz | Bilateral TBS 20Hz | Total TBS 20Hz | Total TBS (50Hz and 20Hz) |
|---|---|---|---|---|---|---|---|
| Patient (Number) | Treatment Days | Treatment Days | Treatment Days | Treatment Days | Treatment Days | Treatment Days | Treatment Days |
| 1 | 16 | 4 | 20 | 36 | 11 | 47 | 67 |
| 2 | 47 | 27 | 74 | 17 | | 17 | 91 |
| 3 | | 18 | 18 | 73 | 12 | 85 | 103 |
| 4 | | 41 | 41 | 10 | | 10 | 51 |
| 5 | | | | 20 | 35 | 55 | 55 |
| 6 | | | | 15 | 46 | 61 | 61 |
| 7 | | | | | 35 | 35 | 35 |
| 8 | | | | | 30 | 30 | 30 |
| 9 | | | | | 51 | 51 | 51 |
| 10 | | 94 | 94 | | 61 | 61 | 155 |
| Mean | 31.5 | 36.8 | 49.4 | 28.5 | 35.1 | 45.2 | 69.9 |
| SD | 21.9 | 34.7 | 33.6 | 23.5 | 17.7 | 22.6 | 37.4 |
| ANOVA p value: 0.941 |||||||||

Conclusion: Number of treatment days in each protocol is no significantly different.

FIG. 36

METHOD AND SYSTEM FOR THERAPEUTIC BRAIN STIMULATION USING ELECTROMAGNETIC PULSES

RELATED APPLICATION INFORMATION

This application claims the benefit of U.S. Provisional Application Ser. No. 61/973,827, filed on Apr. 1, 2014, hereby incorporated by reference as if set forth fully herein.

BACKGROUND OF THE INVENTION

1. Field of the Invention

The field of the present invention relates to systems and methods for treating neurologic or psychiatric disorders or conditions relating to the central and peripheral nervous systems, and more specifically, to techniques and delivery apparatus for therapeutic stimulation of neurons.

2. Background

The human brain is a complex organ, with a high incidence of illness. For example, it is estimated that in the United States, about 46% of the population will suffer from a diagnosable psychiatric disorder during their lifetime. Estimated lifetime prevalence by illness categories is: 29% anxiety disorders, 21% mood disorders, 15% substance disorders, 15% personality disorders, 8% attention deficit hyperactivity disorders, 3% psychotic disorders, and 3% autism spectrum disorders.

Neurologic disorders are also highly prevalent in the population. For example, tinnitus (a condition in which the affected person perceives sound in the absence of an external sound source) afflicts about 10% of the population, with a significant percentage of those affected being so severely impaired as to be unable to work or socialize. Chronic pain is reported by a third of the population and one in seven people suffer daily. Chronic lower back pain, which accounts for a significant percentage of all physician office visits in the United States and hundreds of billions of dollars in annual treatment costs, is now also thought to have its origins in the brain.

Fortunately for the many people suffering from neuropsychiatric disorders, treatments are being developed that show a great deal of promise in treating such illnesses. Unfortunately, current treatments prescribed to patients suffering from nervous system disorders are merely palliative at best, relieving pain but not the underlying cause of the ailment. For example, treatments for neurologic disorders, such as stroke, epilepsy and dementia, are often ineffective and do not address the root cause of the illness.

A. Chemical Treatments

Treatments offered for people suffering from neuropsychiatric disorders generally fall into one of two categories: chemical (psychopharmacologic) or neuromodulation (brain or peripheral nerve stimulation). The majority of psychiatric and neurologic illnesses are treated chemically, i.e., with pharmacologic agents. Neuropharmacologic and psychopharmacologic agents act at synaptic receptors to alter certain brain inputs in ways that reduce symptoms of mental and neurologic illness. However, chemical intervention has significant drawbacks. Often, the medication(s) must be taken for the rest of a patient's life to keep potentially disabling symptoms under control. If the medication regimen is stopped, the symptoms usually return, sometimes to a greater degree than were initially present, because the underlying pathologic neural wiring is not significantly altered. There are also potentially serious side effects, compliance problems, and widespread lack of efficacy (one-third of depressed and schizophrenic patients do not respond to known pharmacologic treatments) associated with medications.

B. Neuromodulation Treatments

In contrast to chemical treatments, neuromodulation involves modulation of the nervous system by electrically activating neurons in the body through stimulation. Neuromodulation treatments may also be neuroplastic. Neuroplasticity is the ability of the brain to rewire itself permanently in response to changing external or internal stimuli. The brain has a high degree of neuroplasticity in childhood, enabling children to learn in a highly efficient manner and heal from potentially devastating neural injuries. However, enhancement of neuroplastic properties for a particular brain area requires specific endogenous or artificial activation methods. Additionally, brain neuroplasticity tends to diminish rapidly with age. As such, age-related neuroplastic constraints can limit the effectiveness of most medical therapy of psychiatric or neurologic illnesses—at least for adults—to a slow, transient, or partial response.

Although still relatively undeveloped, neuromodulation techniques have shown promise in treating nervous system illnesses, including those that are refractory to chemical treatment methods. Neuromodulation techniques generally fall into one of two categories: peripheral nerve stimulation and central nerve stimulation. Central and peripheral neurons function similarly, using voltage-gated ion channels to transmit electrical impulses in the form of action potentials along nerve tracts leading directly or indirectly to specific regions in the brain or spinal cord. However, the two types of neurons differ in their locations; central neurons have cell bodies inside the dura mater enclosing the brain or spinal cord, while peripheral neurons have cell bodies outside the dura mater.

(1) Examples of Peripheral Neuromodulation

Peripheral nerve stimulation activates neurons having cell bodies outside the brain and spinal cord. An example of an invasive (penetrating the skin) peripheral nerve stimulation technique is vagus nerve stimulation ("VNS"). The vagus nerve is a peripheral cranial nerve important for homeostatic physiologic regulation (e.g., decreases heart rate, activates digestive tract), and generally extends from the brainstem to the abdomen, via various organs. VNS typically consists of surgically implanting an electronic stimulation device into the thoracic cavity and attaching linked electrodes. Stimulation of the vagus nerve transmits electrical impulses upward through the chest, neck, and skull base into the brainstem.

Another cranial nerve stimulation technique that is non-invasive is known as trigeminal nerve stimulation ("TNS"), which stimulates the superior branch of the trigeminal nerve. The axons of this nerve travel from the skin in the upper scalp, forehead and cranium to their extradural cell bodies inside the skull located the trigeminal nerve ganglion. Here, these neurons have synapses connecting them to various brain regions inside the dura mater. This is a relatively new and exciting technique, the effects of which are only now beginning to be explored.

(2) Example of Central Neuromodulation

In contrast to peripheral nerve stimulation, brain stimulation directly stimulates the brain or spinal cord. Transcranial magnetic stimulation ("TMS") is an example of brain stimulation. TMS is a non-invasive technique that typically involves placing an electromagnetic coil on or near the patient's head to depolarize or hyperpolarize neurons in specific brain areas. In particular, TMS uses electromagnetic induction to induce weak electrical currents using a rapidly changing magnetic field to increase or decrease activity in one or more brain regions.

TMS has diagnostic uses including determining the contribution of cortical networks to specific cognitive functions by disrupting activity in the focal brain region. TMS also has a number of therapeutic uses. For example, a variant of single pulse TMS is repetitive transcranial magnetic stimulation ("rTMS"). Repetitive TMS has been tested as a treatment tool for various neurological and psychiatric disorders including migraines, strokes, Parkinson's disease, dystonia, tinnitus, depression, and auditory hallucinations. The term repetitive transcranial magnetic stimulation is often used interchangeably with the term transcranial magnetic stimulation in the clinical domain. Likewise, the abbreviation rTMS is sometimes used interchangeably with TMS. For convenience, the term transcranial magnetic stimulation and abbreviation TMS will be used herein to encompass both single pulse and repetitive transcranial magnetic stimulation.

TMS techniques typically act on a volume of brain tissue that is approximately two to three centimeters in diameter. The localized nature of the intervention avoids systemic side effects that commonly plague current pharmacologic treatments. This type of approach also avoids adverse medication interactions and the difficulty of ascertaining compliance with treatment as the patient must be physically present for treatment to occur.

As with most any medical treatments, currently known TMS techniques also entail potential side effects or risks, including headache or local scalp discomfort, hypomania in bipolar patients, and in rare cases seizure activity. A patient's hearing may also be adversely affected, although there are not any reports of this occurring in humans. During treatment, rapid deformation of the TMS coil produces a loud clicking sound that increases with the stimulator intensity. Such clicking can theoretically affect hearing with sufficient exposure. Consequently, hearing protection is typically used during TMS treatment.

Recent advances have been made to neuromodulation treatments. For example, a novel therapeutic system comprising a brain stimulation device configured to stimulate a patient's brain by emitting an electromagnetic field based on certain stimulation parameters, a feedback device configured to measure data regarding brain activity, and a computer communicably connected to the feedback and stimulation devices has been.

While a substantial amount of research has shown that neuromodulation is safe and effective, questions remain about long-term efficacy and robustness. For example, current TMS techniques have not proven to be effective on all patients. In addition, significant relapse rates exist, requiring that the affected patient seek additional treatment possibly including additional TMS sessions.

(3) Comparison of Neuromodulation Techniques

Table 1 below compares some known electromagnetic neuromodulation techniques and illustrates certain characteristics of each. Only the last technique uses focused ultrasound to stimulate neurons; the remainder act electromagnetically. The laws of physics dictate that all electromagnetic fields have an electrical and a magnetic component, but neuromodulatory electromagnetic fields may act principally through their electrical component, their magnetic component, or a combination. Although neuromodulation techniques use different mechanisms of action, the end results are the same; hyperpolarization or depolarization of neural cell membranes is the final common pathway leading to therapeutic change. Similar pulse parameter sets applied using different neuromodulation techniques will likely have very similar effects due to the fact that neuromodulation is, by definition, a change in neural firing rates determined by the membrane potential of the associated target neurons. Therefore effective pulse parameter sets will likely have a universal value among the many forms of neuromodulation.

TABLE 1

Comparison of Neuromodulation Techniques

| Stimulation Type | Abbrev | Magnetic | Non-Invasive | External Device | Home or Office Procedure | Brain Stimulation |
|---|---|---|---|---|---|---|
| Transcutaneous Electrical Nerve Stimulation | TENS | NO | YES | YES | YES | NO |
| Transcutaneous Vagal Nerve Stimulation | t-VNS | NO | YES | YES | YES | NO |
| Trigeminal Nerve Stimulation | TNS | NO | YES | YES | YES | NO |
| Peripheral Nerve Field Stimulation | PNFS | NO | NO | NO | YES | NO |
| Peripheral Nerve Stimulation | PNS | NO | NO | NO | NO | NO |
| Vagus Nerve Stimulation | VNS | NO | NO | NO | NO | NO |
| Transcranial Electrical Stimulation (Direct Current, Alternating Current, Random Noise) | TES tDCS tACS tRNS | NO | YES | YES | YES | YES |
| Paired Associative Stimulation | PAS | YES | YES | YES | YES | YES |
| Transcranial Magnetic Stimulation | TMS | YES | YES | YES | YES | YES |
| Deep Transcranial Magnetic Stimulation | dTMS | YES | YES | YES | YES | YES |
| Multi-Coil Transcranial Magnetic Stimulation | mTMS | YES | YES | YES | YES | YES |

TABLE 1-continued

Comparison of Neuromodulation Techniques

| Stimulation Type | Abbrev | Magnetic | Non-Invasive | External Device | Home or Office Procedure | Brain Stimulation |
|---|---|---|---|---|---|---|
| Deep Brain Stimulation | DBS | NO | NO | NO | NO | YES |
| Magnetic Seizure Therapy | MST | YES | YES | YES | NO | YES |
| Electroconvulsive Therapy | ECT | NO | YES | YES | NO | YES |
| Focused Ultrasound | FUS | NO | YES | YES | YES | YES |

(4) TMS Delivery Techniques

Different techniques have been explored for delivering pulses in connection with TMS treatments. One particular TMS variant, known as Theta Burst Stimulation (TBS), involves the application of short bursts of relatively high-frequency (e.g., 50 Hz) pulses that may be applied continuously, or else repeated at a theta frequency (generally in the range of 4-8 Hz), upon the target site. Animal studies have long established that TBS can be an effective and safe method to induce changes in cortical excitability. Until relatively recently, it has only been applied to animals. However, in 2005, researchers reported safe and tolerable application of TBS in humans. See Huang, Y. Z., et al., *Theta Burst Stimulation of the Human Motor Cortex*, Neuron, 45(2), pp. 201206 (2005). In that study, TBS was applied as short bursts with three pulses/burst occurring at a pulse frequency of 50 Hz (i.e., separated by 20 millisecond intervals). These bursts were repeated at a burst frequency of 5 Hz (i.e., every 200 milliseconds). The TBS paradigm reported by Huang et al. was widely adopted by fellow researchers, who noted that TBS appeared to be superior to tonic stimulation in terms of inducing cortical excitability. There are other types of burst stimulation which may occur with burst frequencies in the delta range (0-4 Hz), alpha range (8-12 Hz), beta range (12-30 Hz) or gamma range (30-100 Hz), as generally described for example in De Ridder, D., et al., *Theta, Alpha And Beta Burst Transcranial Magnetic Stimulation: Brain Modulation In Tinnitus*, International Journal Of Medical Sciences, 4(5), 237 (2007).

Two kinds of theta burst stimulation have clinical relevance. The first type is referred to as "continuous" TBS (cTBS) and generally involves a continuous train of bursts applied to the target site, while the second type is referred to as "intermittent" TBS (iTBS) and generally involves a short train of bursts (typically 10 bursts) separated by an intertrain interval (typically several times longer than the duration of the train). iTBS and cTBS modulate human cortical excitability differently, with iTBS generally increasing it and cTBS generally decreasing it, according to past studies. When applied to motor cortex, TBS can cause long-term changes in motor-evoked potentials, with iTBS typically increasing the amplitude and cTBS typically decreasing the amplitude.

Several studies of human motor-evoked potential have indicated that TBS yields longer lasting post-stimulation effects on cortical activity than conventional TMS. These post-stimulation effects which outlast the stimulation interval are frequently referred to as long-term potentiation and long-term depression. Researchers have also found that long-term potentiation and long-term depression are not limited to motor cortex but occur in multiple brain regions. In addition, a few studies have noted that large pulse sequences of 1200 or more pulses divided into four sets of 300 pulses each delivered at increments of 15 minutes may increase the duration of the effect on motor-evoked potential.

(5) TBS Studies in Humans

TBS treatment has been considered for treatment of psychological disorders. Currently, however, there are only a handful of reported studies involving TBS for the treatment of depression. The most exhaustive of the three is an Israeli study assessing the effectiveness of a two-week TBS treatment using a burst frequency of 5 Hz and a pulse frequency of 50 Hz (TBS-50 Hz) on 32 patients diagnosed with depression. The results of this study were published in Chistyakov et al., *Safety, Tolerability And Preliminary Evidence For Antidepressant Efficacy Of Theta-Burst Transcranial Magnetic Stimulation In Patients With Major Depression*, International Journal of Neuropsychopharmacology, Vol. 13, No. 3, pp. 387-393 (2010). In this study, the patients were divided into two groups to assess laterality of treatment, as well as overall efficacy of theta 50 treatment. The first group received iTBS treatment applied as a 2 second train repeated every 10 seconds to the left dorsolateral prefrontal cortex (LDLPFC). The second group received cTBS applied as a single uninterrupted train to the right dorsolateral prefrontal cortex (RDLPFC). The patients were further divided into three sub-groups to evaluate dosage effect. The first group received 1200 stimuli per day, the second group received 1800 stimuli per day and the third group received 3600 stimuli per day. The results of this study showed an overall response rate (measured as 50% reduction of Hamilton Depression Rating Scale (HDRS) scores) of 56.3%. The results also indicated a dose effect since the increase of the number of stimuli added to the therapeutic effect.

The second study, conducted in Germany, also evaluated the therapeutic effect of TBS upon patients with depression, but limited the study to unilateral stimulation of the left dorsolateral prefrontal cortex (LDLPFC). The results of this study were published in Holzer et al, *Intermittent Theta Burst Stimulation (iTBS) Ameliorates Therapy-Resistant Depression: A Case Series*, Neuromodulation Vol. 3, Issue 3, pp. 181-183 (2010). In this study, seven treatment refractory patients received two daily sessions of TBS-50 Hz stimulation at 80% of resting motor threshold (rMT) over a three-week treatment period. Each iTBS sequence contained 600 pulses applied in an intermittent theta burst pattern with a 2 second stimulation interval and an 8 second intertrain interval. After the three weeks of treatment, Hamilton Depression Rating Scale (HDRS) scores dropped by 43% and Beck Depression Inventory (BDI) scores dropped by 49%. Three patients (42% remission rate) achieved remission and five patients (70% response rate) met the criteria for response.

A third study was reported in Wu et al, *Continuous Theta Burst Stimulation Of Right Dorsolateral Prefrontal Cortex*

Induces Changes In Impulsivity Level, Brain Stimulation Vol. 3, Issue 3, pp. 170-176 (2010). In that study, researchers reported improvement in a patient with treatment-resistant obsessive-compulsive disorder and major depressive disorder. The treatment involved TBS-50 Hz applied sequentially to bilateral cortical targets, with 10 sessions of cTBS over patient's right dorsolateral prefrontal cortex (RDLPFC) followed by 10 sessions of two seconds stimulation, 8 second intertrain interval iTBS over his left dorsolateral prefrontal cortex (LDLPFC). After six weeks of this treatment, a significant reduction of the patient's symptoms was noted, including a 34 point drop (from 49 to 15) of his Hamilton Depression Rating Scale (HDRS) score.

Although the results of the above studies are of interest, the TBS protocols employed did not, or are not proven, to work universally on all patients. Further, the level of benefit varied from patient to patient. In other studies or clinical experience, performed by or under the direction of the inventor of the disclosed invention herein, some patients receiving a TBS treatment with a 50 Hz repetition rate did not experience a decrease in their depression symptoms. The results from the earlier studies are also unproven in terms of duration of relief, relapse rate, and overall safety and efficacy, including long-term effects, which have not been well studied.

TBS is more comfortable for patients because, contrary to tonic stimulation, it is generally administered at an intensity below motor threshold. TBS also can be advantageous over tonic stimulation because the pulses are more concentrated which shortens treatment times. For example, a patient whose treatment regimen is 3600 pulses over RDLPFC using tonic 1 Hz inhibitory stimulation requires an hour of treatment time. The same protocol using cTBS only requires a treatment period of four minutes. However, excitatory TBS may require a treatment period in the range of 15-20 minutes or more.

In sum, current neurologic and psychiatric treatments leave considerable room for improvement. It would therefore be advantageous to provide novel and effective systems and methods of treating neurologic or psychiatric disorders that are non-chemical, non-invasive, neuroplastic, and curative.

It would further be advantageous to provide more efficacious systems and methods for delivering therapeutic neuromodulatory stimulation to the brain. It would also be advantageous to provide systems and methods for neuromodulatory stimulation to the brain that yield results in a greater percentage of the population, that provide a greater reduction in adverse symptoms, provide longer lasting effects, and/or reduce the rate of relapse. It would also be advantageous to provide systems and methods for neuromodulatory stimulation to the brain that require less time to administer, without substantially sacrificing, or while improving, actual or potential efficacy.

In addition to the above, or alternatively, it would be advantageous to provide systems and methods for neuromodulatory stimulation to the brain that are safer to the patient, require shorter treatment times, and improve patient comfort during therapy, without substantially sacrificing, or while improving, actual or potential efficacy.

It would further be advantageous to provide systems and methods for conveniently determining and/or selecting parameters for neuromodulatory techniques. Likewise, it would be advantageous to provide systems and methods for electromagnetic stimulation to the brain that require less specialized knowledge or training, and are able to be administered by a wider population of medical or other personnel.

SUMMARY

Certain embodiments disclosed herein are generally directed, in one aspect, to a therapeutic system comprising a non-invasive brain stimulation device or neuromodulation device configured to stimulate a patient's brain or nervous system by emitting electromagnetic pulses with a timing that improves the responsiveness of the brain or neurons to the pulses and may require only a relatively short train of pulses to achieve high efficacy. The brain stimulation device or neurological stimulation device may be employed to treat any of a large number of psychiatric and neurologic brain conditions.

In one particular aspect, a non-invasive brain stimulation device is configured to stimulate a patient's brain by emitting electromagnetic pulses according to a theta burst timing pattern that improves the responsiveness of the brain to the pulses and may require, for example, only a relatively short train of pulses to achieve relatively high efficacy. The electromagnetic pulse sequence or sequences may be pre-programmed into an electronic computer memory of the brain stimulation device, and conveniently selected by a treating physician or other individual via a user interface.

An exemplary embodiment of the disclosed subject matter is a therapeutic system comprising a brain stimulation device configured to stimulate a patient's brain by emitting an electromagnetic field based on certain stimulation parameters, and a timing controller that controls the measured delivery of theta burst pulses in order to effectuate a therapeutic treatment on the patient. The system may include a user interface for entering or selecting stimulation parameters for the theta burst pattern, and/or a durable computer memory for storing the stimulation parameters. The controller may read the selected stimulation parameters and utilize them to deliver the selected theta burst pattern. The brain stimulation device is preferably a non-invasive one. The stimulation parameters may be selected with the goal of enhancing a secondary brain treatment, for instance when excitatory TMS is given to the left dorsolateral prefrontal cortex (LDLPFC) preceding a secondary treatment in order to enhance regional or global brain neuroplasticity. The stimulation parameters may also be selected to increase or decrease activation (i.e., firing rates) in particular brain areas underlying the coil (assuming a treatment such as TMS using electromagnetic fields generated by one or more energized coils) or at downstream targets in a regional network. Instead of a brain stimulation device, the delivery device may be a neurological stimulation device.

According to one or more embodiments, the brain stimulation device is a transcranial magnetic stimulation device, which may be operated so as to provide excitatory or inhibitory pulse patterns directed to, e.g., the patient's left dorsolateral prefrontal cortex (LDLPFC) or right dorsolateral prefrontal cortex (RDLPFC), or other region of the brain.

According to one or more embodiments, the transcranial magnetic stimulation device (or other brain or neurological stimulation device) is operated to provide TBS according to prescribed parameters. For example, the transcranial magnetic stimulation (or other) device may deliver burst stimulation with the number of pulses per burst in the range of 2-1000, and more preferably in a range of 2-4 pulses/burst, and most preferably at either 2 pulses/burst or 3 pulses/burst, as may depend for example upon delivery frequency. The TMS (or other) device may deliver burst stimulation at a burst repetition frequency in the range of 0.1-150 Hz, and more preferably a range of 3-8 Hz (theta range or slightly lower), even more preferably a range of 4-7 Hz, and most preferably in a range of approximately 5-6 Hz. The TMS (or other) device may deliver burst stimulation with a pulse frequency greater than 0.2 Hz but less than 300 Hz, and more preferably in the range of 14-28 Hz, and even more preferably at approximately 20 Hz. The TMS (or other) device may also deliver burst stimulation with a pulse frequency in the range of 19-21 Hz for 3 pulses/burst patterns or 22-26 Hz for 2 pulse/burst patterns. The TMS (or other) device may deliver burst stimulation with a pulse/burst frequency ratio preferably between 3 and 5. The TBS may be in the form of iTBS with a stimulus train consisting of 1-1000 bursts/train, and more preferably in the range of 1 to 30 bursts/train and most preferably consisting of approximately 10 bursts/train. Each stimulation train occurs during a time interval determined by the corresponding parameter frequencies. These stimulus trains may be separated by an intertrain interval of between 0.01-300 seconds (0.003-100 Hz), more preferably by 1-30 seconds, and most preferably by approximately 5-10 seconds. Alternatively, the TBS may be in the form of cTBS which is characterized by a continuous train of bursts without an intertrain interval. In other embodiments involving a total number of delivered pulses per session of less than 300, and more preferably less than 100, and even more preferably between 4 and 39 total pulses, a number of bursts/train is preferably less than 14, more preferably between 2 and 13, more preferably is between 2 and 10, and most preferably is four. In such an embodiment, a single train may be delivered, or several trains where the total number of pulses is relative small (e.g., less than 300, or less than 100, or even more preferably less than 40). The TBS pulses may be applied for an overall interval of time until effective, which may be as short as a few milliseconds in duration, or could be repeated over a duration of minutes or possibly over a duration of hours or days in the case of a portable TMS device, for example.

According to one or more embodiments, the transcranial magnetic stimulation device (or other brain or neurological stimulation device) is operated to provide theta burst stimulation (TBS) where the ratio of burst frequency to pulse frequency is preferably between 3 and 5, and more preferably between 3.2 and 4.8, and most preferably is approximately 4. It has been discovered by the inventor hereof that applying iTBS according to the aforementioned parameters and ratios leads to a dramatic and unexpected increase in efficacy of the theta burst treatment for psychological conditions such as depression. It has further been discovered by the inventor hereof that applying iTBS according to the aforementioned parameters and ratio can surprisingly and unexpectedly lead to a successful treatment of a patient who has shown little or no response to an iTBS pattern delivered at a conventional theta burst frequency of 50 Hz.

According to one or more embodiments, a durable computer memory associated with the transcranial magnetic stimulation device may store iTBS parameters according to the above ratios and/or ranges, selectable through a user interface, thereby allowing convenient application of highly efficacious treatments to patients while requiring minimal effort from the treating physician or clinician. Stimulation parameters may be customized for individual patients, and durably stored for later use by saving the stimulation parameters as a pre-stored therapy regimen associated with the patient. Furthermore, by using prescribed settings found to be particularly efficacious across a wide range of patients, iTBS may be administered conveniently and with less cost, by personnel having less training and skill than otherwise might be required.

According to one or more embodiments, a non-invasive brain stimulation device comprising a transcranial magnetic stimulation device is configured to stimulate a patient's brain by emitting electromagnetic pulses according to a theta burst timing pattern, in order to induce long-term potentiation or long-term depression of neural activity. Optimal electromagnetic pulse sequences may be pre-programmed into an electronic computer memory of the brain stimulation device, and selected via a user interface. In other embodiments, other types of brain or neurological stimulation devices may be configured to provide brain or neural stimulation through artificial stimulating pulses according to particular timing patterns according to stimulation parameters that substantially increase efficacy.

Various embodiments as described herein may be applied to treatments of clinical depression, tinnitus or auditory hallucinations, generalized anxiety disorder ("GAD"), post-traumatic stress disorder ("PTSD"), or other psychological conditions. Embodiments as described herein may also, or alternatively, be used for cognitive enhancement or to otherwise improve or enhance a patient's psychological or mental condition.

Another exemplary embodiment of the disclosed subject matter is a method of therapeutic treatment comprising providing electromagnetic stimulation to a brain or the nervous system according to a burst pattern designed to improve long term efficacy for treating a neurologic or psychiatric disorder or to enhance cognitive, motor, social, or psychological skills, or to otherwise improve or maximize treatment.

An additional exemplary embodiment of the disclosed subject matter is a method of neuroplastic augmentation using brain or neural stimulation designed to augment, hasten, enhance, optimize, or improve a secondary neurologic or psychiatric treatment for a brain illness.

Further embodiments, variations and enhancements are also disclosed herein.

BRIEF DESCRIPTION OF THE DRAWINGS

Some non-limiting exemplary embodiments of the disclosed subject matter are illustrated in the accompanying drawings. Identical or duplicate or equivalent or similar structures, elements, or parts that appear in one or more drawings are generally labeled with the same reference numeral, optionally with an additional letter or letters to distinguish between similar objects or variants of objects, and may not be repeatedly labeled or described. Numerical attributes or dimensions of components and features shown in the figures are chosen for convenience or clarity of presentation. For convenience or clarity, some elements or structures are not shown or shown only partially or with different perspectives or from different points of views.

FIGS. 2A-2B are a more detailed block diagram of a particular example of a therapeutic brain stimulation system in accordance with the concepts illustrated in FIG. 1.

FIGS. 10A, 10B, 10C, 10D and 10E are waveform diagrams comparing delivery of TMS pulses employing tonic sequence and/or theta burst sequences of different frequencies.

FIG. 11 is a chart identifying sequences of various treatments for a study group of patients subject to the novel TMS treatments disclosed herein.

FIG. 12 is a chart identifying various treatment parameters and durations for the group of patients identified in FIG. 11.

FIGS. 13A-13B is a chart identifying demographical and clinical characteristics of the patients whose treatment information is summarized in FIGS. 11 and 12.

FIG. 14 is a chart identifying the TMS treatment parameters utilized for the patient study group described in FIGS. 11-13A-13B.

FIG. 15 is a chart indicating how patients in the study group responded to treatments summarized in FIG. 14, in terms of BDI-II scale scores.

FIG. 20A is a chart illustrating changes in motor evoked potential and using different combinations of pulse sequence parameters, and FIG. 20B is a chart indicating the determined statistical significance of the values in the FIG. 20A chart.

FIGS. 26B, 26C and 26D are charts with the underlying data for the graph of FIG. 26A.

FIG. 27B is a chart with the underlying data for the graph of FIG. 27A.

FIG. 31 is a chart identifying demographical and clinical characteristics of patients from a larger study of theta burst TMS stimulation including at 20 Hertz.

FIG. 33 is a chart identifying sequences of various treatments for the study group of patients of FIG. 31.

FIG. 35 is a chart identifying the TMS treatment parameters utilized for the patient study group described in FIGS. 31-33.

FIG. 36 is a chart identifying various treatment parameters and durations for the group of patients identified in FIGS. 31-33.

DETAILED DESCRIPTION OF PREFERRED EMBODIMENTS

Figure 1:
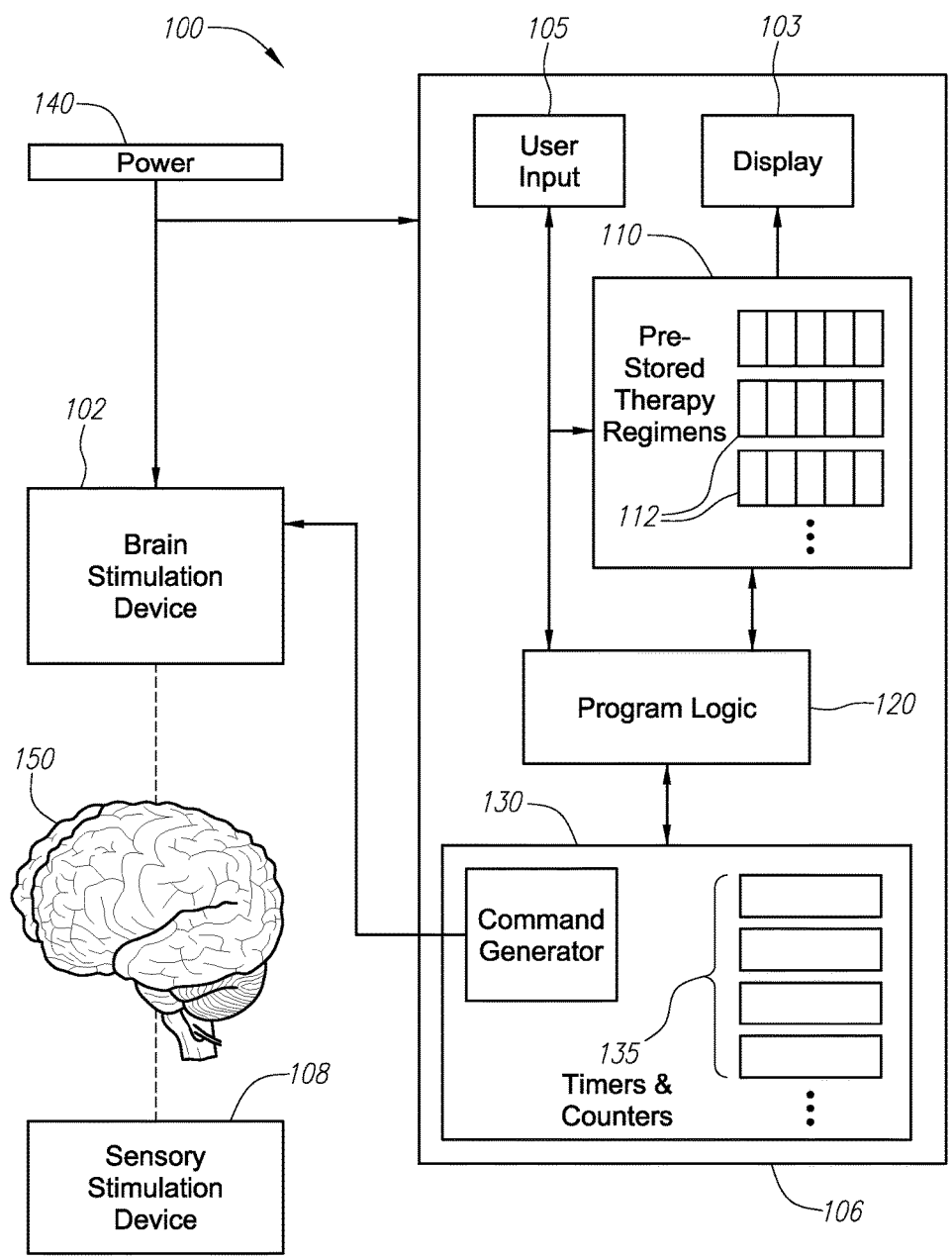
FIG. 1 is a block level diagram of a therapeutic brain stimulation system according to an exemplary embodiment of the disclosed subject matter.

Certain embodiments disclosed herein are generally directed, in one or more aspects, to a novel therapeutic system comprising a non-invasive brain stimulation device configured to stimulate a patient's brain by emitting electromagnetic pulses with a predetermined timing that, among other things, may improve the responsiveness of the brain to the pulses and/or may require only a relatively short train of pulses to achieve high efficacy. The brain stimulation device may be employed to treat any of a large number of neurologic conditions. In a preferred embodiment, the non-invasive brain stimulation device comprises a transcranial magnetic stimulation (TMS) device configured to stimulate a patient's brain by emitting electromagnetic pulses according to a theta burst timing pattern, the parameters of which may be pre-programmed into an electronic computer memory associated with the device. A user interface may be provided to allow a physician or other treatment provider to conveniently select the appropriate parameters for the desired treatment.

According to one or more embodiments, the transcranial magnetic stimulation (or other) device is operated to provide theta burst stimulation (TBS) according to prescribed parameters. For example, the transcranial magnetic stimulation (or other) device may deliver burst stimulation with the number of pulses per burst in the range of 2-1000, and more preferably in a range of 2-4 pulses/burst, and most preferably at either 2 pulses/burst or 3 pulses/burst. The TMS (or other) device may deliver burst stimulation at a burst repetition frequency in the range of 0.1-150 Hz, and more preferably a range of 3-8 Hz (theta range or slightly lower), even more preferably a range of 4-7 Hz, and most preferably in a range of approximately 5-6 Hz. The TMS (or other) device may deliver burst stimulation with a pulse frequency greater than 0.2 Hz but less than 300 Hz, and more preferably in the range of 14-28 Hz, and even more preferably at approximately 20 Hz. The TMS (or other) device may also deliver burst stimulation with a pulse frequency in the range of 19-21 Hz for 3 pulses/burst patterns or 22-26 Hz for 2 pulse/burst patterns. The TMS (or other) device may deliver burst stimulation with a pulse/burst frequency ratio preferably between 3 and 5. The TBS may be in the form of iTBS with a stimulus train consisting of 1-1000 bursts/train, and more preferably in the range of 1 to 30 bursts/train and most preferably consisting of approximately 10 bursts/train. Each stimulation train occurs during a time interval determined by the corresponding parameter frequencies. These stimulus trains may be separated by an intertrain interval of between 0.01-300 seconds (0.003-100 Hz), more preferably by 1-30 seconds, and most preferably by approximately 5-10 seconds. Alternatively, the TBS may be in the form of cTBS which is characterized by a continuous train of bursts without an intertrain interval.

It should be understood that, in the various embodiments disclosed herein, a theta burst would include bursts of pulses separated by gaps of no pulse delivery or else delivery of low amplitude pulses that are therapeutically ineffective or insignificant. For example, it is possible to deliver low amplitude pulses between bursts at, e.g., 10% of motor threshold that do not result in meaningful brain or neural response, and such low amplitude pulses would not change the fact that a theta burst is delivered. As a concrete example, delivery of a 20 Hz "tonic" frequency with every fourth pulse at a very low intensity (e.g., 10% of motor threshold) would still be considered a theta burst pattern, with the fourth pulse being ignored by the brain. Furthermore, each pulse in a theta burst pattern need not be of identical amplitude. For example, a three-pulse theta burst pattern with pulses respectively delivered at 90%, 80% and 70% of motor threshold would not alter the fact that the timing of the pulses is dictated by a theta burst pattern.

According to another separate aspect of the instant disclosure, a TMS or other device is operated to deliver a total number of delivered pulses per session of less than 300, and more preferably less than 100, and even more preferably between 4 and 39 total pulses, a number of bursts/train is preferably less than 14, more preferably between 2 and 13, more preferably is between 2 and 10, and most preferably is four. In such an embodiment, a single train may be delivered, or several trains where the total number of pulses is relatively small (e.g., less than 300, or less than 100, or even more preferably less than 40). The TBS pulses may be applied for an overall interval of time until effective, which may be as short as a few milliseconds in duration, or could be repeated over a duration of minutes or possibly over a duration of hours or days in the case of a portable TMS device, for example.

According to another separate aspect of the instant disclosure, the transcranial magnetic stimulation device is operated to provide theta burst stimulation (TBS) where the ratio of burst frequency to pulse frequency is preferably between 3 and 5, and more preferably between 3.2 and 4.8, and most preferably is approximately 4.

1. Therapeutic Brain Stimulation Devices and Systems

Figure 7:
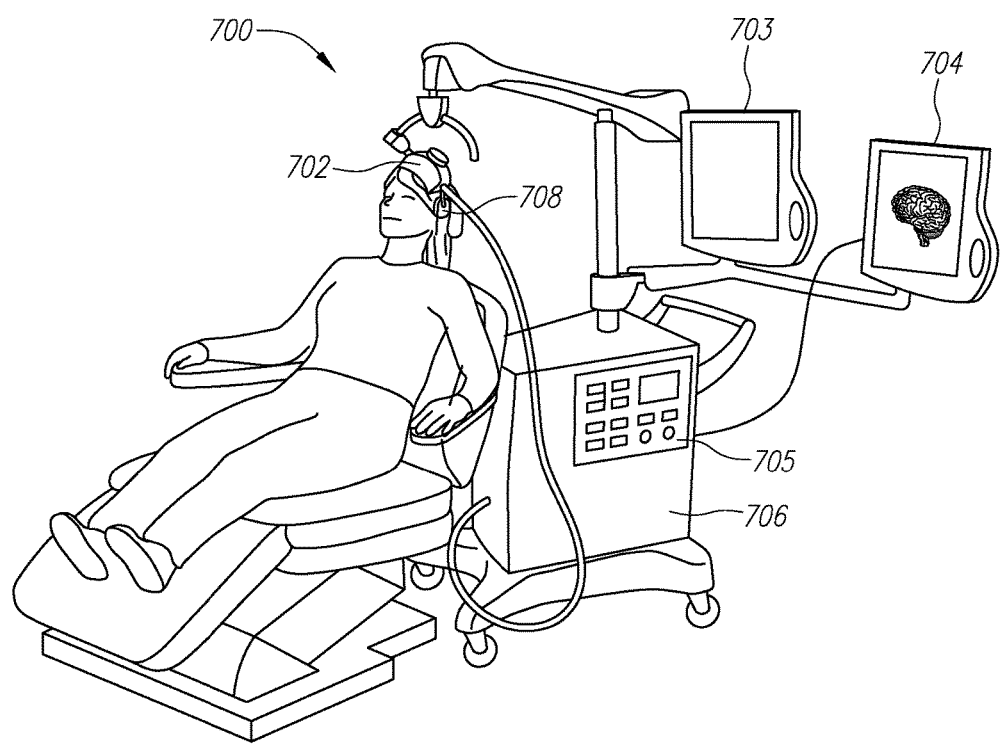
FIG. 7 is a perspective view of a patient being treated for a condition (e.g., a neurologic or psychiatric disorder or an enhancement treatment) using a therapeutic brain stimulation system according to an exemplary embodiment of the disclosed subject matter.

FIG. 7 illustrates an exemplary embodiment of a therapeutic brain stimulation system 700 configured to stimulate a patient's brain by emitting an electromagnetic field based on certain stimulation parameters and, more specifically, is a perspective view of a patient being treated for a condition (e.g., a neurologic or psychiatric disorder or an enhancement treatment) using a therapeutic brain stimulation system according to an exemplary embodiment of the disclosed subject matter. In the example of FIG. 7, the therapeutic brain stimulation system 700 comprises, among other things, a TMS brain stimulation device 706 (typically including electronics for generating electromagnetic pulses and a computer) which includes a stimulation delivery mechanism 702 (e.g., a cap) for non-invasively delivering electromagnetic pulse stimuli to the brain under control of the TMS brain stimulation device 706, based on certain stimulation parameters as will be described in more detail herein. The TMS brain stimulation device 706 may be controlled or adjusted through a touchscreen interface 703, and/or may have a control panel 705 integrated therewith for interfacing with the device. The therapeutic brain stimulation system 700 also preferably includes a monitor screen 704 which can be used, for example, to facilitate placement of the stimulation delivery mechanism 702 and targeting of the electromagnetic pulse delivery. For instance, the monitor screen may be used to display EEG measurements superimposed upon a patient's previously imaged brain scan obtained using MRI scanning techniques.

In addition, the therapeutic brain stimulation system 700 may include a TMS brain stimulation device 706 and stimulation delivery mechanism 702 that are based on or incorporate the hardware or functionality of, for example, a TMS device manufactured by Neuronetics, Inc. such as that of the NeuroStar® TMS Therapy System. The TMS brain stimulation device 708 and stimulation delivery mechanism 702 may alternatively be based on or incorporate the functionality of a TMS device manufactured by The Magstim Company Ltd. such as the Magstim Rapid, Super Rapid, Super Rapid Plus, Magstim BiStim, and Magstim 200; a TMS device manufactured by ANT B.V. such as the Smart-Move; a TMS device manufactured by MagVenture A/S such as the MagPro®; a TMS device manufactured by Neotonus, Inc. such as the Neopulse Stimulator; a TMS device manufactured by Nexstim, Inc. such as the eXimia TMS Stimulator; or one or more similar such devices manufactured by Neuronix Ltd. (Israel), eNeuras Therapeutics (Sunnyvale, Calif.), or Neostim (San Mateo, Calif.). Likewise, the TMS device may be based on or incorporate the hardware or functionality of a machine made by another manufacturer. The brain stimulation device 102 may also be a transcranial direct current stimulation ("tDCS") device such as the 1×1 tDCS or the 1×1 Limited Total Energy device or the 1×1 Clinical Trials stimulator. The tDCS device may be a product of Rogue Resolutions such as the neuroConn DC-Stimulator, the neuroConn DC-Stimulator Plus, the NeuroConn DCStimulator MR, or the neuroConn DC-Stimulator MC; or a product of Magstim such as the HDCkit, the HDCstim, or the HDCprog. The tDCS device may also be a high-definition tDCS device such as one manufactured by Soterix Medical, Inc. Likewise, the brain stimulation device may be a patented tDCS or HD-tDCS device made by another manufacturer.

In other embodiments, the therapeutic brain stimulation system 700 may include a device other than a TMS brain stimulation device 706, that is nonetheless based on the stimulation of neurons using artificial stimuli. Thus, for example, the brain stimulation system 700 may include or comprise, instead of the TMS brain stimulation device 706, a vagal nerve stimulator, a transcranial stimulation device other than a TMS device (such as, for example, alternating current transcranial stimulation with electrodes contacting the scalp), a peripheral nerve stimulation device, a transcranial ultrasound stimulation device, a deep brain stimulation device, or any device that involves nerve depolarization and that utilizes periodic artificial stimuli, including any of the techniques previously set forth in Table 1. Because the various parameters for artificial stimuli described herein are believed to be closely attuned to natural frequencies of the brain, any technique besides TMS that is used to stimulate the brain in order to alter its plasticity or impose lasting effects should be able to utilize these same or similar parameters successfully.

The therapeutic brain stimulation system 700 may optionally include a feedback device to measure brain activity or activity relating thereto. The feedback device may present graphical output through the display monitor 704, or else through some other output, which may be recorded. Indirect brain stimulation is not limited to TMS but may also involve tDCS or HD-tDCS, or other techniques including optical stimulation, ultrasound stimulation, or other types of artificial stimulation, and in each case the effect thereof may be monitored and recorded through a suitable physiological detector and recorded. Among other things, the feedback device may be configured to perform real-time QEEG brain mapping, cordance mapping (as disclosed in U.S. Pat. No. 5,309,923, hereby incorporated by reference), swLoreta brain imaging, or global frequency spectrum power. The feedback device may also be configured for Loreta, sLoreta, magnetoencephalography ("MEG"), magnetic resonance imaging ("MRI"), near infrared spectroscopy ("NIRS") diffusion tensor imaging ("DTI"), functional magnetic resonance imaging ("fMRI"), positron emission tomography ("PET"), single photon emission computer tomography ("SPECT"), nuclear magnetic spectroscopy ("NMS"), piezoelectric positional feedback, EMG, EKG, physiological parameters (HR, GSR, temperature, etc.), ultrasound, video camera, optical measurement device, or electrode potentials. Measurements obtained from the feedback device can be used to adjust stimulation parameters to maximize treatment benefit, including detailed mapping of the sensory cortex for phantom perceptual disorders, or may be used to determine optimal parameters individualized or customized for a given patient. Examples of feedback devices that may be used in connection with the various embodiments described herein include neuronavigation devices manufactured by ANT B.V., such as the Visor or Visor-lite that includes brain computer interface ("BCI") technology, the MagVenture neuronavigation system, or the Brainsight neuronavigation system.

The TMS brain stimulation device 706 may be configured to receive input from the feedback device, if utilized, and may operate to adjust stimulation parameters in real time and deliver the output to the patient to enhance neuroplasticity in the patient's brain. For example, the computer may be configured to adjust TMS parameters such as intensity (expressed as percentage of motor threshold ("MT")) until there is synchronous neural depolarization of the cerebral cortex after the TMS pulse train. As explained later herein, a feedback device may also be used to facilitate determination of optimal pulse and burst frequency parameters, and possibly other parameters, characterizing the delivery of TMS stimulating pulses. By doing so, custom parameter adjustments for each individual patient can be obtained to realize the highest possible remission rate in response to TMS therapy in a variety of illness treatment contexts.

Real-time monitoring can also provide safety enhancement. For example, the TMS brain stimulation device 706 may include one or more software algorithms that detect the active frequency for treating tinnitus disorders and modifies the TMS inhibitory stimulation so it is at a frequency that is not a harmonic of the hotspot. The computer's output may also comprise a signal that modifies the stimulation due to input indicating coil overheating, significant scalp discomfort, or pre-seizure activity. For example, with real-time EEG monitoring, any potential seizure is going to be preceded by abnormal spike activity on EEG. Such activity is picked up during real-time monitoring. The TMS brain stimulation device 706 may be configured to include a software algorithm that continuously scans for seizure activity and applies seizure-specific inhibitory stimuli parameters or modifies the treatment parameters to low frequency (1 Hz) stimulation if pre-seizure waveforms begin to appear to suppress any seizure activity that may develop. The output may further comprise a signal designed to move the brain stimulation delivery mechanism 702 to emit an electromagnetic field to a different part of the patient's brain or to emit the electromagnetic field from a different distance or orientation to the same part of the brain.

The therapeutic brain stimulation system 700 may optionally include a sensory stimulation device 708 to provide additional sensory stimulation to the patient in connection with the artificial stimuli from the TMS device or other brain stimulation device, either before, during, or after brain stimulation. The sensory stimulation device 708 may be configured to deliver one or more sensory stimulations depending on the disorder being treated. Preferably, the patient should be paying attention to the sensory stimulation when applied. Examples of sensory stimuli that may be applied via the sensory stimulation device 708 may include music, white noise, or sequenced pure tones individually notched for each ear at a patient's tinnitus frequency; pure tone stimuli at the trauma frequency or in a notched pattern around the tinnitus frequency; the Dalton Stimulus for the suppression of tinnitus; silence or noise cancellation to treat auditory hallucinations; individually selected emotionally uplifting music to treat depression or enhance cognition;

trauma-related virtual-reality stimulation to treat PTSD (with or without prior propranolol administration); haptic stimulation of specific dermatomes for treatment of chronic pain syndromes; low-intensity electrical stimulation of certain muscle groups; physical exercises; guided virtual-reality experiences or recorded video stimulation of athletic performances to enhance motor skills; guided mental exercise instructions to enhance cognitive skills; videoconferenced psychotherapeutic treatment (including cognitive behavioral therapy); guided imagery; guided meditation to enhance psychological skills; or guided simulations of social situations to enhance social skills or autism spectrum disorders. Examples of sensory stimulation devices 708 that may be used in one or more aspects of the exemplary embodiments include headphones, monitors displaying video recordings, or virtual reality devices or systems. The sensory stimulation device 708 may also include medications, chemicals, physiological manipulations, or other stimulation devices or techniques designed to induce neuroplastic changes in targeted neuroanatomical substrates or circuits.

Details of preferred embodiments in accordance with certain aspects of the disclosure herein appear in FIGS. 1 and 2A-2B. FIG. 1 is a functional block level diagram of a therapeutic brain stimulation system 100 according to an exemplary embodiment of the disclosed subject matter. In FIG. 1, the therapeutic brain stimulation system 100 includes devices configured to stimulate a patient's brain by emitting an electromagnetic field based on certain stimulation parameters in a manner similar to that described for FIG. 7. Although in FIG. 1 certain functional blocks are shown separately for purposes of convenience or explanation, this should not be understood to imply or require that the functional blocks are necessarily separate physical devices. In the example of FIG. 1, the therapeutic brain stimulation system 100 preferably comprises, among other things, a TMS brain stimulation device 102 that includes electronics for generating electromagnetic pulses and a stimulation delivery mechanism (e.g., a cap) for non-invasively delivering electromagnetic pulse stimuli to a patient's brain 150 under control certain stimulation parameters as will be described in more detail herein, and may be any of the types of TMS brain stimulation devices previously described in connection with FIG. 7. The TMS brain stimulation device 102 is preferably controlled by a controller 106 that may be integrated, in whole or part, with the same physical components or housing of the TMS brain stimulation device 102. The controller 106 may have a user input 105, such as a touchscreen interface, keyboard, mouse, and/or other input devices, as well as a display 103 that may be embodied as a monitor, a set of readouts, an LED display, or any other visual display. If embodied as a monitor screen, then the display 103 may be used, for example, to facilitate placement of the stimulation delivery mechanism (e.g., cap) and/or coils that are utilized in the delivery of the electromagnetic pulses, although a separate monitor screen may be used for that purpose, if desired.

Figure 3:
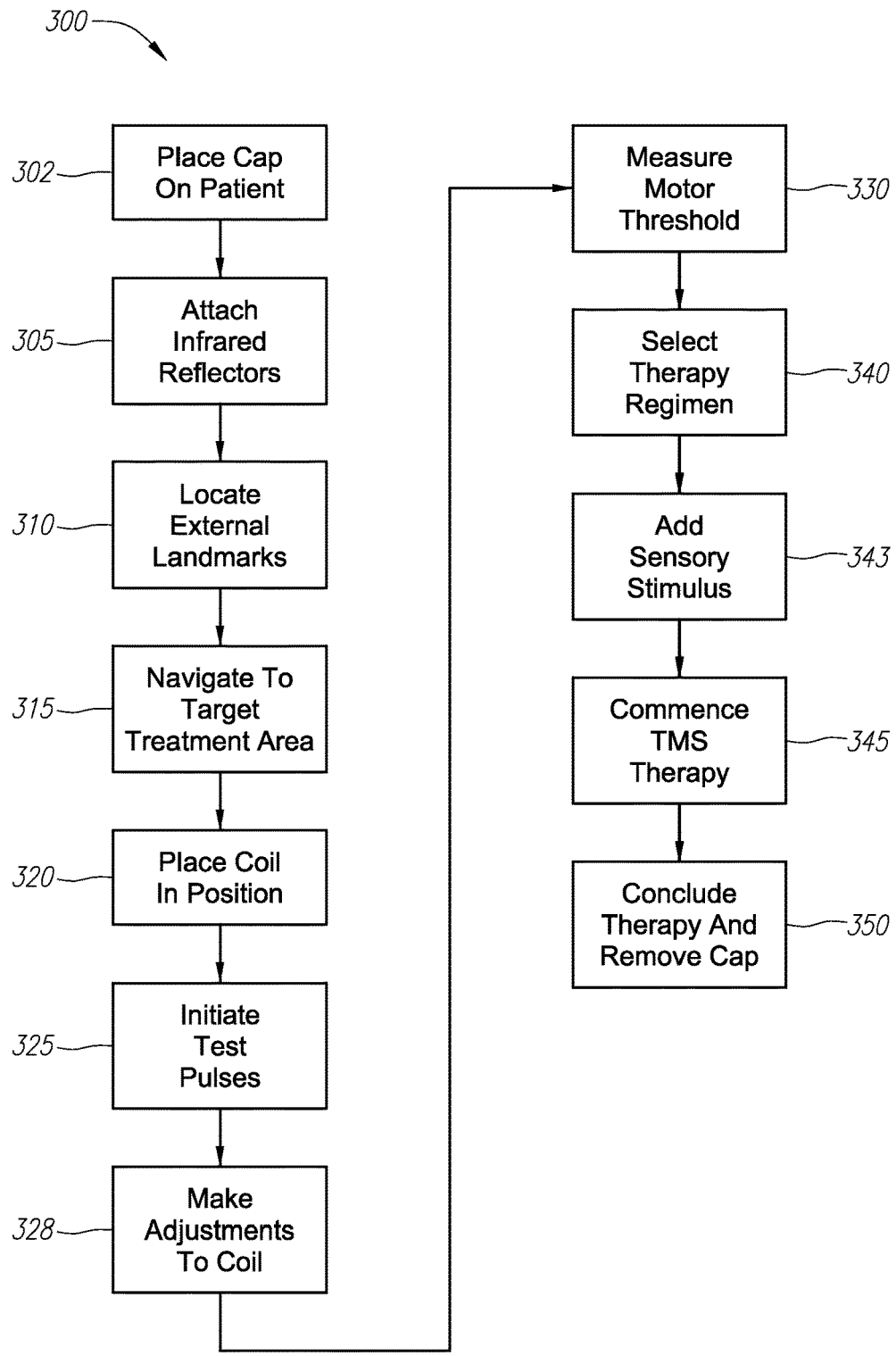
FIG. 3 is a flow chart illustrating a process for selecting theta burst parameters for a given patient in accordance with one or more embodiments disclosed herein, in order to, e.g., treat neurologic or psychiatric disorders, as may be used in connection with the systems illustrated in FIGS. 1 and/or 2 for example.
Figure 6:
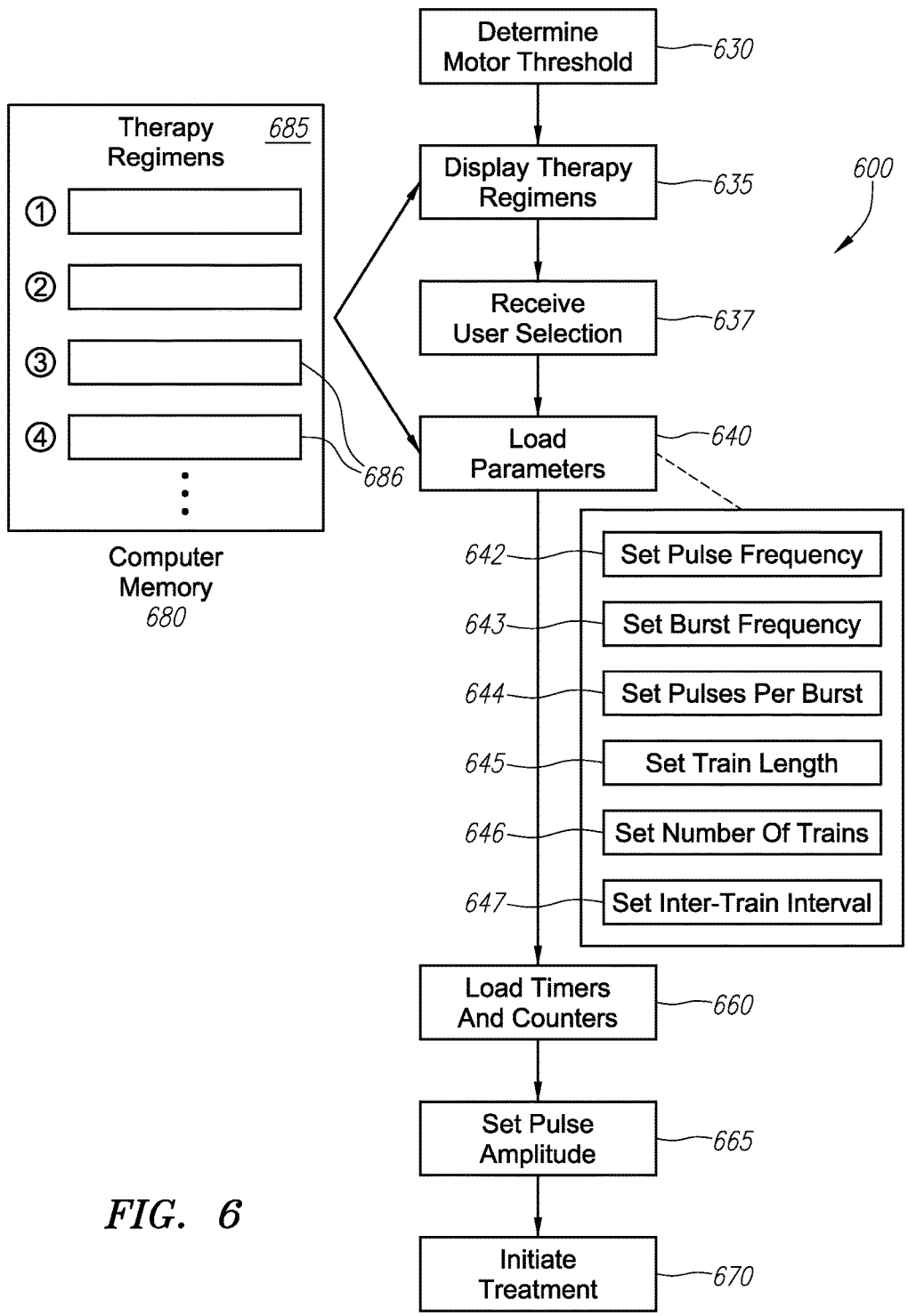
FIG. 6 is a flow chart illustrating a process for selecting theta burst parameters from among a set of predetermined parameters, as may be used, for example, in connection with the therapeutic brain stimulation system(s) illustrated in FIGS. 1, 2A-2B and/or FIG. 9.

The controller 106 preferably includes a variety of functional blocks that are involved in the selection of parameters for, e.g., TMS pulse delivery, and for generating commands relating to the selected parameters. To facilitate its functions, the controller 106 may incorporate a computer or microprocessor, including an embedded processor, or an ASIC or dedicated hardware-based processor. Thus, the controller 106 preferably comprises control logic 120 that may be implemented in software or hardware, as may be most convenient, and which preferably operates to facilitate processes such as illustrated in FIGS. 3 and 6, described later. The controller 106 also preferably includes a durable memory area 110 for storing predetermined therapy regimens 112 each of which involve a set of parameters for delivery artificial stimulation. In a preferred embodiment in which TMS stimulation is utilized, the predetermined therapy regimens 112 may include two or more of the following parameters: burst repetition frequency, pulse frequency (theta frequency), number of pulses per burst, total number of pulses (or bursts) per session, and inter-train interval. The parameters may also include pulse frequency or burst frequency in combination with pulse/burst frequency ratio. In addition, the predetermined therapy regimens 112 may also include parameters relating to the pulses, such as the amplitude (typically in terms of motor threshold percentage), pulse waveform shape (such as monophasic, biphasic, triangle wave, etc.), pulse polarity, polarity pattern (if multiple pulses per burst), or burst polarity pattern, by way of example.

The predetermined therapy regimens 112 may further include multiple sets of parameters relating to more complex treatments, and may include pre-stored information relating to a combination of therapies for a treatment session. For example, the predetermined therapy regimens 112 may include one or more parameters indicating whether the therapy should be left dorsolateral prefrontal cortex (LDLPFC), right dorsolateral prefrontal cortex (RDLPFC), interleaved (i.e., alternate between LDLPFC and RDLPFC), sequential, or simultaneous. The predetermined therapy regimens 112 may be stored in any suitable manner; for example, they may be downloaded from a remote source (assuming the controller 106 has network connectivity) or from a computer-readable medium, or may be entered and saved for the user input 105. For example, the predetermined therapy regimens 112 may be read from a computer disk, flash memory drive, or other storage medium. The durable memory area 110 preferably comprises magnetic or other non-transient storage means, such as a flash memory or EEPROM memory. Besides being programmed from various user sources, the predetermined therapy regimens 112 may also be entered after an automated or semi-automated search routine to identify optimal pulse parameters, whether through a user command or as part of the automated or semi-automated process. Such action is useful as part of the process for determining individualized or customized pulse delivery parameters for specific patients, as will be discussed in more detail hereafter.

The controller 106 also preferably includes a pulse delivery command unit 130 that provides commands to the brain stimulation device 102 to deliver artificial stimuli according to a particular predetermined therapy regimen 112. When a therapy session is initiated, the control logic 120 preferably interacts with the user input 105 and display 103 to allow a physician, clinician, or other operator to select a suitable therapy regimen from among the stored predetermined therapy regimens 112, or to allow the operator to enter parameters manually for a customized therapy session. In response to an operator request entered via the user input 105, the control logic 120 may cycle through the predetermined therapy regimens 112 and display their particulars on the user display 103, from which the operator may select one of the predetermined therapy regimens 112 using the user input 105. To facilitate selection, the predetermined therapy regimens 112 may have designated names associated with their intended function or treatment, such as "depression" or "severe depression", "tinnitus", "enhancement", etc., or may be associated with specific patient names if customized for particular patients.

Once a predetermined regimen is selected, the control logic 120 takes the parameters from the selected predetermined therapy regimen 112 and passes them to the pulse delivery command unit 130, so that it can generate and provides commands to the brain stimulation device 102 to deliver artificial stimuli according to the selected predetermined therapy regimen 112. The pulse delivery command unit 130 may include a number of times and counters 135 (either software or hardware) for timing the various pulse parameters in order to generate the pulse commands at the appropriate point, according to well known techniques in the art. Conventional TMS stimulation devices generally permit manual selection of parameters via a control panel or touchscreen, including burst frequency, pulse frequency, number of pulses per burst, and inter-train interval, among others; hence, the same type of timers, counters, and other electronics necessary to time artificial stimuli according to theta burst patterns as used in conventional TMS devices can be employed in the pulse delivery command unit 130. However, the source of the parameters in this case is the predetermined therapy regimens 112 instead of manual inputs, although manual input means may also be used if no suitable predetermined therapy regimen 112 exists, or to modify the parameters of an existing predetermined therapy regimen 112. The control logic 120 may facilitate the loading of the various pulse parameters retrieved from the stored or modified predetermined therapy regimen 112, into the timers and counters 135 or other locations within the pulse delivery command unit 130. Based on the timing dictated by the parameters from the selected predetermined therapy regimen, the pulse delivery command unit 130 delivers commands to the brain stimulation device electronics 102, which energizes a coil or other stimulation delivery mechanism when commanded to do so, for delivery to the patient's brain 150.

The computer 106 may preferably contain an optimization algorithm wherein each of the treatment parameters is statistically correlated to the changes in activation level in the region of interest using an optimization protocol, preferably multivariate linear regression. With each repetition of the process, the treatment parameters may be systematically varied to determine the coefficients of multiple determination for each of the principal treatment parameters of the brain stimulation device 102. Each iteration of electromagnetic stimulation of the target area may have modified parameters in accordance with the results of the statistical regression analysis so the electromagnetic stimulation of the target area may become more and more effective over the duration of the brain stimulation neuroplasticity modulation element of the psychiatric or neurologic treatment. The brain stimulation neuroplasticity modulation technique may occur before, during, or after the neurologic or psychiatric treatment depending on the specific details of the treatment protocol and the output measurements of the feedback device 104. For example, when the secondary psychiatric or neurologic treatment is also a brain stimulation treatment such as ECT, then the neuroplastic modulation may occur just before the emission of the current charge. When the augmented psychiatric or neurologic treatment is a medication treatment, the neuroplastic modulation may occur subsequent to ingestion of the medication. When the augmented psychiatric or neurologic treatment is a form of speech therapy due to a neurologic insult, the neuroplastic modulation may temporally coincide with the administration of the speech therapy training.

As previously noted in connection with FIG. 1, the therapeutic brain stimulation system 100 may also optionally include a sensory stimulation device 108 that provides another means of stimulation, such as music for example, to the patient concurrently with the TMS or other stimulation treatment.

Figure 9:
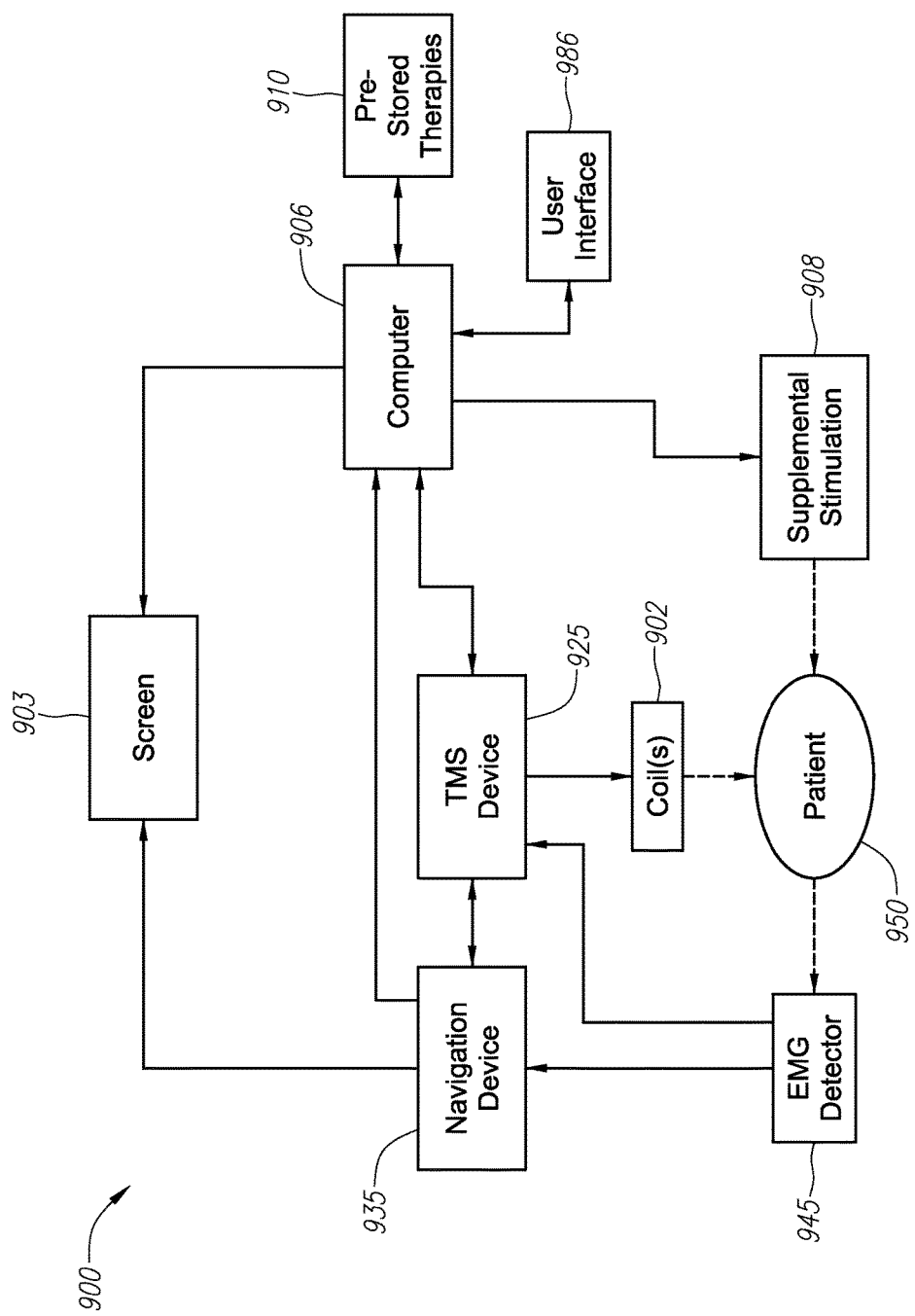
FIG. 9 is a block diagram of a particular example of a therapeutic brain stimulation system illustrating various components, as may be used for instance in connection with the techniques discussed in relation to FIG. 1.

FIG. 9 is a functional block diagram of a particular example of a therapeutic brain stimulation system 900 illustrating various basic system components, as may be used for instance in connection with the techniques discussed in relation to FIG. 1 and/or FIG. 7, and includes devices configured to stimulate a patient's brain by emitting an electromagnetic field based on certain stimulation parameters in a manner similar to that described for FIGS. 1 and/or 7. In FIG. 9, the therapeutic brain stimulation system 900 is designed to deliver TMS pulses according to predetermined therapy regimens stored in a durable memory area 910 of the system, in a manner similar to explained with FIG. 1. Again, while different functional blocks are illustrated, some of the described functions may be embodied or combined, in whole or part, in a single physical hardware device.

In FIG. 9, a TMS brain stimulation device 925, which may be a machine or device such as the NeuroStar® TMS Therapy System or a TMS device manufactured by The Magstim Company Ltd. such as the Magstim Rapid, Super Rapid, Super Rapid Plus, Magstim BiStim, or Magstim 200, or a device incorporating the basic functionality thereof, may deliver artificial stimulating electromagnetic pulses to a patient 950 through a pulse delivery mechanism 902, such as one or more coils. The TMS brain stimulation device 925 may operate under control of a computer 906 or other controller, which may be physically integrated with the TMS brain stimulation device 925 or separate therefrom. The computer 906 or other controller may coordinate various activities relating to diagnostics and therapy management, and may be operated via a user interface 986 such as a touchscreen, keypad, control panel, mouse, and/or other user input means. The computer 906 may be coupled to, and control, a supplemental stimulation source 908, such as an audio source (e.g., music) played through headphones, to supplement the patient's TMS treatment. The computer 906 may also provide visual output on a screen 903 that may be embodied as a monitor, a set of readouts, an LED display, or any other visual display, for viewing by a physician, clinician or other operator.

In the example of FIG. 9, the location of the pulse delivery mechanism (e.g., coils) 902 may be initially placed with the assistance of a navigation device 935 such as a Neuronavigator or other similar system, as previously described. An EMG detector 945 may detect neural motor activity in a patient (such as via a finger sensor) and the captured information may be provided to the navigation device 935 and TMS brain stimulation device 925. The navigation device may display a previously captured MRI scan of the patient's brain on the screen 903, along with real-time information captured from the delivery of pulses by the TMS brain stimulation device 925, as detected by the EMG detector 945, to facilitate optimal placement of the pulse delivery mechanism 902, such as coils, according to conventional techniques.

In the system 900 of FIG. 9, one of the predetermined therapy regimens in the durable memory area 910 may be read out and selected using the user interface 986. The parameters for the predetermined therapy regimens may be displayed on the screen 903 or a different monitor or display. The operator may cycle through the various predetermined therapy regimens in order to select the prestored combination of parameters most well suited to the particular patient. The predetermined therapy regimens may also include regimens previously adapted to or customized for a specific patient. As noted before in connection with FIG. 1, the parameters of the predetermined therapy regimens may include burst repetition frequency, pulse frequency (theta frequency), number of pulses per burst, total number of pulses (or bursts) per session, inter-train interval, pulse/burst frequency ratio, and/or parameters relating to the pulses, such as the pulse amplitude, pulse waveform shape (such as monophasic, biphasic, triangle wave, etc.), pulse polarity, polarity pattern (if multiple pulses per burst), or burst polarity pattern, for instance. The predetermined therapy regimens may further include multiple sets of parameters relating to more complex treatments, and may include pre-stored information relating to a combination of therapies for a treatment session.

In addition to facilitating placement of the pulse delivery mechanism, the EMG detector 945 (or another biosensitive detector that reflects neurological response activity) may also be used as a feedback mechanism in determining customized or optimal pulse parameters for a given patient. In particular, the computer 906 may operate to cycle through the predetermined therapy regimens, or else may be programmed to cycle systematically through combinations of pulse parameters, focusing on those combinations of parameters that have previously been found to be effective for the type of condition matching the patient 950 being treated, while the patient's response to each of the treatments is detected through the EMG detector 945 and potentially monitored on the screen 903. For example, the computer 906 may obtain the feedback information from the EMG detector 945 by communicating with the TMS brain stimulation device 925, where such devices are not physically integrated.

It is presently anticipated that combinations of parameters including a theta burst pulse frequency in the range of 12 to 40 Hertz and a burst repetition frequency of 3 to 8 Hertz would be the range of primary focus, and especially the range including a theta burst pulse frequency of between 16 and 28 Hertz and a burst repetition frequency of 4 to 7 Hertz would be part of the parameter search area, for reasons described in more detail later herein. Preferably, a short-burst pulse pattern involving less than 100 pulses, and more preferably less than 20 pulses in total, would be used for the search pattern, with adequate stabilization time between each test pattern. Different search routines may be employed. For example, a search routine may start with the parameter combination most likely to be successful (e.g., 20 Hertz pulse frequency), or else may be designed to examine a set of test points and then use interpolation to converge on the most optimal combination of parameters. The search routine may also be designed to search along pulse/burst frequency ratio lines that have previously met with success, and in particular search within the range of pulse/burst frequency ratios of 3 and 5, for reasons explained in more detail later herein.

As the search routine cycles through different combinations of pulse parameters, the patient's EMG response (or other biological response) is recorded by the computer 906 and may be stored in association with that patient's records for later analysis. The computer 906 may evaluate the patient's response to determine the set of parameters that lead to the maximum inhibitory or excitatory response, depending on the nature of the treatment, and display this information on the screen 903 for evaluation by the physician or other operator. The physician or operator may thereafter elect to use the parameter combination that has been found by the search routine, or else to manually override that parameter combination with other parameters. The physician or operator may then, via the user interface 986, instruct the computer 906 to save and store the optimal parameters for the particular patient in the durable memory area 910, in a record associated with the particular patient 950, for later use in treatments for the patient 950.

The search routine as described above is made possible by a number of inter-related discoveries disclosed herein. A first is that different pulse and burst frequency combinations have a material impact on the patient's neurological response, and hence on the efficacy of TMS therapy treatments, and that this impact can be measured and quantified using a biological sensor such as an EMG detector. A second discovery is that particular pulse and burst frequency combinations (e.g., pulse frequency between 12 and 40 Hertz, and more preferably between 16 and 28 Hertz) yield substantially more effective results for TMS, and those results can either be inhibitory or excitatory in nature depending upon the particular combination of parameters. A third discovery is that TMS pulse sequences with a relatively small number of pulses (which can be in the range of 6 to 20 pulses, for example) can provide a significant enough neurological reaction such that the patient's response to parameter combinations can be determined or estimated using only a small pulse burst. This means that sample or test pulse patterns can be delivered in a relatively short amount of time, in a safe and effective manner, yet the patient's reaction to the parameter combinations used for those test patterns can be readily determined or projected. The combination of these discoveries enables the possibility to use automated or semi-automated search routines to hone in on a set of optimal parameters that are tailored to a given patient 950.

FIG. 2A-2B is a more detailed functional block diagram of a particular example of a therapeutic brain stimulation system 200 in accordance with the concepts illustrated in FIG. 1 and/or FIG. 9, and is broken down into sub-figures 2-A and 2-B. The therapeutic brain stimulation system 200 in this example is designed to deliver TMS pulses according to predetermined therapy regimens 229 stored in a durable memory area 225 of the system 200, in a manner similar to explained with FIGS. 1 and 9. Although various functional blocks are depicted in FIG. 2A-2B, the association thereof in particular physical hardware is not critical, and they may be implemented in a one or more devices constructed to generate and administer artificial TMS stimuli. Also, not all of the features depicted in FIG. 2A-2B are necessary to utilizing the predetermined therapy regimens 229 in a TMS stimulation system. The various components and features of the therapeutic brain stimulation system 200 in FIG. 2A-2B may be operated to perform similar functions to those described with respect to FIGS. 1 and 9, including selection of one or more predetermined therapy regimens 229 for treatment for a given patient, and/or using search routines to determine optimal combinations of TMS parameters for a given patient.

The therapeutic brain stimulation system 200 may include one or more brain stimulation devices and, in this particular example, includes two brain stimulation devices 206, 208, which are preferably TMS devices or other noninvasive electromagnetic brain stimulation devices. Each of the brain stimulation devices 206, 208 may be powered by its own dedicated power source 204, 210 respectively, which may each be a 110 volt, 15 amp power source (or other power source tailored for the standard power supply in a particular geographical location). A patient may receive electromagnetic stimulation from either or both brain stimulation devices 206, 208. Each brain stimulation device 206, 208 has its own respective servomotor 220, 222, for positioning each device 206, 208 about the patient's brain. Each servomotor 220, 222 may be positioned about a 64 lead TMS-compatible EEG cap or other neurophysiological measurement device 218. Each servomotor 220, 222 may be communicably coupled to neuronavigation equipment such as an infrared neuronavigation camera 212 and neuronavigation component 214. The neuronavigation component 214 may receive functional, structural, and probabilistic stimulation targeting input 226 by way of real-time swLoreta processing 228; digitized MRI or other brain imaging input for neuronavigation and calibration of data, as illustrated by box 224 in FIG. 2A-2B; and cordance analysis 290. The real-time swLoreta processing unit 228 may be in communication with a computer 282.

The computer 282 may be in communication with a keyboard 284 and computer printer 286, either or both of which may be wireless in nature. Computer 282 may also be in communication with a video monitor for a computer operating system 280; a video monitor for real-time cordance QEEG brain mapping, real-time swLoreta imaging, real-time power spectrum graphing, and ongoing raw EEG activity using preferred montage, as per box 278; and a video monitor for real-time neuronavigation imaging of coil position and orientation with reference to a patient's brain anatomy using digitized personal MRI or other brain imaging study, as per box 276. Computer 282 may also be in communication with an amplifier 266, an analog to digital converter 268, a band pass filter 270, a notch filter 272, and an artifact removal component 274. Computer 282 may be in further communication with a spectroscopic analysis component 288 and a module 295 for coordination of brain stimulation treatment using multiple stimulation devices, such as devices 206, 208. Module 295 may receive input including EMG to measure abducens pollicis brevis ("APB") or first dorsal interosseus ("FDI") muscle contraction to determine MT, as per box 262; and scalp, temperature, pressure, and distance sensors, as per box 264. Spectroscopic analysis component 282 may be in communication with cordance analysis 290, which in turn may involve MT percentage, as per box 250.

Module 295 may be in communication with sensory stimulation device 216 for providing supplemental stimulation (e.g., audio such as music) as previously described. The module 295 may also draw upon the parameters to be utilized for therapy for the patient, which may either be retrieved and selected from the prestored therapy regimens 229 in a durable memory area 225 (as may be associated with the computer 282 for example, or either of the brain stimulation devices 206, 208), and may thereby obtain parameters for TMS or other burst therapy such as the motor threshold (MT) percentage 250; pulse frequency 248; stimulation timing 246; intertrain interval 244; stimulation interval (i.e., burst repetition frequency interval) 242; total number of pulses per session 240; if burst stimulation, then number of pulses per burst 238; pulse waveform shape 234; multi-device combinations including sequential, interleaved, simultaneous, or multimodal 232; and sensory stimulation parameters 230, which are used to configure the secondary or supplemental sensory stimulation device 216. Spectroscopic analysis component 288 may also affect the delta power spectrum 258 including the delta band power spectrum and the alpha peak 260, which are involved with stimulation training 246 and frequency 248, respectively.

The computer 282 may also be involved with an individualized diagnosis-specific treatment protocol plan and record, as per functional block 254, which may in turn be in communication with a printer for treatment records. Computer 282 may also be in communication with a pre-seizure detection component 256.

The pre-seizure detection component 256 may optionally include a dynamic pre-seizure activity feedback system where real-time EEG is analyzed continuously and monitored for escalating clustered spike activity using a computerized seizure detection monitoring algorithm. In one embodiment, if pre-seizure activity is detected, then its principal focus is automatically calculated and the coil is moved immediately to that location. Pulse parameters then immediately change to continuous 1 Hz inhibitory treatment at 100% of the patient's MT as measured by monitored spike activity density. The treatment chair may then be automatically moved to a position nearest the floor to minimize possible trauma from a fall if a seizure does occur. Bilaterally, armrests are raised to an elevated position to keep the patient in the chair if the patient becomes unconscious. Finally, the chair is reclined until the patient is in a supine position to protect the patient in case of a seizure. A warning bell is activated both locally in the treatment room and remotely at the front desk of a clinic to notify staff of possible impending seizure activity. If the spike density does not decrease after 5 seconds of inhibitory TMS treatment, MT % is increased at 5% intervals until spike activity begins to diminish. When preictal spike activity begins to diminish, one Hertz inhibitory stimulation is maintained at current MT intensity percentage until preictal spike activity vanishes. At that point, the coil arm is withdrawn, armrests are automatically lowered, the patient chair is elevated to a seated position so the patient may be evaluated by a treatment team, and the active treatment system is shut down but ongoing real-time EEG activity continues to be displayed on a screen to aid the treatment team in evaluating the patient's condition. If EEG spike activity moves from preictal to ictal and the beginning of a seizure is detected by the system, the coil arm is immediately withdrawn, and a more urgent auditory and visual alarm is triggered and emergency personnel are automatically called to the scene if the emergency procedure is not countermanded by staff. To prevent aspiration of mucus or vomit, the chair automatically tilts slightly by 15 degrees and the head rest rotates to turn the patient's head to the side in the direction the chair is tilted. The treatment chair arm on that side is further extended to give additional protection from falling in that direction. After the EEG cap is removed, the device automatically prints out a full report including EEG activity, pulse parameters, patient's treatment history, medication, etc. for reference for emergency personnel either on site or at the emergency room.

The therapeutic brain stimulation system 200 may be operated in a similar manner as previously described for FIG. 9, in order to deliver selective therapy regimens from among a set of prestored therapy regimens 229, and/or to cycle through the prestored therapy regimens 229 or employ some other search routine in order to determine optimal combinations of parameters for a given patient, preferably using short-burst pulse sequences of less than 100 pulses and, more preferably, less than 20 pulses. The EMG detector 262 may be utilized to monitor patient response and provide feedback to the brain stimulation system 200, and in particular to module 295 and/or computer 282, to facilitate the search routine and provide useful measurement information in order to determine whether the patient is more or less responsive to a given set of pulse parameters.

It should be noted that the systems of FIGS. 1, 2A-2B, 7 and 9 are not limited to providing therapies to treat a neurologic or psychiatric disorders that are experienced by a patient, but may also be used for enhancement of cognitive, motor, social, or psychological skills.

FIG. 3 is a flow chart illustrating a process 300 for selecting theta burst parameters for a given patient in accordance with one or more embodiments disclosed herein, in order to, e.g., treat neurologic or psychiatric disorder or for enhancement of cognitive, motor, social or psychological skills, as may be used in connection with any of the systems illustrated in FIGS. 1, 2A-2B, 7 and/or 9, for example. Although FIG. 3 is particularly focused on TMS therapy, a similar process may be used with other brain stimulation techniques, according to conventional protocols.

The process 300 of FIG. 3 starts with step 302, in which an EEG cap, such as cap 218 illustrated in FIG. 2B, is fitted onto the patient's scalp. The cap may have, for instance, 64 leads for taking measurements over the brain area. In a next step 305, infrared detectors may be attached on the front of the cap in the forehead area. Then, in a following step 310, external landmarks may be located, and the cap adjusted on the patient's cranium such that referenced distances from nasion, inion, and both pre-auricular spaces are in accord with the patient's individual reference values. Step 310 may further involve marking certain target areas, such as the LDLPFC and/or RDLPFC target locations. As but one example, this may be done by marking target location at the Brodmann Area 46/9 border at the middle third of the middle frontal gyri on the digitized MRI, and then instructing the system to record Talairach coordinates of the LDLPFC target. Then the RDLPFC target location may be marked on the digitized MRI, followed by instructions to the system to record Talairach coordinates of the RDLPFC target. Other areas of the brain, such as Brodmann Area(s) 22 or 25, may be located also in this manner.

Although not expressly shown in FIG. 2A-2B, after step 310 further pre-treatment preparations may be made prior to delivery of the stimulating pulses. For example, one such activity is setting the dynamic freedom of movement for the coil positioning system. In particular, the dynamic coil position may be activated to orient the servomotor feedback system so that the calculated E-field intensity is maintained at maximal value in the center of target volume Talairach coordinates, and the coil's position and orientation moves 5 in real-time to maintain coil contact and orientation as the patient's head moves. Similarly, a dynamic coil temperature comfort maintenance system may be calibrated or configured. Here, a dynamic coil temperature feedback system is activated so a coil temperature reading is taken periodically (e.g., every 15 seconds) and graphed continuously over time. A best-fit curve is fitted to the data points and extended until the projected end of the treatment session. If projected temperature versus time trajectory reaches a best-fit curve where the temperature is calculated to exceed a threshold (such as 41 degrees Celsius), then the intertrain interval is automatically extended by intervals of one second until the projected best-fit curve does not exceed the temperature threshold. The intertrain interval value at that point is continued for subsequent pulse trains unless the projected temperature is again seen to rise above the threshold (e.g., 41 degrees Celsius), at which point the procedure is repeated.

Another preparatory step may involve calibrating or configuring a dynamic scalp comfort maintenance system. In particular, a dynamic scalp pressure feedback system may be activated so the patient's recorded preferred scalp contact pressure is maintained in real time without discomfort and measured in 100 millisecond intervals until 100 microseconds before a magnetic pulse is scheduled to fire. At that point, the measurement interval decreases to 1 microsecond intervals beginning 50 microseconds before pulse discharge, and the coil positioning system is switched to piezoelectric feedback system for 100 microseconds before pulse, 200 microseconds during pulse and 100 microseconds after pulse discharge, maintaining scalp pressure within desired target range. At 100 microseconds after magnetic pulse, the coil positioning system is taken over by servomotors until next magnetic pulse. The dynamic scalp distance feedback system may be set so that the coil face is never greater than a threshold distance, usually 1 mm, as measured by three micro-laser measuring devices embedded in the coil face. If the exceeds threshold distance from the scalp, either servomotor or piezoelectric positioning systems will be activated to close the distance. At the same time, a real-time feedback system is ongoing to keep an initial targeted ratio of three distance measurements constant so the coil is stable in all three rotational degrees of freedom if the infrared tracking system is unable to determine three-dimensional rotational position changes to the accuracy necessary to keep max E-field continuously at the target location.

Also, a dynamic pre-seizure activity feedback system may be activated, whereby real-time EEG is analyzed continuously and monitored for escalating clustered spike activity using a computerized seizure detection monitoring algorithm. If pre-seizure activity is detected, its principal focus is automatically calculated and the coil is moved immediately to that location. Pulse parameters then immediately change to continuous 1 Hz inhibitory treatment at 100% of the patient's MT as measured by monitored spike activity density. The treatment chair is automatically moved to a position nearest the floor to minimize possible trauma from a fall if a seizure does occur. Bilaterally, armrests are raised to an elevated position to keep the patient in the chair if the patient becomes unconscious. Finally, recline the chair until the patient is in a supine position to protect the patient in case of a seizure. A warning bell is activated both locally in the treatment room and remotely at the front desk of a clinic to notify staff of possible impending seizure activity. If the spike density does not decrease after 5 seconds of inhibitory TMS treatment, MT % is increased at 5% intervals until spike activity begins to diminish. When preictal spike activity begins to diminish, one Hertz inhibitory stimulation is maintained at current MT intensity percentage until preictal spike activity vanishes. At that point, the coil arm is withdrawn, armrests are automatically lowered, the patient chair is treatment team, and the active treatment system is shut down but ongoing real-time EEG activity continues to be displayed on a screen to aid the treatment team in evaluating the patient's condition. If EEG spike activity moves from preictal to ictal and the beginning of a seizure is detected by the system, the coil arm is immediately withdrawn, and a more urgent auditory and visual alarm is triggered and emergency personnel are automatically called to the scene if the emergency procedure is not countermanded by staff. To prevent aspiration of mucus or vomit, the chair automatically tilts slightly by 15 degrees and the headrest rotates to turn the patient's head to 30 the side in the direction the chair is tilted. The treatment chair arm on that side is further extended to give additional protection from falling in that direction. After the EEG cap is removed, the device automatically prints out a full report including EEG activity, pulse parameters, patient's treatment history, medication, etc. for reference for emergency personnel either on site or at the emergency room.

Returning to FIG. 3, in a next in step 315, the neuronavigation device (such as 214 in FIG. 2A-2B or 935 in FIG. 9) may be used to navigate to the target treatment area. This may involve, among other things, activation of a real-time video display of three-dimensional coil position referenced to brain anatomy by the neuronavigation device, and calibration of the neuronavigation system. As part of this process, the patient may be asked to sit in the chair and use any automatic controls to adjust the chair until the patient feels comfortable. With the EEG cap in position, the neuronavigation system may be calibrated using images from the infrared neuronavigation camera, such as from camera 212 shown in FIG. 2A-2B, with the three-dimensional cluster of various infrared reflectors, such as infrared reflectors located on the EEG cap, coil, reference pen, and coil calibration board. Following this process, the coil(s) may be placed in appropriate position, as indicated by step 320.

In a next in step 320 of FIG. 3, a test sequence of pulses is initiated in order to confirm proper placement of the coil(s). Step 325 may therefore involve pre-treatment QEEG measurements. For example, in step 320, the system may be used to perform a short (such as one minute long) resting eyes-closed baseline QEEG and find the location of maximum weighted intensity of theta band activity in the region of interest. Then the anterior, pregenual, and subgenual cerebral cortex locations may be analyzed, and their locations marked on the digital brain image as the target. Step 20 may also involve calculation of the weighted cordance value in the region of interest and recordation of the target Talairach coordinates and weighted average cordance value in the patient's data file. Then the system can further be used to display the patient's theta band swLoreta superimposed on the patient's digitized MRI on one side of a split-screen EEG video monitor, while the patient's cordance brain maps is displayed on the other side of the split-screen EEG video monitor. As a result of this process, in step 328, adjustments may be made to the positioning of the coil(s).

In a next step 330, a motor threshold (MT) value may be determined, which may be used to set the amplitude of stimulating pulses that will be delivered to the patient as part of the brain stimulation therapy. A prior motor threshold value may also be used. However, a new motor threshold value may be advisable if, for example, (1) the last measured MT was not obtained in the past week, (2) there is a new medication change, (3) the patient is sleep deprived, or (4) the patient has had caffeine before the procedure. A new MT reading may be obtained by using a dynamic electromyography system that (1) measures electrical activity in the patient's contralateral APB or FDI muscle after single pulse TMS treatment over the motor cortex and (2) graphs pulse location with muscular contraction intensity as measured by EMG on neuronavigation reconstruction of motor cortex surface anatomy. After the patient is comfortable and EMG electrodes are placed over the APB muscle of the contralateral hand, the system is instructed to perform a MT determination on one or both sides depending on laterality of treatment target locations. The process begins by placement of a TMS coil over the projection of the hand knob of the motor cortex on the appropriate side for measurement. A test pulse of moderate intensity is triggered by the system after the coil is in place. The EMG value is recorded by the system. The coil is then moved 0.5 cm parallel to the axial plane and the procedure is repeated at a new location while the pulse intensity is held constant. The procedure is then repeated by the system by moving the coil position 0.5 cm parallel to the coronal plane.

The procedure continues automatically in a grid pattern of stimulation points with a distance of 0.5 cm between points until a 3 cm by 3 cm grid search pattern has been performed on the cortical surface with the center over the anatomic landmark initially marked on the MRI. The Talairach coordinates of the cortical surface anatomy in three-dimensional space are superimposed on the APB contraction strength at each point represented by a scalar quantity in the region stimulated for the MT. The surface represented by a best-fit approximation created by a mesh is constructed and the local maxima and minima are calculated and marked digitally on the surface of the patient's brain. In other words, mark the point where the second derivative of the derived surface mesh is zero, and if there are multiple points fulfilling this requirement, the point is chosen that has the largest associated scalar quantity. The system then runs an algorithm of pulses at that location and measures the EMG response while coil stimulation intensity is now varied while the spatial location is held constant. After repeated measurements, the system determines the approximate coil intensity that triggers a thumb twitch of greater than 50 microvolts 50% of the time and a thumb twitch of less than 50 microvolts amplitude 50% of the time. Alternative methods for determining motor threshold may also be used, and any reliable method can be used with the embodiments disclosed herein.

After step 330, the next step 340 is to select a therapy regimen, from among a set of prestored therapy regimens, to apply to the patient, or to alternatively select a manual set of parameters if none of the prestored therapy regimens are suitable. Step 340 may alternatively involve, especially for first-time patients, a search process as previously described in connection with FIG. 9 for determining optimal individualized stimulation parameters for the particular patient. Further details relating to step 340 are described in relation to the process of FIG. 6 hereafter.

In a following step 343, a secondary stimulation technique, and particularly a sensory stimulus such as audio (e.g., music) or tactile stimulation, may optionally be added to the therapy, to be used concurrently or in conjunction with the pulse stimulation therapy. Then in step 345, the pulse stimulation therapy is commenced, in coordination with the sensory stimulus if applicable. In particular, the parameters selected from the prestored therapy regimen, or manual entry of parameters, in step 340 are loaded and used for delivery of stimulating pulses.

In a next step 350, the therapy is concluded and the patient's cap removed. Data relating to the therapy session may be recorded and used for later analysis and treatment. In any of the foregoing steps of the process in FIG. 3, the therapeutic brain stimulation system may employ techniques described in copending U.S. patent application Ser. No. 13/768,819 filed on Feb. 20, 2012, published on Feb. 27, 2014 and assigned Pub. No. US20140058189A1, by the same inventor thereof, hereby incorporated by reference as if set forth fully herein.

FIG. 6 is a flow chart illustrating a process 600 for selecting theta burst parameters from among a set of predetermined parameters, as may be used, for example, in connection with the therapeutic brain stimulation system(s) illustrated in FIGS. 1, 2A-2B and/or FIG. 9, and in connection with the process described above for FIG. 3. In particular, the steps of FIG. 6 may be employed in connection with the process step 340 in FIG. 3. In FIG. 6, a first step 630 may involve determining a motor threshold based upon the measurements received during initial pretreatment EEG monitoring, or else from a pre-stored motor threshold value for the particular patient. In a next step 635, one or more predetermined therapy regimens 686 from set 685 of regimens may be retrieved from a durable memory area 680 and displayed in a manner so that the physician, clinician or other operator can view the information in sufficient detail so as to make an informed selection of one of the predetermined therapy regimens 686. Each of the predetermined therapy regimens 686 from the set 685 may include a number of different therapy parameters, but need not include all possible parameters. Such parameters may include those listed previously, such as motor threshold (MT) percentage, pulse frequency, stimulation timing, intertrain interval, stimulation interval (i.e., burst repetition frequency interval), total number of pulses per session, and if burst stimulation, then number of pulses per burst, pulse waveform shape, multi-device combinations including sequential, interleaved, simultaneous, or multimodal, and sensory stimulation parameters, which can be used to configure the secondary or supplemental sensory stimulation device.

By way merely of example, the predetermined therapy regimens 686 in FIG. 6, or in any of the other described embodiments, may include one or more of the 5/16/3, 5/20/3, 6/20/3, 20/20/1, 5/22/2, 5/24/2, 6/24/2 or 7/28/2 patterns discussed later herein (where 5/16/3 signifies a burst repetition frequency of 5 Hz, a pulse frequency of 16 Hz, and a number of pulses per burst of 3), in conjunction with any other stimulation parameters as desired. Furthermore, the predetermined therapy regimens 686 may include specific sets of stimulation parameters that have been customized, through measurement, search routine, or other techniques, for an individual patient and stored in a manner associated with the respective patient, to facilitate retrieval and use for that patient at a later time. For example, an operator may, through a user interface of the therapeutic stimulation system, enter a command that causes the system to store a new predetermined therapy regimen 686 for later use, in association with identifying indicia (such as a patient ID number or name) that relates the predetermined therapy regimen 686 to the particular patient.

As they are displayed, the user may cycle through the therapy regimens 686, depending on how many there are, and in step 637 select one of the predetermined therapy regimens 686 for use in the current therapy session. In response to the user selection, in step 640 the parameters from the selected predetermined therapy regimen 686 may be loaded into the portion of the brain stimulation device responsible for timing and generation of pulse stimulation commands. For example, from the selected predetermined therapy regimen 686, the system may set the pulse frequency 642, set the burst repetition frequency 643, set the number of pulses per burst 644, set the length of a burst train (for example, the number of bursts per train or time corresponding thereto) 645, set the number of trains (or alternatively the number of total pulses in the treatment), and the inter-train interval 647. These settings may be in terms of any convenient units, and may for example be shown in terms of frequency (Hertz), time (seconds), pulse counts, or ratios relative to other parameters (such as pulse/burst frequency ratio). In a next step 660, the timers and counters (whether software or hardware) used to time the relevant intervals are loaded, as is done with conventional pulse delivery systems using entirely manual parameter selection.

In a next step 665, the pulse amplitude is selected, preferably based upon the determined motor threshold in step 630. This may be done automatically or manually. Further, step 664 may also include selection of other aspects of the pulses, such as waveform shape, polarity, or polarity pattern. These selections can either come from the predetermined therapy regimens 686, or may be manually selected, if available. Then in step 670, the stimulation therapy treatment is initiated.

Figure 4A:
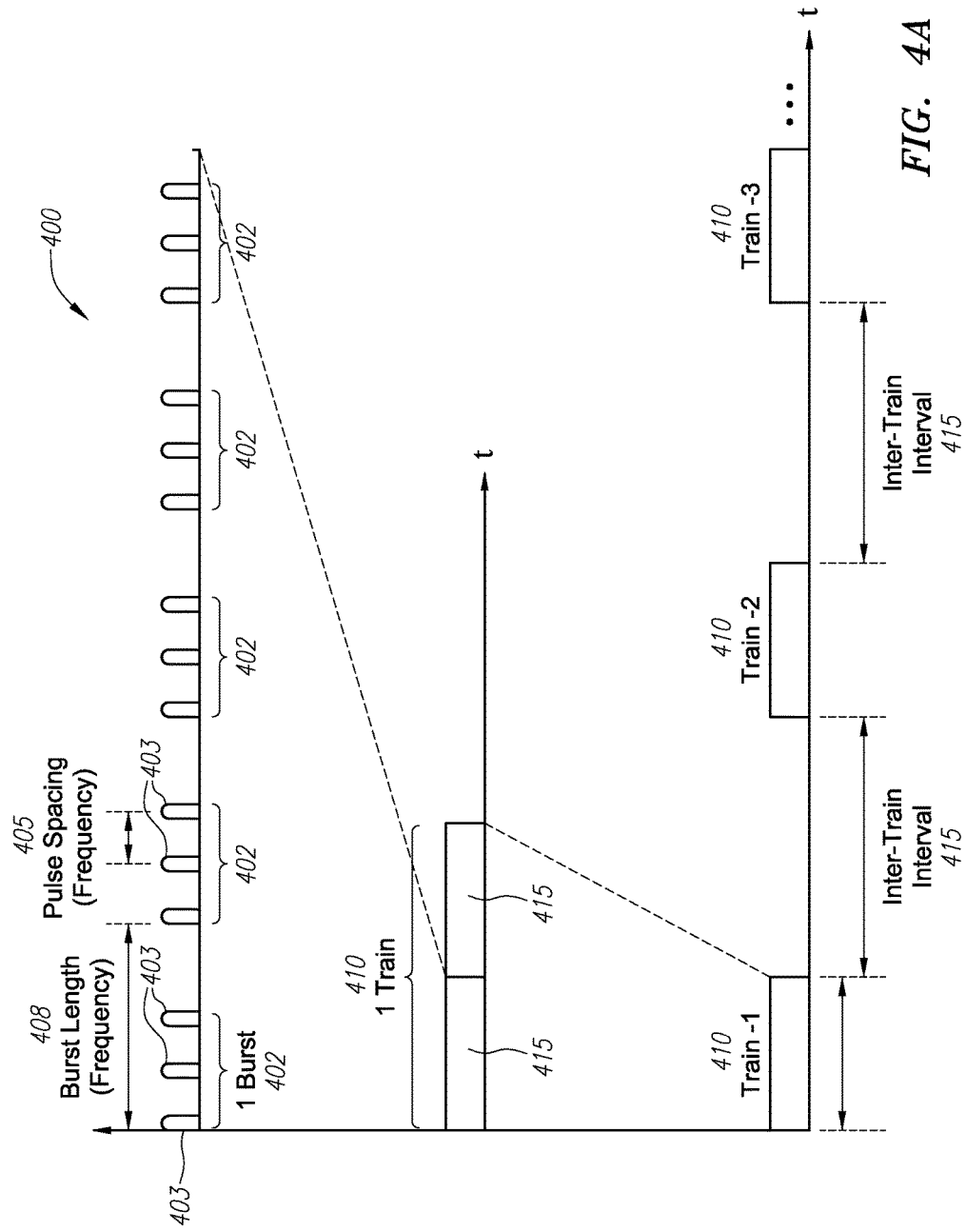
FIG. 4A is a timing diagram showing a timing pattern of electromagnetic pulses administered as part of a therapeutic brain stimulation therapy according to one or more embodiments as disclosed herein.

FIGS. 4A, 4B, 5, and 10A-10E are diagrams illustrating different patterns of electromagnetic pulses administered as part of a therapeutic brain stimulation therapy according to one or more embodiments as disclosed herein, and provide further insight into some of the novel aspects of the burst protocols that are described herein. FIG. 4A is a timing diagram illustrating an example of a pattern of artificial stimuli as may be applied, for example, in connection with an intermittent theta burst stimulation (iTBS) protocol as used in connection with TMS therapy. In FIG. 4A, a sequence of pulses is delivered in a set of trains 410 over a period of time, with the trains 410 identified sequentially as Train-1, Train-2, Train-3, and so on. Each train 410 comprises a set of pulses, and the total number of trains therefore determines the number of total pulses delivered in a session. Each train 410 in this example is identical, and comprises a number of bursts 402. For convenience, each train 410 may conceptually be broken into a number of sections 415, in this case two equal sections 415 each constituting a prescribed time period (such as one second). Each section 415 in this example involves five bursts 402. Each burst 402 in turn has a number of pulses 403, in this example three pulses 403. Thus, in the example of FIG. 4A, each pulse train 410 has ten bursts 402 and comprises a total of 30 pulses 403.

FIG. 4A also indicates certain relationships among the parameters used in a burst therapy. The burst length 408 is related to the burst frequency. For example, a burst length 408 of 200 milliseconds would correspond to 5 Hertz, and of 250 milliseconds would correspond to 4 Hertz. The pulse spacing 405 relates to the theta frequency or pulse frequency. For example, with a pulse frequency of 50 Hertz, the pulse spacing 405 would be 20 milliseconds, and with a pulse frequency of 20 Hertz, the pulse spacing would be 50 milliseconds. In addition, the inter-train interval 415 indicates the timing between pulse trains 410. The inter-train interval may also be expressed in terms of frequency of train repetition, which in turn indicates the timing between trains 410. The inter-train interval in such a case can readily be derived from knowing the duration of a pulse train along with the train repetition frequency.

Figure 4B:
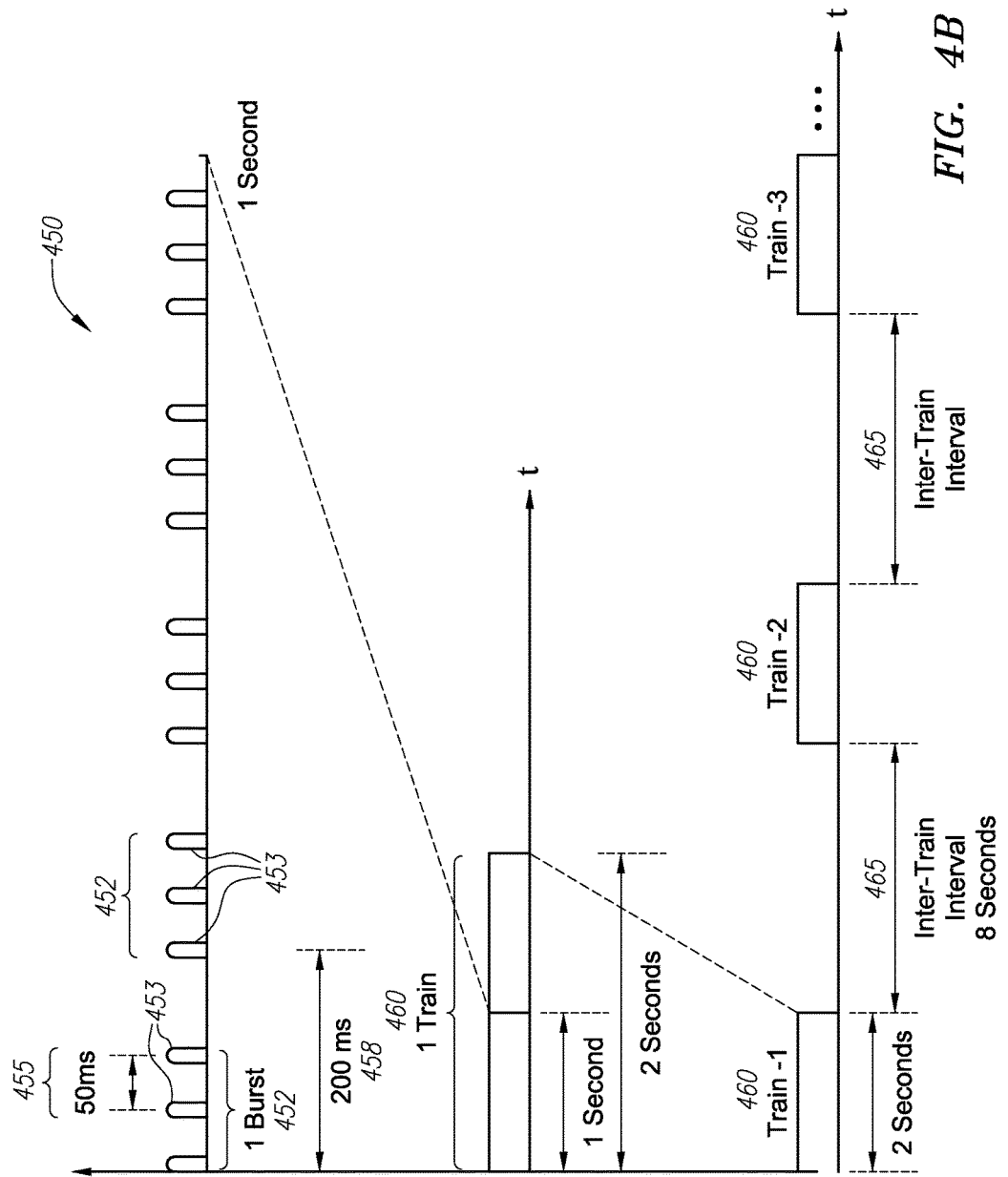
FIG. 4B is a timing diagram similar to FIG. 4A but identifying a more specific timing pattern in accordance with a preferred embodiment as disclosed herein.

FIG. 4B is a timing diagram similar to FIG. 4A but identifying a more specific timing pattern in accordance with a preferred embodiment as disclosed herein. In FIG. 4B, a pulse stimulation pattern is illustrated involving a pulse frequency (or theta frequency) of 20 Hertz, a burst repetition frequency of 5 Hertz, a number of pulses per burst equal to three, a train length of 10 bursts (or two seconds), and an inter-train interval of 8 seconds (or train repetition rate of 0.1 Hertz or 10 seconds). The pulse frequency corresponds to a pulse spacing 455 of 50 milliseconds, the burst repetition frequency corresponds to a burst length 458 of 200 milliseconds, the number of pulses corresponds to a burst duration 452 of 100 milliseconds, the train length 460 corresponds to two seconds, and the inter-train interval 465, i.e., the amount of time from the end of one train 460 to the start of the next train 460, corresponds to 8 seconds.

Figure 5:
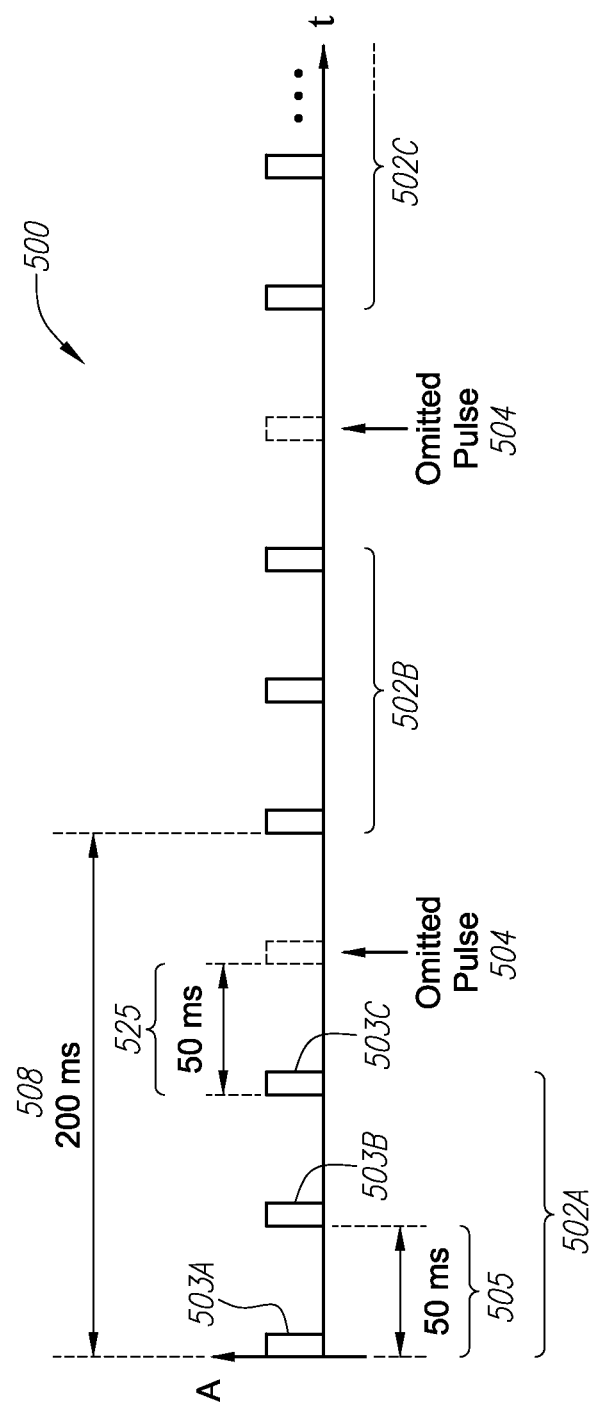
FIG. 5 is a timing diagram illustrating certain principles of operation of the therapeutic brain stimulation therapy such as provided by the timing pattern of FIG. 4B.

FIG. 5 is a timing diagram illustrating certain theoretical principles of the therapeutic brain stimulation therapy such as provided by the timing pattern of FIG. 4B. FIG. 5 illustrates a set of bursts 502A, 502B, 502*c* delivered during a pulse train. The first burst 502A comprises a sequence of three pulses 503A, 503B, 503C delivered at the start of a total burst duration 508 of 200 milliseconds, based on a burst repetition rate of 5 Hertz. As each of the pulses is separated by 50 milliseconds, the total duration of the three pulses is 100 milliseconds, following by 100 milliseconds until the next burst 502B of three pulses starts. Without intending to limit the invention in any regard, it is hypothesized that the "quiet" period from the last pulse 503C to the start of the next burst 502B represents an "omitted pulse" 504 that, as compared to a tonic sequence of 20 Hertz pulses for example, prevents the neurons from becoming de-sensitized to the stimulating pulses. The next burst 502B picks up with the same frequency stimulation timing. It is believed that this repetitive timing pattern, where the burst and pulse frequencies are selected so that one or more "omitted" pulses exist that would otherwise be at the same timing of the delivered pulses, leads to optimal pulse delivery results. Indeed, as described later herein, it appears that certain pulse/burst ratios having certain relationships (and specifically, being on the ratio harmonic line of 3, 4 or 5) may lead to particularly efficacious results in terms of stimulating therapies.

Figure 10A:
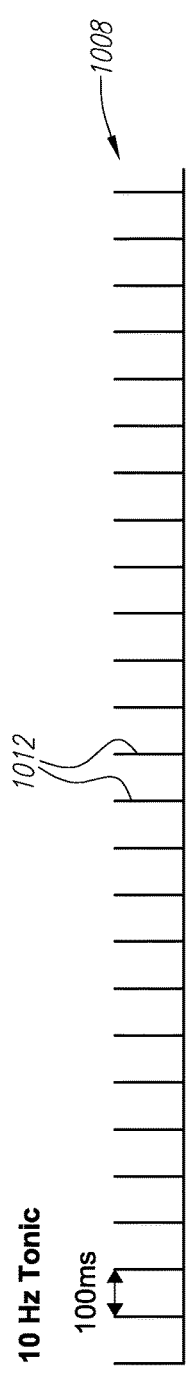
Figure 10B:
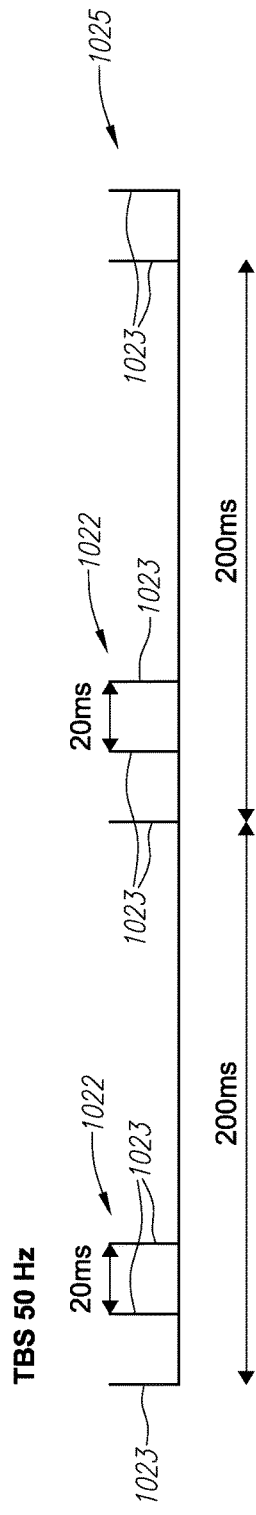
Figure 10C:
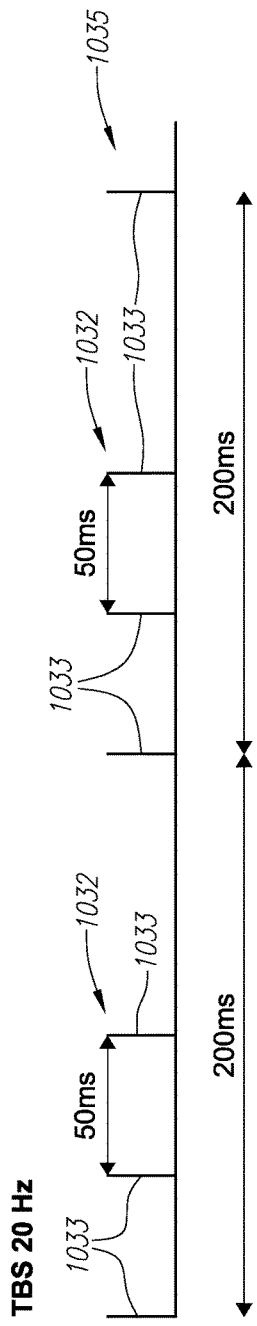
Figure 16A:
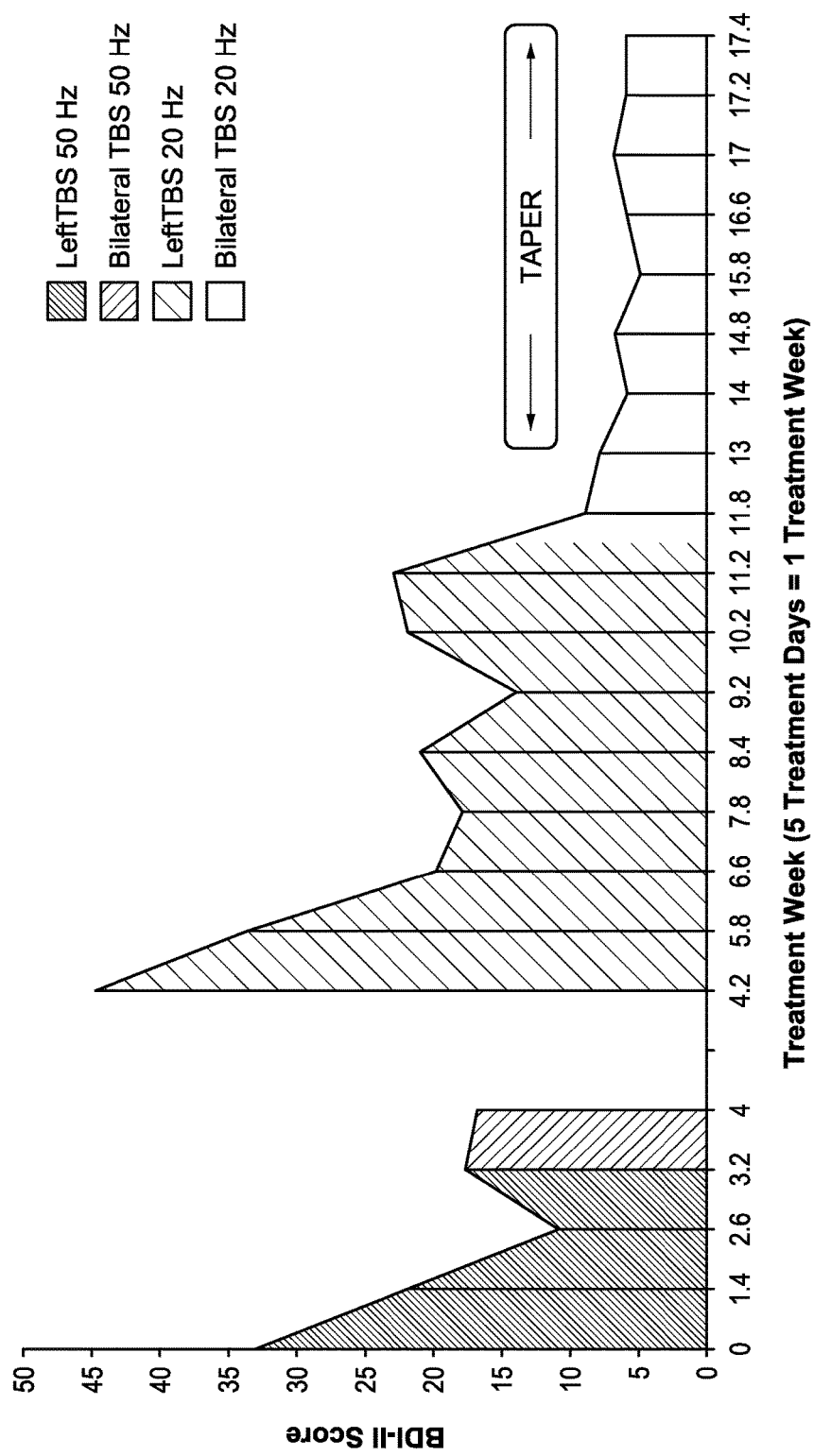
FIGS. 16A-16D are graphs illustrating over time how patients in the study group responded to treatments summarized in FIG. 14, in terms of BDI-II scale scores.
Figure 16B:
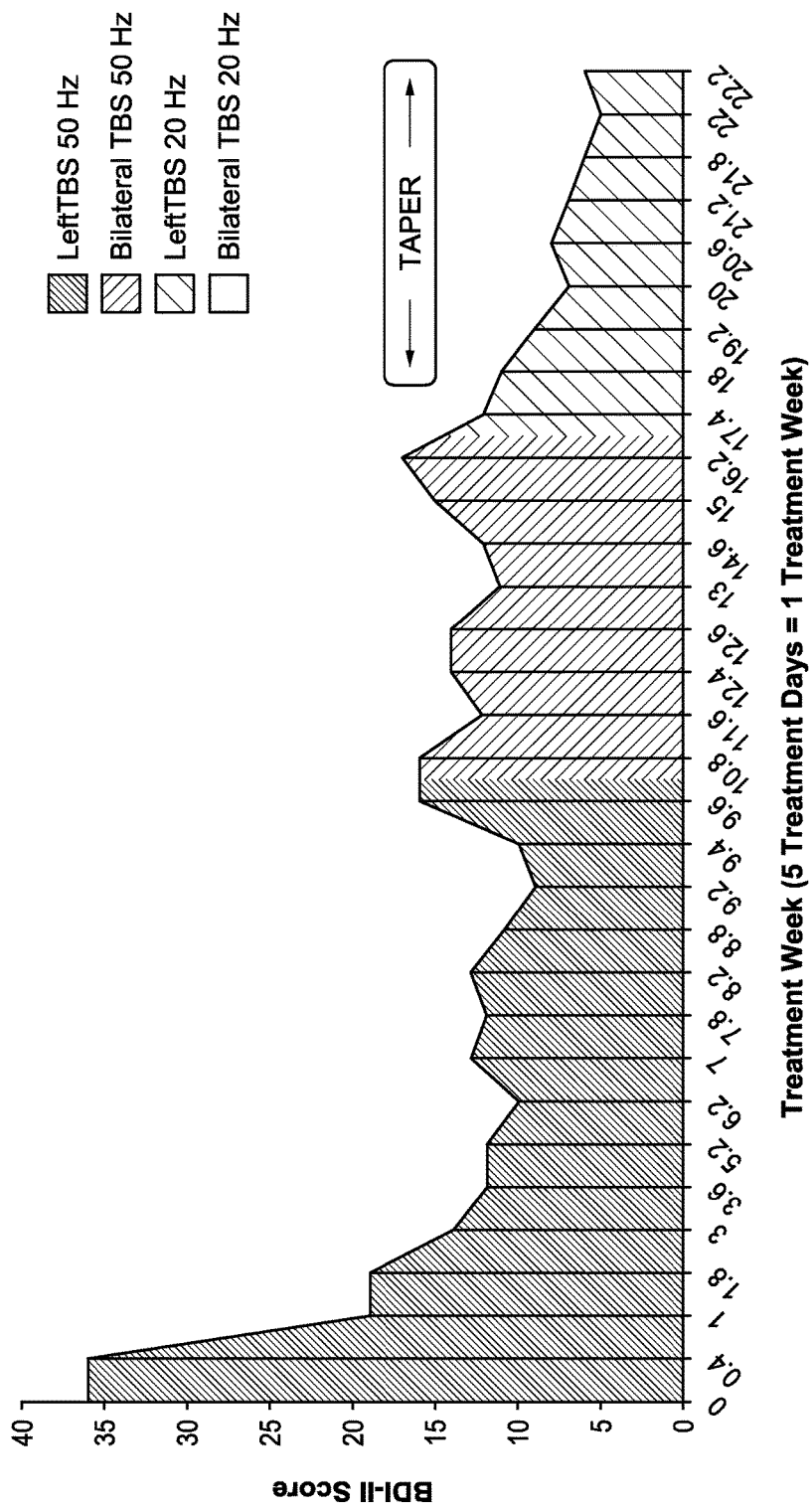
Figure 16C:
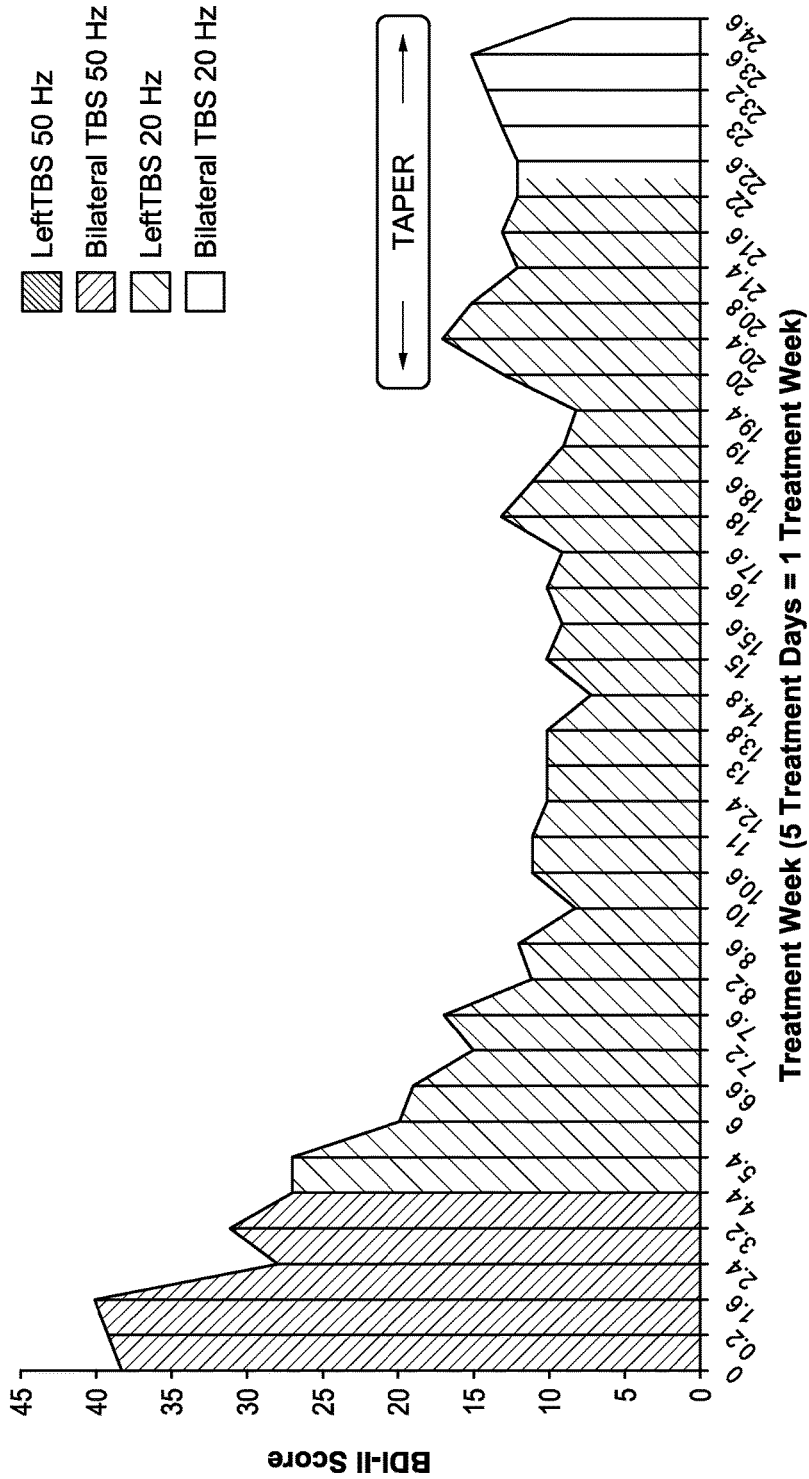
Figure 16D:
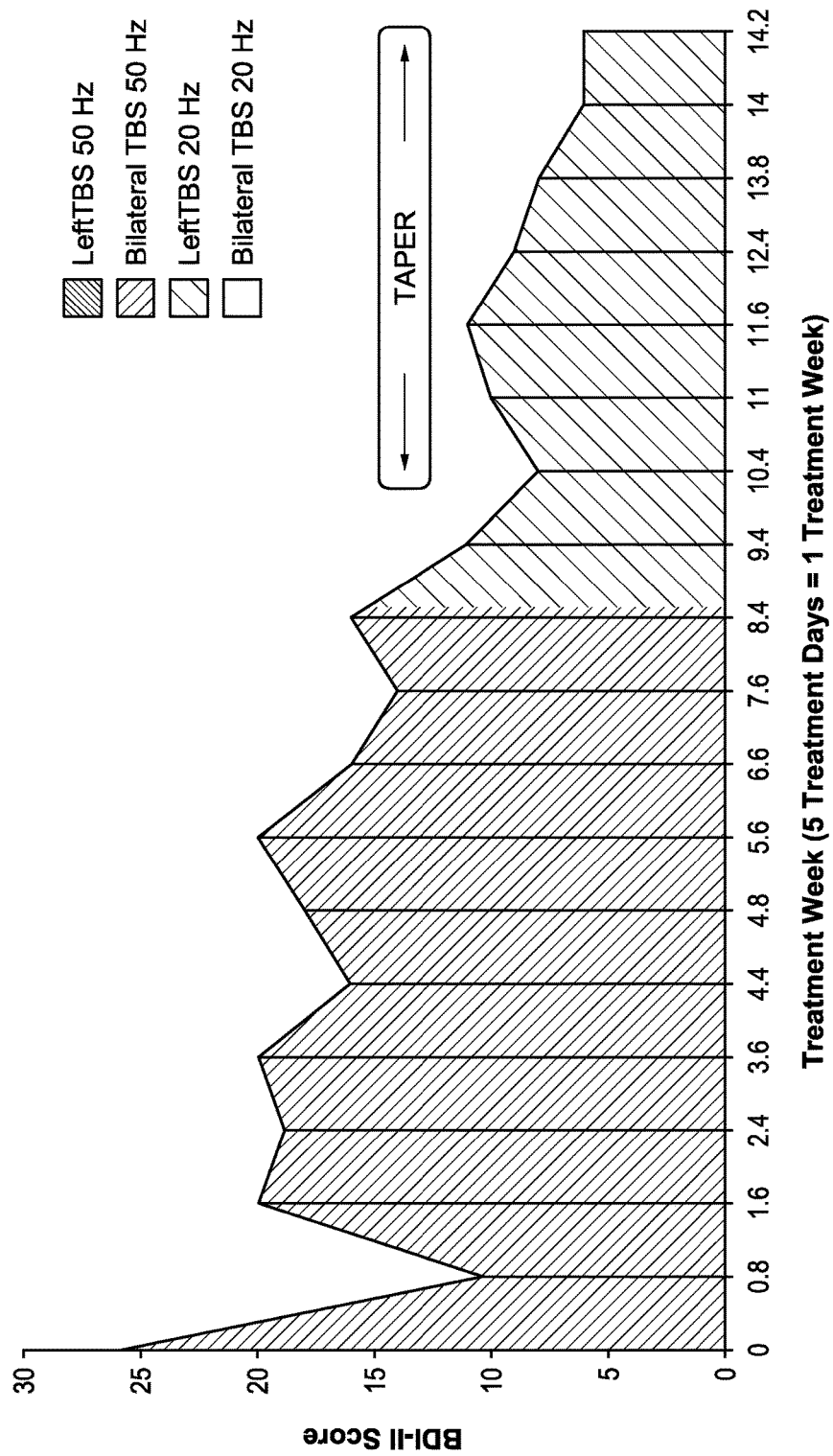

FIGS. 10A, 10B, 10C, 10D and 10E are waveform diagrams comparing delivery of TMS pulses employing tonic sequence and/or theta burst sequences of different frequencies. FIG. 10A illustrates a sequence 1008 of pulses 1012 delivered at a 10 Hertz tonic pulse frequency, leading to the pulses 1012 being separated at intervals of 100 milliseconds. FIG. 10B shows a theta burst sequence 1025 with a series of bursts 1022, each burst 1022 having three pulses 1023, delivered at a burst repetition frequency of 5 Hertz (corresponding to 200 milliseconds) and a pulse frequency of 50 Hertz (corresponding to a pulse spacing of 20 milliseconds). FIG. 10C is similar to FIG. 10B but with a pulse frequency of 20 Hertz. Thus, FIG. 10C shows a theta burst sequence 1035 with a series of bursts 1032, each burst 1032 having three pulses 1033, delivered at a burst repetition frequency of 5 Hertz (corresponding to 200 milliseconds) and a pulse frequency of 20 Hertz (corresponding to a pulse spacing of 50 milliseconds). FIG. 10D shows a pulse sequence 1045 involving a continuous train of pulses (cTBS), with a series of bursts 1042 delivered continuously over a long period (such as 240 seconds), with three pulses in each burst 1042. FIG. 10E illustrates a pulse sequence 1055 involving intermittent trains, with a stimulation intervals 1057 alternating with inter-train intervals 1058, similar to FIG. 4B although differing in the numbers of bursts per train. The train in this case applied during the stimulation intervals 1057 constitutes only two bursts 1052, each comprising three pulses. The stimulation intervals 1057 in this example are two seconds in duration, while the inter-train intervals 1058 are eight seconds in duration, so that the train frequency is 0.1 Hertz (corresponding to 10 seconds).

According to one or more embodiments, the transcranial magnetic stimulation device is operated to provide theta burst stimulation (TBS) according to prescribed parameters. For example, the transcranial magnetic stimulation device may deliver a burst of iTBS pulses at a theta (pulse) frequency in the range of 12 to 40 Hz, and more preferably a range of 16 to 28 Hz, and most preferably in a range of 19 to 21 Hz (where 3 pulses/burst are utilized) or 22 to 26 Hertz (where 2 pulses/burst are utilized), and at a burst frequency preferably in the range of 3 to 8 Hertz, more preferably in a range of 4 to 7 Hertz, and most preferably in a range of 5 to 6 Hertz. The iTBS pulse trains preferably are comprised of one to thirteen bursts, more preferably two to ten bursts, and most preferably four bursts, although they can be longer, and can be separated by an inter-train interval corresponding to a train repetition frequency of between 0.05 and 0.2 Hertz, although other timing patterns may be used. The iTBS pulses may be applied for an overall interval of time until effective, which may be as short as a few seconds in duration, or could be repeated over a duration of minutes. In various embodiments, the system may include a user interface for entering or selecting stimulation parameters for the theta burst pattern, and/or a durable computer memory for storing the stimulation parameters. The pulse generation controller may read the selected stimulation parameters and utilize them to deliver the selected theta burst pattern. The brain stimulation device is preferably a non-invasive one. The stimulation parameters may be selected with the goal of enhancing or suppressing neuroplasticity in the patient's brain. In a preferred embodiment, the brain stimulation device is a transcranial magnetic stimulation device operated so as to provide stimulating pulses directed to, for example, the patient's left dorsolateral prefrontal cortex (LDLPFC) or right dorsolateral prefrontal cortex (RDLPFC), or both, or another region of the brain.

2. Patient Studies

A study was conducted to assess the efficacy of the novel theta burst stimulation protocols disclosed herein, with particular focus on treatment refractory depression, although the techniques are believed to be widely applicable to a large number of neurological conditions and have efficacy for any type of condition presently treated using TMS therapy. It is known that TMS releases dopamine, and that dopamine mediates neuroplasticity. As neuroplasticity is critically involved in the pathology of depression, then it may be concluded that depression is connected to activation changes in the cingulate cortex (CC). Because the CC is linked via frontocingulate neural circuits to the LDLPFC, changes in neuroplasticity in that region, among others, may affect a patient's depression condition. Combining these facts, one aspect of the disclosed systems and methods herein is the recognition that TMS stimulation of the LDLPFC is a factor for enhancing neuroplasticity. Besides CC, other brain areas involved in neuroplasticity that may be measured to adjust stimulus parameters to maximize individual treatment efficacy include the frontal cortex, limbic system, amygdala, or hippocampus.

In connection with the patient study, four patients diagnosed with unipolar depression received TBS with triple pulsed bursts. The first three patients received TBS initially consisting of conventional theta TBS-50 Hz stimulation. However, during the theta 50 Hz phase of treatment, these patients failed to achieve remission although one patient had a positive response (that is, had a BDI-II reduction greater than 50%). New theta burst stimulation protocols were then developed consisting of a theta burst pattern around the range of 20 Hertz (TBS-20 Hz). Application of the TBS-20 Hz protocol surprisingly produced a profound improvement of patients' BDI-II scores. All four patients achieved full remission (BDI II≤10) with a mean decrease of 80% in their depression scale scores. Application of the TBS-20 Hz theta burst protocol was well tolerated by the patients and no adverse effects were noted during the course of treatment and taper. The results of this study support the safety and efficacy of the novel stimulus protocol and indicate that it should lead to a higher remission rate for treatment refractory patients than conventional TMS paradigms. Although the sample group was small, the remarkable consistency of results strongly supports the efficacy of the new TMS techniques, particularly when coupled with the fact that the patients initially showed a resistance to conventional TMS methods. In addition, the results were mathematically shown to be statistically significant with a high degree of confidence (over 99%).

Follow up investigation was then conducted to identify the range of theta burst frequency that provides superior results and to determine patterns or causes for the improvement. It was discovered that certain combinations of frequency and burst pattern provided much better response than the conventionally used TMS parameters. For example, it was discovered that three-burst patterns within a certain burst frequency range are substantially more effective for excitatory treatments, as compared to conventional methods, whereas two-burst patterns within another similar but not necessarily identical burst frequency range are substantially more effective for inhibitory treatments, as compared to conventional methods. These burst parameters are summarized in more detail later herein.

Without intending to limit the invention in any respect, it is presently theorized that the frequency ranges discovered in connection with the novel TMS treatments described herein are closer to the brain's natural frequencies used for neurological transmissions. Hence, the neurons become more responsive when artificially stimulated at these natural frequencies and produce a much more pronounced response. Conventional TMS methods have previously not focused on the brain's natural frequencies when establishing burst parameters. Thus, the discovery of the relation between artificial stimuli and the brain's response thereto, such that marked improvements are achieved, represents a significant advancement in the state of the art.

Patient studies supporting these results, in combination with other data, will now be described in more detail. The subjects were for patients with a long history of treatment refractory depression. All four patients had failed multiple anti-depressant medication trials. Baseline BDI-II scores were in the range of 26 to 44, indicating moderate to severe depression.

The patients were then treated with novel TMS techniques described herein. Patients initially presenting with severe anxiety symptoms began treatment with bilateral sequential theta burst stimulation treatment at a pulse frequency of 50 Hertz, while patients initially presenting without severe anxiety symptoms began with left dorsolateral pre-frontal cortex (LDLPFC) TBS-50 Hz. These patients were migrated to Bilateral TBS-50 Hz after failing to show remission or substantial improvement over a two-week period, and thereafter were advanced to different varieties of TBS-20 Hz regimens after failing to improve for two consecutive weeks, or after reaching a BDI-II Rating Scale Score of less than 10. FIG. 11 is a chart illustrating the sequence of theta burst treatment parameters for the study group. As can be seen from the chart, the therapies started with LDLPFC TBS-50 Hz for the first two patients, then progressed to bilateral sequential TBS-50 Hz, and then to LDLPFC TBS-20 Hz, with one of the two initial patients then progressing to bilateral sequential TBS-20 Hz. The last two patients began with Bilateral TBS-50 Hz, and both then advanced to LDLPFC TBS-20 Hz and, one of the two patients continued with bilateral sequential TBS-20 Hz.

FIG. 12 is a chart summarizing the number of treatment days spent by each patient in each of the protocols identified in FIG. 11. Total treatment days ranged from 51 to 103, with the average being 78 days. Typically, patients would be treated once or twice per day, five days per week. The number of treatment days in each therapy protocol should be sufficient from a clinical standpoint to determine the general efficacy of each applied protocol. Each patient also ended the treatment with an eight week taper schedule.

FIG. 13A-13B is a chart summarizing further information about the patients in the study group, including demographic information and clinical characteristics. The information in FIG. 13A-13B includes, among other things, the ages and genders of the patients, their diagnoses, the duration of their illnesses, the medications taken concurrently with the theta burst treatment, and their BDI-II Rating Scale scores.

FIG. 14 is a chart indicating more specifically the treatment protocols administered to the patient study group. In an effort to maximize efficacy of treatment, each patient received a series of treatment protocols that differed in stimulation frequency and laterality as depicted in FIG. 14. For the LDLPFC TBS-50 Hz stimulation treatment, a total of 4950 pulses were administered, with three pulses per burst at a frequency of 50 Hertz within each burst. The burst frequency itself, in all cases, was 5 Hertz. The total burst duration for each train of burst was 2 seconds, and the intertrain interval between burst trains was 8 seconds. The pulses were administered at 85-95% of the motor threshold. All treatments of LDLPFC were administered in combination with a secondary stimulus, in this case uplifting music chosen by each patient played during the treatment, to increase regional blood flow and enhance the TMS effects. The bilateral sequential stimulation involved a first treatment applied to the right dorsolateral pre-frontal cortex (RDLPFC) with a total of 3600 pulses, followed by an LDLPFC treatment of 4950 pulses. The RDLPFC treatment was administered at a continuous burst rate of 50 Hertz lasting for a total of 239 seconds, again with three pulses in each burst. The RDLPFC treatment was administered without secondary stimulation, while patients wore earplugs. The TBS-20 Hz were similar to the TBS-50 Hz treatments, other than the frequency of the pulses within each burst.

Prior to beginning treatment, each patient obtained an individual 3T (3-Tesla) 3-dimensional T1 weighted MPR (Multi-Planar Reconstructed) MRI scan. The MRI scan for each patient was imported and segmented in order to obtain a head model of the scalp and brain using ANT-Neuro Visor 2.0 Infrared Tracking Frameless Stereotaxy Neuronavigation System (Enschede, Netherlands). Neuronavigation was used to more accurately identify specific brain regions and be able to place the magnetic coil perpendicular to the gyms at the regions of interest. The MRI was normalized to the Talairach Coordinate Space and the target markers for right Brodmann Area 46 and left Brodmann Area 46 were placed for use during subsequent TMS sessions. Each patient also answered Beck Depression Inventory II (BDI-II) and Beck Anxiety Inventory (BAI) rating scales before the start of treatment as well as weekly thereafter. The Beck Depression Inventory II (BDI-II) rating was chosen as the primary outcome measure. The criteria for response to treatment was a 50% decrease of a patient's BDI II scale score and for remission was a BDI-II scale score of under 10.

Theta burst stimulation pulses were administered using a MagPro X-100 TMS device with Mag Option and liquid cooled butterfly B-65 figure eight coil. Resting bilateral motor thresholds (MT) were measured each week to accurately determine the appropriate stimulation intensity. Single pulses of stimulation were applied to the motor cortex at the region controlling the contralateral abductor policis brevis muscle and the MT was visually determined to be the lowest level of stimulation capable of causing a twitch in the contralateral thumb.

In an effort to maximize efficacy of treatment, each patient received a series of treatment protocols that differed in stimulation frequency and laterality as previously described. Patients listened to uplifting music of their choice during LDLPFC stimulation, which is believed to increase regional blood flow.

For all unilateral theta burst protocols, as indicated in the chart of FIG. 14, the pulses were delivered in a theta burst pattern (3 pulses each burst, with bursts repeated at 5 Hz frequency) with a 2 second stimulation interval and an 8 second intertrain interval. Pulses within each burst were separated with a timing corresponding to 20 Hertz or 50 Hertz, varying depending upon the therapy regimen. For bilateral treatments, as similarly indicated by the chart of FIG. 14, the RDLPFC therapy involved continuous bursts delivered for 239 seconds total, with 3 pulses per burst. Bursts again were separated by a timing corresponding to 5 Hertz. Thus, the LDLPFC TBS-50 Hz and LDLPFC TBS-20 Hz protocols varied only in the frequency at which the pulses within each burst were delivered. The bilateral sequential TBS-50 Hz and the bilateral sequential TBS-20 Hz also only varied in the pulse frequency. The difference between the LDLPFC and bilateral sequential protocols is that the former contains only one treatment and is administered over LDLPFC, while the latter contains two treatments administered sequentially one right after the other. In the bilateral sequential protocols, stimulation over RDLPFC is followed by stimulation over LDLPFC. The coil for each treatment is placed such that it is perpendicular to the gyms at the target location.

After remission was reached, each patient underwent an eight-week taper phase, where the number of treatment sessions was reduced by one every two weeks. Tapering was done to reduce the chances of relapse.

FIGS. 15 through 19 summarize the results of the novel theta burst TMS treatment, as compared to conventional TMS treatment. FIG. 15 is a chart indicating how the individual patients in the study group responded to treatments summarized in FIG. 14, in terms of BDI-II scores. The first patient, for example, showed some improvement with LDLPFC at TBS-50 Hz in a first treatment, but did not reach clinical remission. A second treatment using bilateral sequential TMS at TBS-50 Hz resulted in virtually no improvement, with the BDI-II score moving only slightly from 18 to 17. After some passage of time (a gap of seven months), the first patient returned for treatment with a BDI-II score of 44. The patient was started with LDLPFC theta burst stimulation according to the parameters in FIG. 14, and responded extremely well with a drop in BDI-II score down to 20 after conclusion of the protocol. The LDLPFC protocol at TBS-20 Hz was switched to a bilateral sequential TMS protocol at TBS-20 Hz according to the parameters shown in FIG. 14, at which point the patient's BDI-II scored dropped to 7 and reached clinical remission. Thus, for the first patient, the TBS-20 Hz was able to achieve a success that was not achieved using the TBS-50 Hz.

The second patient also showed some initial improvement with LDLPFC at TBS-50 Hz in a first treatment, but did not reach clinical remission. A second treatment using bilateral sequential TMS at TBS-50 Hz resulted in virtually no improvement, with the BDI-II score moving only slightly from 16 to 15. The patient was then transitioned to LDLPFC TBS-20 Hz according to the parameters in FIG. 15, and responded very well with a drop in BDI-II score down to 6 after conclusion of the protocol, reaching clinical remission. Because of the successful results with LDLPFC, it was unnecessary to advance the patient to the bilateral sequential TMS protocol at TBS-20 Hz. Thus, for the second patient, the TBS-20 Hz was also substantially superior to the TBS-50 Hz and was able to achieve clinical remission where the TBS-50 Hz was not.

The third and fourth patients were both started with bilateral sequential TBS-50 Hz with modest results, but not clinical remission. Both patients were then transitioned to LDLPFC TBS-20 Hz according to the parameters in FIG. 14, and responded very well with a drop in BDI score down to 12 and 6 respectively after conclusion of the protocol. For the third patient, the LDLPFC protocol at TBS-20 Hz was followed immediately by a bilateral sequential TMS protocol at TBS-20 Hz according to the parameters shown in FIG. 14, at which point the patient's BDI-II scored dropped to 8 and clinical remission for that patient was reached. Because of the successful results with LDLPFC for the fourth patient, it was unnecessary to advance the patient to the bilateral sequential TMS protocol at TBS-20 Hz. Thus, for the third and fourth patients, the TBS-20 Hz was again surprisingly superior to the TBS-50 Hz, and was able to achieve clinical remission where the TBS-50 Hz was not.

FIGS. 16A-16D are graphs related to the data in FIG. 15, illustrating over time how patients in the study group responded to treatments summarized in FIG. 14, in terms of BDI-II scores. The graphs are broken down by treatment week, with each whole number corresponding to one week of treatment and the fractions corresponding to treatment days (where each 0.2 represents one day). The graphs in FIGS. 16A-16D indicate the week by week variance in BDI-II scores, confirming the substantially superior response of the patients to the TBS-20 Hz therapy regimen over the TBS-50 Hz regimen. The FIG. 16A graph shows a break in between treatments, during which time the patient experienced a serious depression episode that was only partially mitigated by using the TBS-50 Hz bilateral sequential treatment. The graphs also indicate the taper periods during which therapy was backed down. From the graphs in FIGS. 16A-16D, it can be seen that the response to the TBS-20 Hz therapy regimen in each case was immediate and pronounced, representing in each case a substantial improvement over the TBS-50 Hz regimen. All patients reached remission, although none of them did so with the TBS-50 Hz therapy.

Figure 17:
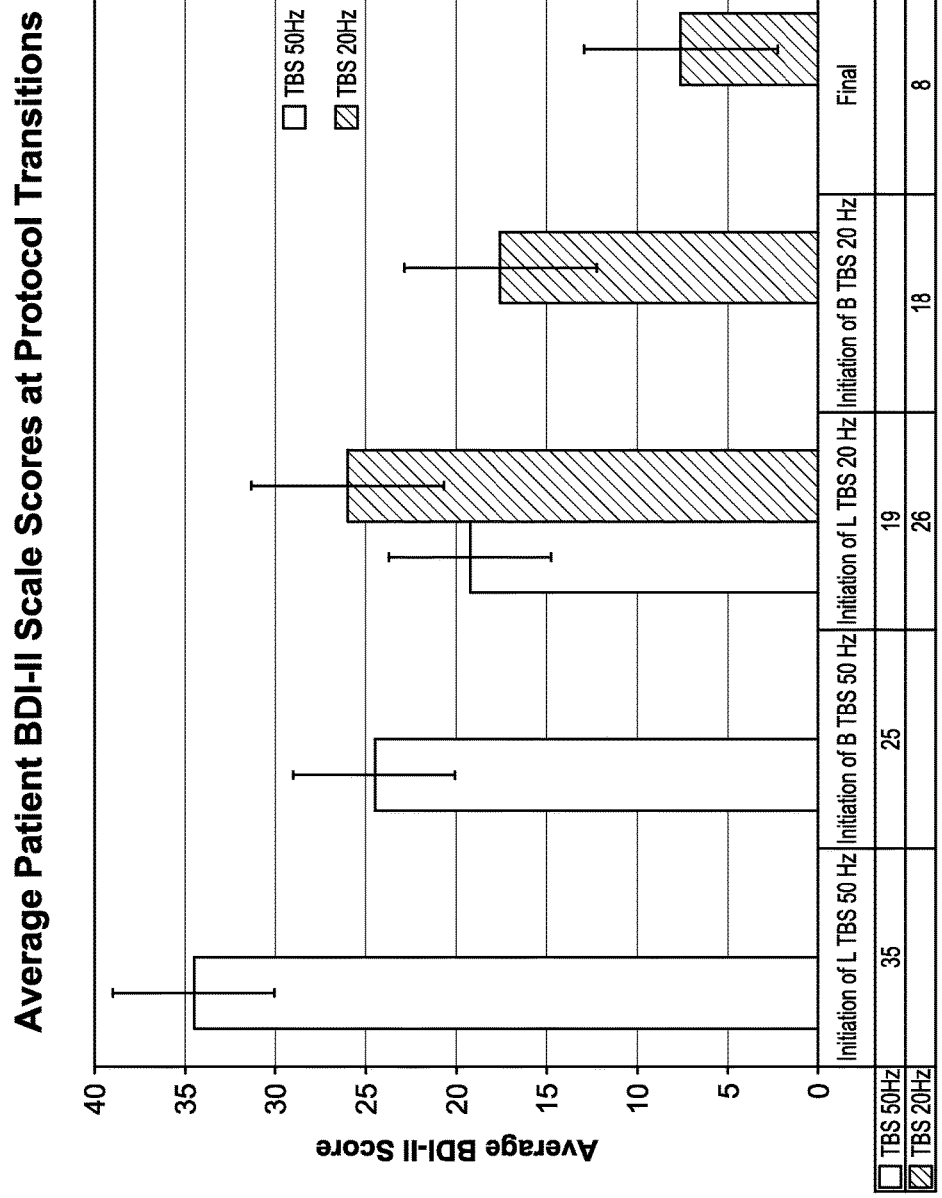
FIG. 17 is a graph summarizing average patient BDI-II scale scores at the initiation of each of the treatments described in FIG. 14, along with the average final scores.
Figure 18:
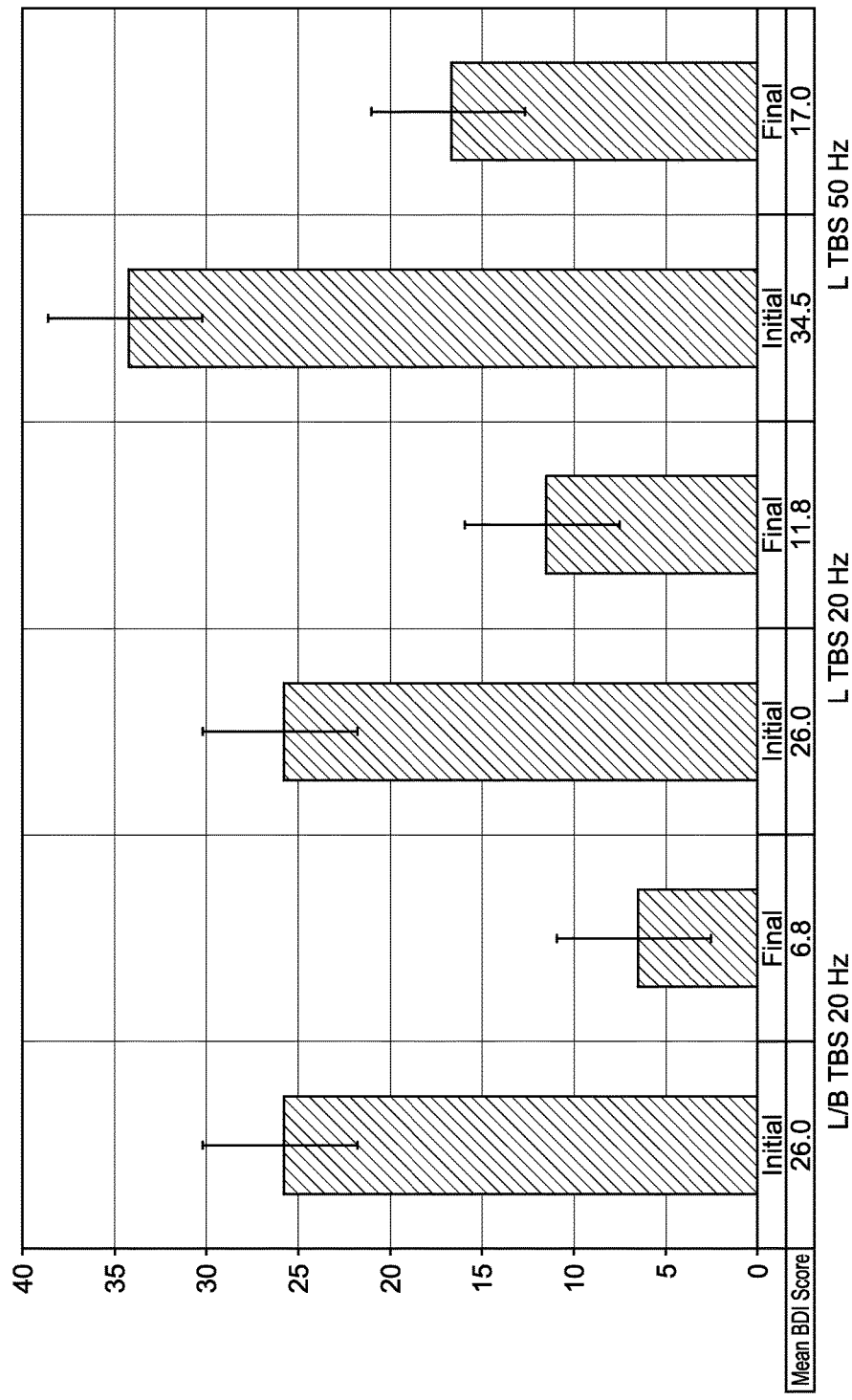
FIG. 18 is a graph summarizing and comparing pre- and post-treatment average BDI-II scale scores for the patient study group.
Figure 19:
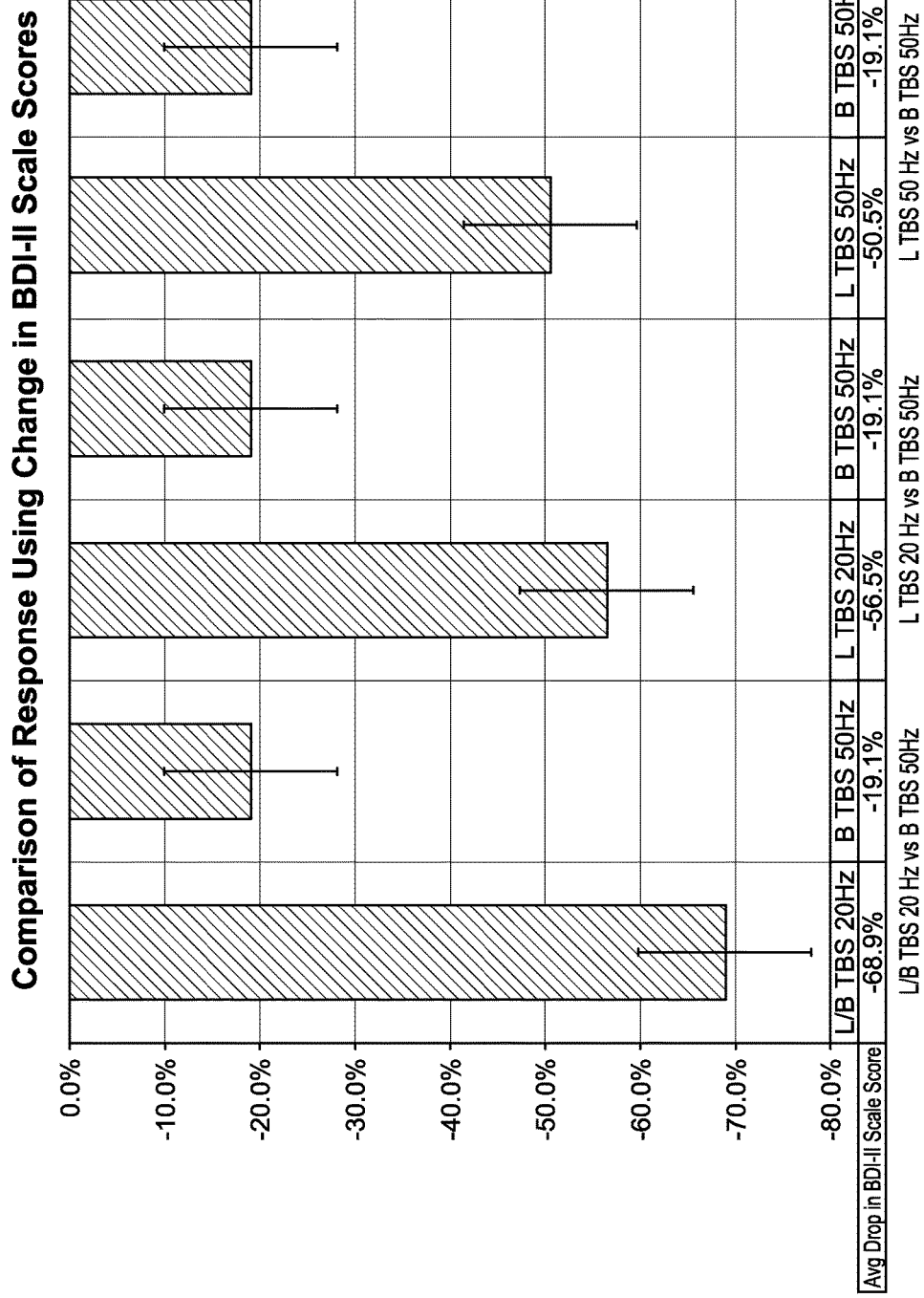
FIG. 19 is a graph comparing the response of the patients in the study group to the treatments described in FIG. 14, in terms of BDI-II scale scores.

FIGS. 17-19 are graphs summarizing the BDI-II scores of the patients in the study groups, from different respects. FIG. 17 is a graph summarizing average patient BDI-II scale scores at the initiation of each of the treatments described in FIG. 14, along with the average final scores. As shown in FIG. 17, at the initiation of the LDLPFC TBS-50 Hz treatment, the average BDI-II score for the study group was 35 At the initiation of the bilateral sequential treatment with TBS-50 Hz, the average BDI-II score for the study group was around 25. At the initiation of the LDLPFC theta burst stimulation treatment at TBS-20 Hz, the average BDI-II score for the study group was around 19 for the three patients who had used theta burst TBS-50 Hz therapy first, and was around 26 for the single patient who did not use theta burst TBS-50 Hz therapy. At the initiation of the bilateral sequential burst stimulation treatment at TBS-20 Hz, the average BDI-II score for the study group was around 18. The final BDI-II scores for the study group at the conclusion of their treatments was approximately 8.

FIG. 18 is a graph summarizing and comparing pre- and post-treatment average BDI-II scale scores for the patient study group, broken down by therapy. As shown in FIG. 18, the initial average BDI-II score for unilateral LDLPFC treatment with TBS-20 Hz was around 26.0, and the average of the final was 11.8. The initial average BDI-II score for unilateral LDLPFC treatment with TBS-50 Hz was around 34.50, and the average of the final was 17.0. The initial average BDI-II score for bilateral sequential treatment with TBS-20 Hz was around 26.0, and the average of the final was 6.8. Again, this data demonstrates that using the TBS-20 Hz therapies was superior to unilateral LDLPFC treatment with TBS-50 Hz and, moreover, that bilateral sequential treatment with TBS-20 Hz provided not only the most improvement but also to an average value within the zone of remission.

The patient study data is analyzed from yet another perspective in FIG. 19, which is a graph comparing the response of the patients in the study group to the treatments described in FIG. 14 in terms of percentage improvement in BDI-II scale scores, using bilateral sequential treatment with TBS-50 Hz as a baseline. As shown in FIG. 19, the average drop in BDI-II scale scores for the bilateral sequential treatment with TBS-50 Hz (B TBS-50 Hz) was about 19.1%. For the unilateral LDLPFC treatment with TBS-50 Hz (L TBS-50 Hz), the average drop in BDI-II scale scores was about 50.5%. For the unilateral LDLPFC treatment with TBS-20 Hz (L TBS-20 Hz), the average drop in BDI-II scale scores was about 56.5%. Lastly, the average drop in BDI-II scale scores for the bilateral sequential treatment with TBS-20 Hz (L/B TBS-20 Hz) was about 68.9%. It should be noted that the values in FIG. 19 are in terms of percentages. To the extent that the TBS-20 Hz therapies were used after the TBS-50 Hz treatments were applied and had plateaued, it would be expected that the changes that would have been brought about using only the TBS-20 Hz therapies would have been even more pronounced. But in any event, the data in FIG. 19 illustrates the superiority of the TBS-20 Hz methodologies for both unilateral and bilateral theta burst stimulation protocols.

In terms of analyzing the results of the patient study it may be noted that the first patient was titrated up on seroquel by his primary psychiatrist during the middle portion of the treatment due to unrelenting insomnia, but since he had failed the medication in an earlier medication trial, any likelihood that seroquel contributed to his response is low.

An additional study was performed with a larger study group including the patients in the first study group described above. The results of the larger study were generally consistent with those of the first study group. A total of ten patients were involved in the larger study, with the first four being the same patients as the first study group previously described. FIG. 31 is a chart identifying demographical and clinical characteristics of patients from the larger study of theta burst TMS stimulation including at 20 Hertz. The information in FIG. 31 includes, among other things, the ages and genders of the patients, their diagnoses, the duration of their illnesses, the medications taken concurrently with the theta burst treatment, and their BDI-II Rating Scale scores.

Figure 32:
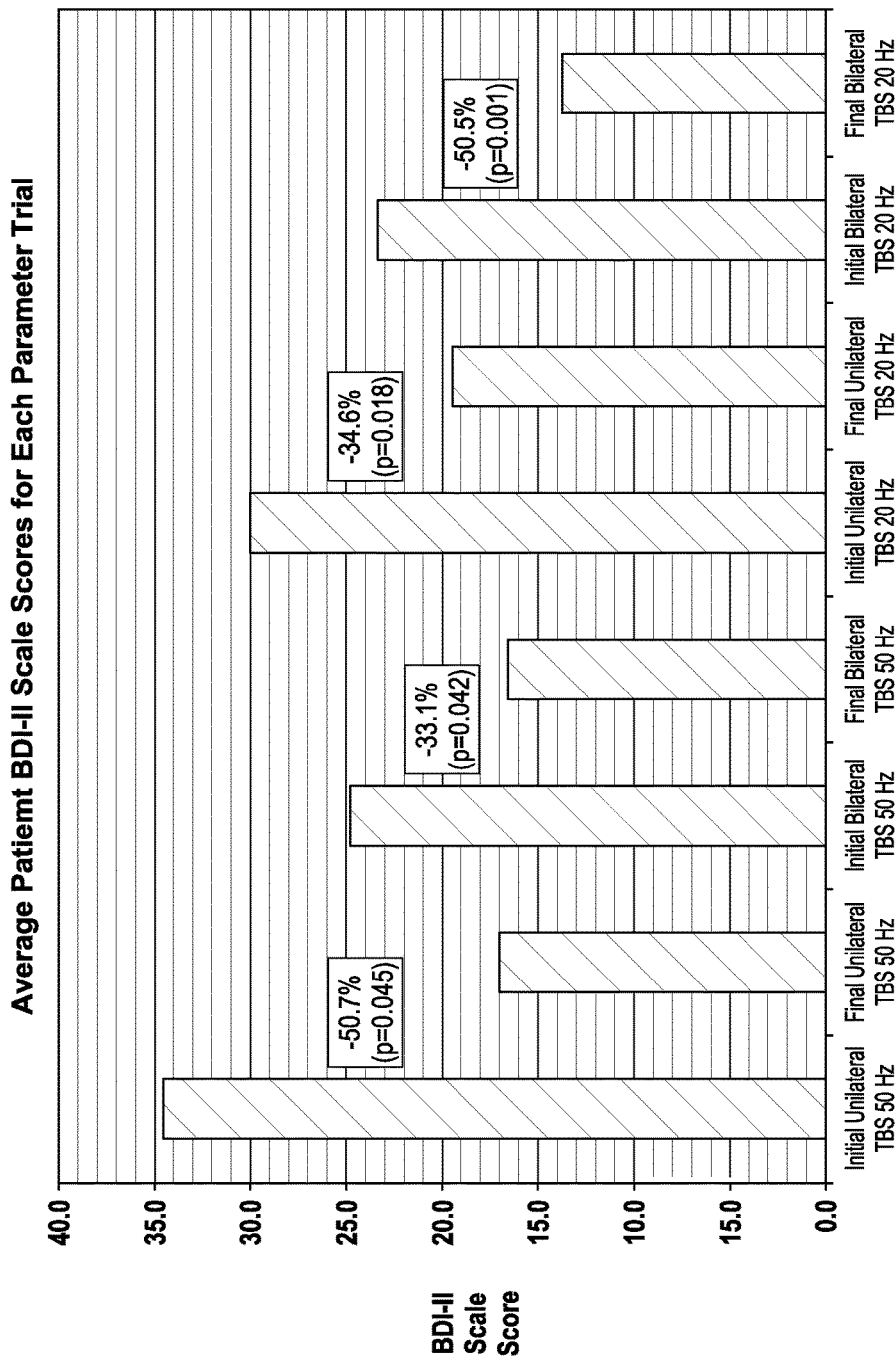
FIG. 32 is a graph summarizing and comparing pre- and post-treatment average BDI-II scale scores for the patient study group of FIG. 31.

FIG. 32 is a graph summarizing and comparing pre- and post-treatment average BDI-II scale scores for the patient study group of FIG. 31, broken down by therapy. As shown in FIG. 32, the initial average BDI-II score for unilateral LDLPFC treatment with TBS-20 Hz for the larger study group was around 30.0, and the average of the final was 19. The initial average BDI-II score for unilateral LDLPFC treatment with TBS-50 Hz was around 34.5, and the average of the final was 17.0. The initial average BDI-II score for bilateral sequential treatment with TBS-20 Hz was around 23.5, and the average of the final was around 14.0. Similar to the smaller study group, this data demonstrates that using the TBS-20 Hz therapies was generally superior to unilateral LDLPFC treatment with TBS-50 Hz and, moreover, that bilateral sequential treatment with TBS-20 Hz provided not only very significant improvement but also improved the BDI-II scores to an average value within the zone of remission.

Figure 34:
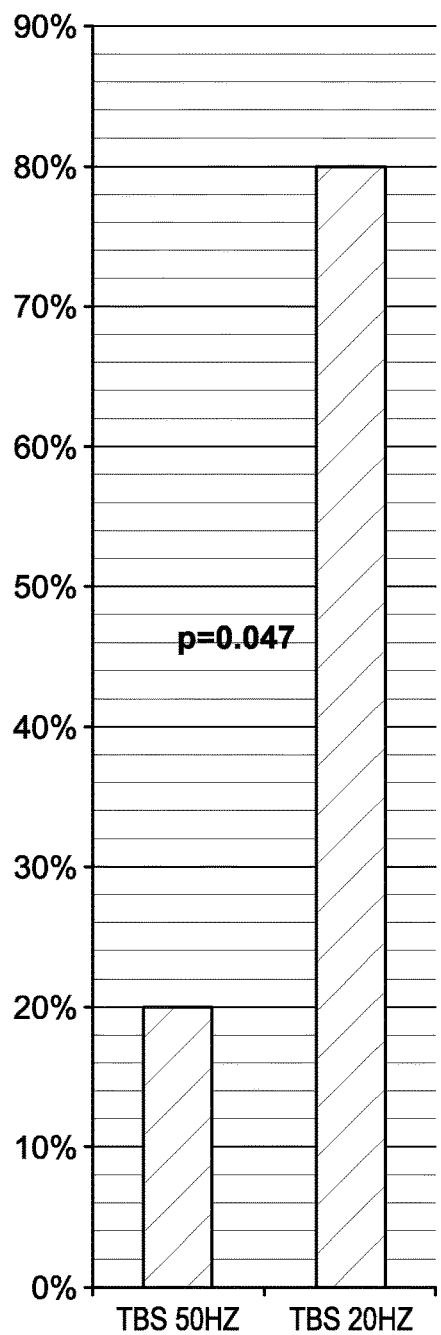
FIG. 34 is a graph summarizing and comparing remission rates between theta burst TMS stimulation at 20 Hz and 50 Hz.

FIG. 33 is a chart identifying sequences of various treatments for the study group of patients summarized in FIG. 31. As summarized in the chart, the therapies started with LDLPFC TBS-50 Hz for the first two patients, then progressed to bilateral sequential TBS-50 Hz, and then to LDLPFC TBS-20 Hz, with one of the two initial patients then progressing to bilateral sequential TBS-20 Hz. Patients three and four began with Bilateral TBS-50 Hz due to significant anxiety symptoms, and both then advanced to LDLPFC TBS-20 Hz and, one of the two patients continued with bilateral sequential TBS-20 Hz. Patients five and six began with unilateral LDLPFC TBS-20 Hz as none of the prior patients remitted with TBS-50 Hz. Patient five was the only non-remitter, and dropped out of treatment before his parameters could be switched to TBS-50 Hz. Patients seven through nine began with bilateral TBS-20 Hz because the majority of prior patients had not remitted with unilateral TBS-20 Hz. Patient ten failed to reach remission with bilateral TBS-20 Hz but remitted after switching to bilateral TBS-50 Hz. FIG. 34 is a graph summarizing and comparing remission rates between theta burst TMS stimulation at 20 Hz and 50 Hz. As can be seen in the graph, TBS-20 Hz achieved an 80% remission rate, four times higher than the 20% remission rate for TBS-50 Hz.

FIG. 35 is a chart indicating more specifically the treatment protocols administered to the larger patient study group described in FIGS. 31-33 which, as can be seen from a comparison, are the same as the treatment protocols summarized in FIG. 14. For example, for the LDLPFC TBS-50 Hz stimulation treatment, a total of 4950 pulses were administered, with three pulses per burst at a frequency of 50 Hertz within each burst. The burst frequency itself, in all cases, was 5 Hertz. The total burst duration for each train of burst was 2 seconds, and the intertrain interval between burst trains was 8 seconds. The pulses were administered at 85-95% of the motor threshold. All treatments of LDLPFC were administered in combination with a secondary stimulus, in this case uplifting music chosen by each patient played during the treatment, to increase regional blood flow and enhance the TMS effects. The bilateral sequential stimulation involved a first treatment applied to the right dorsolateral pre-frontal cortex (RDLPFC) with a total of 3600 pulses, followed by an LDLPFC treatment of 4950 pulses. The RDLPFC treatment was administered at a continuous burst rate of 50 Hertz lasting for a total of 239 seconds, again with three pulses in each burst. The RDLPFC treatment was administered without secondary stimulation, while patients wore earplugs. The TBS-20 Hz were similar to the TBS-50 Hz treatments, other than the frequency of the pulses within each burst. The pre-treatment regimen, including MRI scan, was generally the same as with the first study group. As with the first study group, theta burst stimulation pulses were administered using a MagPro X-100 TMS device with Mag Option and liquid cooled butterfly B-65 figure eight coil. Resting bilateral motor thresholds (MT) were measured each week to accurately determine the appropriate stimulation intensity. Single pulses of stimulation were applied to the motor cortex at the region controlling the contralateral abductor policis brevis muscle and the MT was visually determined to be the lowest level of stimulation capable of causing a twitch in the contralateral thumb.

After remission was reached, each patient in the larger study group underwent an eight-week taper phase, where the number of treatment sessions was reduced by one every two weeks. Tapering was done to reduce the chances of relapse.

FIG. 36 is a chart identifying various treatment parameters and durations for the group of patients identified in FIGS. 31-33. Total treatment days ranged from 51 to 155, with the average being 69.9 days. Typically, patients would be treated once or twice per day, five days per week. The number of treatment days in each therapy protocol should be sufficient from a clinical standpoint to determine the general efficacy of each applied protocol.

The additional larger group study thus supports the superior efficacy of the TBS-20 Hz method over the TBS-50 Hz approach, achieving better results including a much superior remission rate. The results of the larger study were, as noted, generally consistent with those of the first study group.

3. Parameter Studies

Based on the strong success with TBS-20 Hz protocols on the patients in the first study group, further measurements were performed on a single human subject (not one of the original four patients in the study group) in an attempt to determine whether other frequencies nearby 20 Hertz were equally as potent. It was discovered through these efforts that other theta burst frequencies that are less than 50 Hertz and around the general range of 20-30 Hertz may also be particularly beneficial. It was also discovered that applying the bursts at other frequencies besides 5 Hertz could also impact the potential efficacy of the protocol. Further it was surprisingly discovered that varying other parameters such as the number of pulses per burst had a material effect on the potential efficacy of a treatment. It was also surprisingly discovered that in some cases the theta burst therapies applied in the range of 20-30 Hertz would have an inhibitory effect, and in some cases those therapies applied within that range would have an excitatory effect, depending on the specific frequencies, number of pulses per burst, and frequency of bursts. Heretofore, it has been reported only that theta burst stimulation at 50 Hertz would have an inhibitory effect. Therefore, the fact that excitatory responses were noted with theta burst stimulation in the range of 20-30 Hertz was particularly unexpected.

The methodology used to determine the effective and optimal parameters for delivering theta burst treatment was largely based on evaluation of changes of motor evoked potential (MEP) measurements for different combinations of theta frequency, number of pulses per burst, and frequency of bursts. A relationship between MEP amplitude changes and responsiveness to theta burst TMS treatment has been previously postulated in certain literature. The study conducted here initially established with the subject in question that MEP amplitude changes corresponded to improved responsiveness to theta burst treatment at 20 Hertz; that is, a significantly more substantial and pronounced effect in MEP amplitude change was noted after application of 20 Hertz theta burst pulses than after 50 Hertz theta burst pulses. Given this consistency with the experiences of the patient study group, it could be concluded more broadly that the brain responds more favorably or dramatically to pulses administered at 20 Hertz, and further that changes in MEP amplitude levels do correlate to increased responsiveness of the brain at a given frequency.

The methodology for obtaining the MEP values in FIG. 20A was as follows. For each protocol, a burst sequence containing typically four to six bursts (12 to 20 pulses) was applied to the cranial area in the customary manner. Motor evoked potential was measured using a finger sensor, with measurements taken every 30 seconds for five minutes before the start of the protocol and for 30 minutes after. The measured MEP amplitude was obtained as a value in microvolts. Then the data points from these measurements were averaged in 5-minute blocks (10 data points each) to give a single average baseline MEP value, still in microvolts, as well as six averaged post-stimulus data points, also in microvolts. Then the latter six data points were normalized, i.e., divided by the baseline value to give a percentage value of the data point. For example, a 150 microvolt averaged data point divided by a baseline average of 100 microvolts would give a value of 1.5, or 150%. Then the number value of one (or 100%) is subtracted from the percentage to give a percentage change from baseline (the baseline value thus equates to 100% or 1 since it is divided by itself). Thus, in the above example where the averaged measured value is 150 microvolts, the normalization process would involve taking the difference of 150%–100%=50% (or 1.5–1=0.5), meaning a change from baseline (i.e., starting at 100% and going to 150% is a change of 50%), which would be the value then plotted in the MEP chart of FIG. 20A. All the MEP responses are by definition above threshold because a subthreshold response would not register at all on the EMG voltage feed of the finger sensor.

It may be noted that in taking MEP measurements, there is generally no standard protocol in the field with respect to the interval between measurements. However, observations have shown that taking MEP measurements too close together can lead to skewed results, because there is greater variation in the measurements that are closer together. Therefore, a 30 second interval between MEP measurements was used in order to prevent or minimize the risk of distortion, and to increase the reliability of the methodology.

Using the above methodology, MEP amplitude changes were measured for a variety of different combinations of theta frequency, number of pulses per burst, and frequency of bursts. This data is summarized in the charts appearing in FIGS. 20A and 20B. FIG. 20A is a chart illustrating percentage changes in motor evoked potential (MEP) amplitude measurements for different combinations of parameters. The top subchart 2013 of the chart in FIG. 20A indicates MEP amplitude percentage changes (normalized) for theta burst TMS stimulation applied over a theta frequency range of from 1 Hertz to 50 Hertz, with the frequency of bursts being between 1 and 20 Hertz, and the number of pulses in each burst being three. (A 1 Hertz theta frequency and 1 Hertz burst frequency combination basically equates to a monotonic pulse sequence at 1 Hertz). Each cell in the top subchart 2013 indicates the percentage of change in the MEP amplitude, with the shaded cells (or negative numbers) indicating an inhibitory effect, and the unshaded cells (or positive numbers) indicating an excitatory effect. Entirely blank cells indicate that no data was measured for those combinations.

The second subchart 2015 in FIG. 20A indicates MEP amplitude percentage changes (normalized) for theta burst TMS stimulation applied over a theta frequency range of from 20 Hertz to 28 Hertz, with the frequency of bursts again being between 1 and 20 Hertz, and the number of pulses in each burst being two. As before, each cell in the second subchart 2015 indicates the percentage of change in the MEP amplitude level, with the shaded cells (or negative numbers) indicating an inhibitory effect, and the unshaded cells (or positive numbers) indicating an excitatory effect. Entirely blank cells indicate that no data was measured for those combinations.

The third subchart 2018 of in FIG. 20A indicates MEP amplitude percentage changes (normalized) for theta burst TMS stimulation applied over a theta frequency range of from 25 Hertz to 30 Hertz, with the frequency of bursts again being between 1 and 20 Hertz, and the number of pulses in each burst being four or five. As before, each cell in the third subchart 2018 indicates the percentage of change in the MEP amplitude level, with the shaded cells (or negative numbers) indicating an inhibitory effect, and the unshaded cells (or positive numbers) indicating an excitatory effect. Entirely blank cells indicate that no data was measured for those combinations.

The fourth subchart 2020 in FIG. 20A indicates MEP amplitude percentage changes (normalized) for theta burst TMS stimulation applied at a theta frequency of 20 Hertz, with the frequency of bursts again being 5 Hertz, the number of pulses being three in each case, but varying the number of bursts between 1 and 13. As before, each cell in the fourth subchart 2020 indicates the percentage of change in the MEP amplitude, with the shaded cells (or negative numbers) indicating an inhibitory effect, and the unshaded cells (or positive numbers) indicating an excitatory effect. Entirely blank cells indicate that no data was measured for those combinations. This fourth subchart 2020 explored the possibility of providing theta burst TMS treatment with only a small number of pulses, a subject discussed in much greater detail later.

The measurement data summarized the chart of FIG. 20A has a number of quite surprising and remarkable results. To discuss the details of the FIG. 20A chart, it is convenient to abbreviate each entry in the form "BF/PF/NP" where "BF" refers to the frequency timing between bursts, "PF" refers to the frequency timing between pulses (also referred to as the theta burst frequency), and "NP" refers to the number of pulses in each burst. Thus, for example, the abbreviation "5/20/3" would refer to a theta burst stimulation pattern with bursts provided at a timing corresponding to 5 Hertz, with pulses in each burst provided at a timing corresponding to 20 Hertz, and with 3 pulses in each burst. (This is the pattern also shown in FIG. 4A).

First, it is noted that the 5/20/3 combination according to the FIG. 20A subchart 2013 yields a −0.5 normalized (or 50%) reduction in measured MEP amplitude level, one of the most pronounced effects in the chart, and corroborating the improved efficacy of the 20 Hertz theta burst TMS stimulation treatment as observed in the patient study group. By contrast, the 5/50/3 theta burst treatment, representing the conventional approach for TMS treatment, provided only a −0.09 (or 9%) reduction in measured MEP amplitude level. Therefore, the 20 Hertz theta burst pulses in the 5/20/3 pattern were startlingly found to be over five times as effective as the 50 Hertz theta burst pulses in the 5/50/3 pattern, in relation to MEP amplitude, by changing only the theta burst frequency.

In terms of further comparison, the top subchart 2013 of FIG. 20A illustrates also the greatest change in measured MEP amplitude level for the 6/20/3 pattern, that is, a theta burst stimulation pattern with bursts provided at a timing corresponding to 6 Hertz, with pulses in each burst provided at a timing corresponding to 20 Hertz, and with 3 pulses in each burst. This pattern yielded a −0.59 normalized (or 59%) reduction in MEP amplitude level. Other patterns which yielded significant inhibitory effects were for the 5/22/3 and 6/24/3 patterns. Lesser effects comparable to the 5/50/3 theta burst treatment were observed for the 4/16/3 and 4/20/3 patterns.

It was also observed from the data in the top subchart 2013 of FIG. 20A that certain theta burst patterns within the range close to 30 Hertz could produce significant excitatory effects, which was a result not anticipated. For example, the 5/28/3 pattern and the 6/30/3 pattern both yielded significant excitatory responses of 0.26 (or +26%) and 0.31 (or +31%) elevations in MEP amplitude level, respectively. By contrast, patterns such as 5/18/3 and 5/24/3 produced a small but generally negligible increase in the MEP amplitude level, in the excitatory direction.

In another unexpected revelation, the pattern 20/20/1 (corresponding to a continuous TMS pattern of pulses at 20 Hertz) yielded an inhibitory effect of −0.37 (or 37%) reduction in MEP amplitude level. Previously, it was not understood or appreciated in the field that a continuous TMS pattern could produce an inhibitory effect, much less a very pronounced inhibitory effect such as observed and recorded in the chart of FIG. 20A. By comparison, the 1/1/1 (continuous 1 Hertz) TMS stimulation pattern, which has been used conventionally for experimental purposes, yielded only a minor 0.1 (or 10%) reduction in MEP amplitude level. The contrast of these results substantiates yet again the particular special nature of the TBS-20 Hz stimulation protocol.

Turning now to the second subchart 2015 where two-pulse burst patterns were administered, it is immediately noted that a very pronounced excitatory effect was produced for the 5/24/2 pattern, yielding a remarkable 0.87 (or +87%) elevation in MEP amplitude level. The magnitude of this change in MEP amplitude was completely unforeseen, putting aside the fact that theta burst stimulation was creating excitatory responses at all. Closely following that result is the 6/24/2 pattern, which yielded an elevation of 0.65 (or +65%) in MEP amplitude level. The nearby pattern of 4/24/2 only provided a modest excitatory response, with an elevation of 0.16 (or +16%) in MEP amplitude level. Conversely, other theta burst frequencies resulted in an inhibitory effect, such as the 5/20/2 and 5/25/2 patterns, both yielding a reduction of 0.18 (or −18%) in MEP amplitude level, and the 5/22/2 pattern, yielding a reduction of 0.35 (or −35%) in MEP amplitude level. Also, the pattern 7/28/2 yielded a reduction of 0.42 (or −42%) in the measured MEP amplitude level.

Turning to the third subchart 2018 which contains data from four or five pulse burst patterns, only a relatively small number of measurements were conducted for these patterns, neither with significant results. It was observed that the 5/25/4 pattern, for example, yielded a reduction of 0.08 (or −8%) in MEP amplitude level, while the 5/30/5 pattern yielded a small elevation of 0.07 (or +7%) in MEP amplitude level.

The fourth subchart 2020 in FIG. 20A shows MEP amplitude percentage changes (normalized) for theta burst TMS stimulation applied at a theta frequency of 20 Hertz and frequency of bursts being 5 Hertz, with the number of pulses being three in each case, but varying the number of bursts between 1 and 13. It was observed that four total bursts (a total of 12 pulses) using the 5/20/3 pattern produced a pronounced reduction in MEP amplitude level of 50%, whereas 2 bursts provided only a 27% reduction. By contrast, a larger number of bursts/pulses produced different amounts of excitatory effect. For example, using 10 bursts (30 pulses) produced an excitatory effect resulting in a 23% increase in MEP amplitude level, and using 13 bursts (39 pulses) actually produced a lesser excitatory effect resulting in a 14% increase in MEP amplitude level. This data indicates that the number of pulses can be quite important in determining the excitatory or inhibitory effect of the theta burst treatment, as well as the magnitude of the effect.

FIG. 20B is a chart indicating the statistical significance of the values in the FIG. 20A chart, and generally follows the same format of FIG. 20A in terms of the different combinations of pulse sequence parameters. Thus, a top subchart 2033 in FIG. 20B corresponds to the top subchart 2013 in FIG. 20A; the second subchart 2035 in FIG. 20B corresponds to the second subchart 2015 in FIG. 20A; and the third subchart 2038 in FIG. 20B corresponds to the third subchart 2018 in FIG. 20A. Statistical determinations for the fourth subchart 2020 in FIG. 20A were not made, and hence no values appear in the fourth subchart 2040 in FIG. 20B. In each cell in the entries of FIG. 20B are p-values related to probability and indicating the potential statistical significance of the findings in FIG. 20A. The p-value here is a statistical measure which represents the probability that the final MEP values would have occurred due to chance alone. The values in the shaded cells in FIG. 20B represent statistically significant values (p<0.05), while the values in the unshaded cells lacked sufficient information to draw a conclusion about statistical significance.

From the statistical data in FIG. 20B, it can be seen that the probability of the measured value for the 5/16/3 pattern as being an anomaly is 4% (0.040), and for the 5/20/3, 6/20/3, 20/20/1, 5/22/2, 5/24/2, 6/24/2 and 7/28/2 the probability of the measured values being anomalous is 2% (0.020) or less.

The measurement data summarized the charts of FIGS. 20A and 20B show a number of remarkable patterns that provide significant insight into the relationship of artificial TMS stimuli and its effect on the human brain. Without intending to limit the invention in any manner, it is presently hypothesized that the artificial stimuli provided within the theta burst frequency range of approximately 20-30 Hertz are significantly closer to the brain's natural neurological frequencies used for conveying information among neurons; hence, stimuli applied at those frequencies result in a more pronounced effect as compared to the 50 Hertz protocols. It further appears from the data that there is a relationship in the number of pulses per burst, theta frequency, and burst repetition frequency that affect the efficacy of the applied pulses in terms of MEP changes. The number of pulses applied in a given burst affect the length of the "blank" interval or gap between bursts (as explained earlier in relation to FIG. 5), and thus provide an additional layer of variability, and additional frequency components, to the stimulation pattern. It is noted that, in general, patterns that are within a range of pulse/burst frequency ratios of four to five are particularly efficacious, whereas, by contrast, patterns that are outside that pulse/burst frequency ratio range appear to be less efficacious. For example, the 5/20/3 and 6/20/3 patterns have a pulse/burst frequency ratio of 4.0 and 3.33 respectively, and yielded pronounced changes in measured MEP that were also found to be statistically significant in nature. Pulse patterns of 5/24/2, 5/24/2 and 7/28/2 also have pulse/burst frequency ratios in the same range, and specifically have ratios of 4.8, 4.8 and 4.0 respectively, yielding in each case statistically significant changes in MEP measurements. The 5/16/3 pattern has a pulse/burst frequency ratio of 3.2. By way of comparison, the conventional 5/50/3 pattern has a pulse/burst frequency ratio of 10.0, which is not close to the 3 to 5 range. It is believed that no one in the field has heretofore reported these patterns and relationships previously, either from a general standpoint or a quantitative standpoint as done here.

Figure 21:
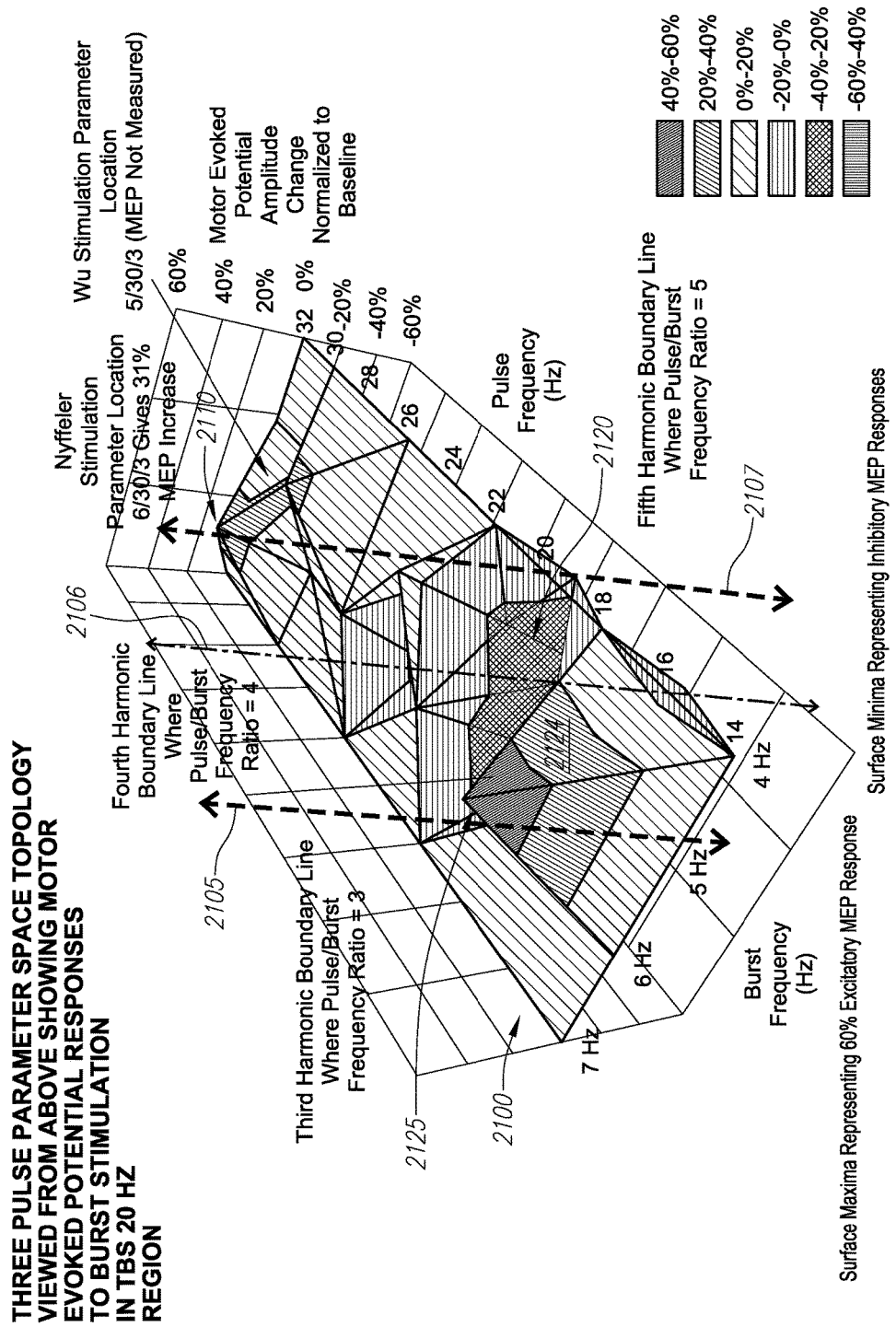
FIG. 21 is a parameter space topology graph (viewed from above) illustrating motor evoked potential responses to burst stimulation in a range around 20 Hertz with a three-pulse burst pattern.
Figure 22:
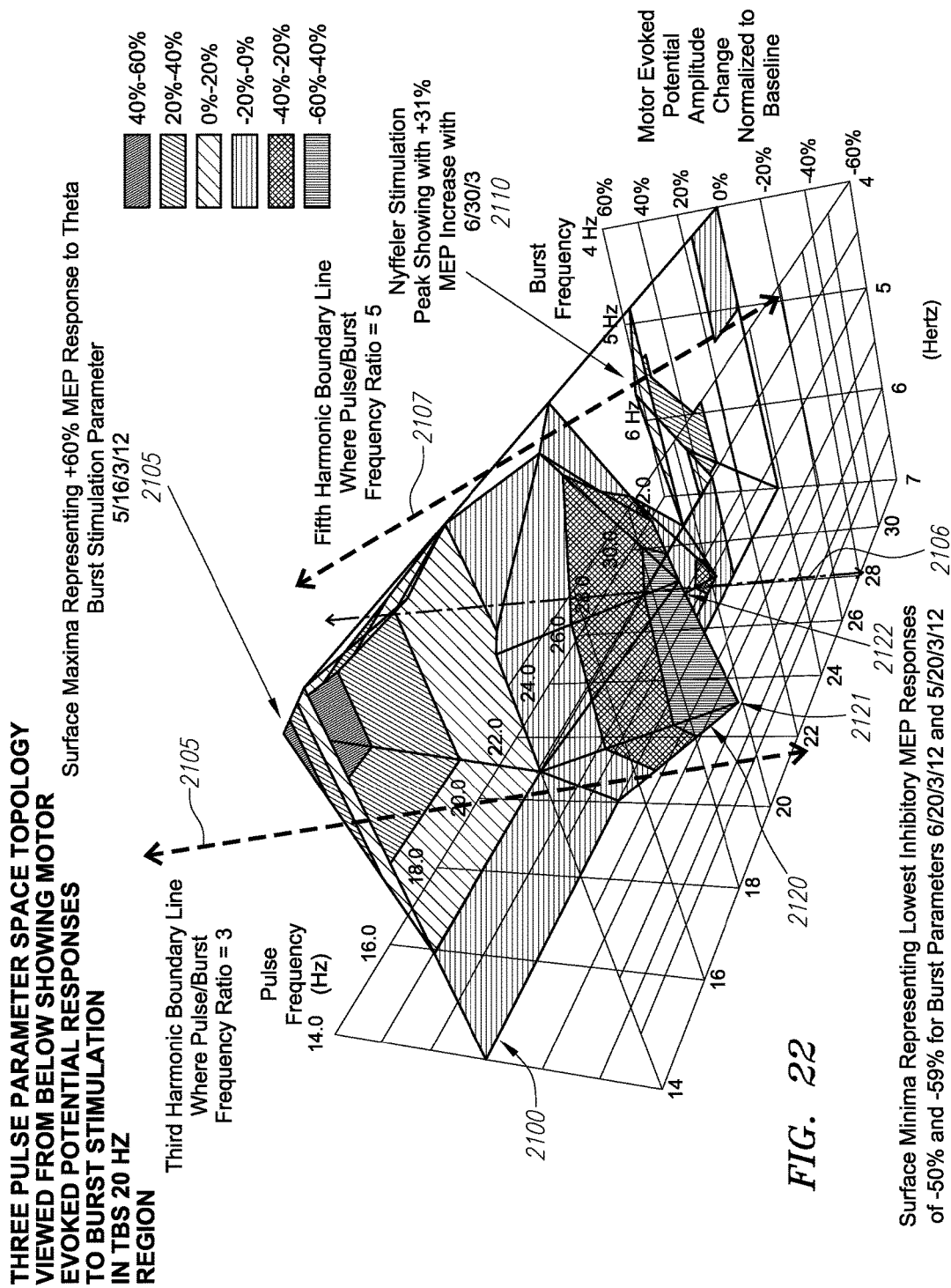
FIG. 22 is a view of the parameter space topology graph from below, illustrating motor evoked potential responses to burst stimulation in a range around 20 Hertz.
Figure 23:
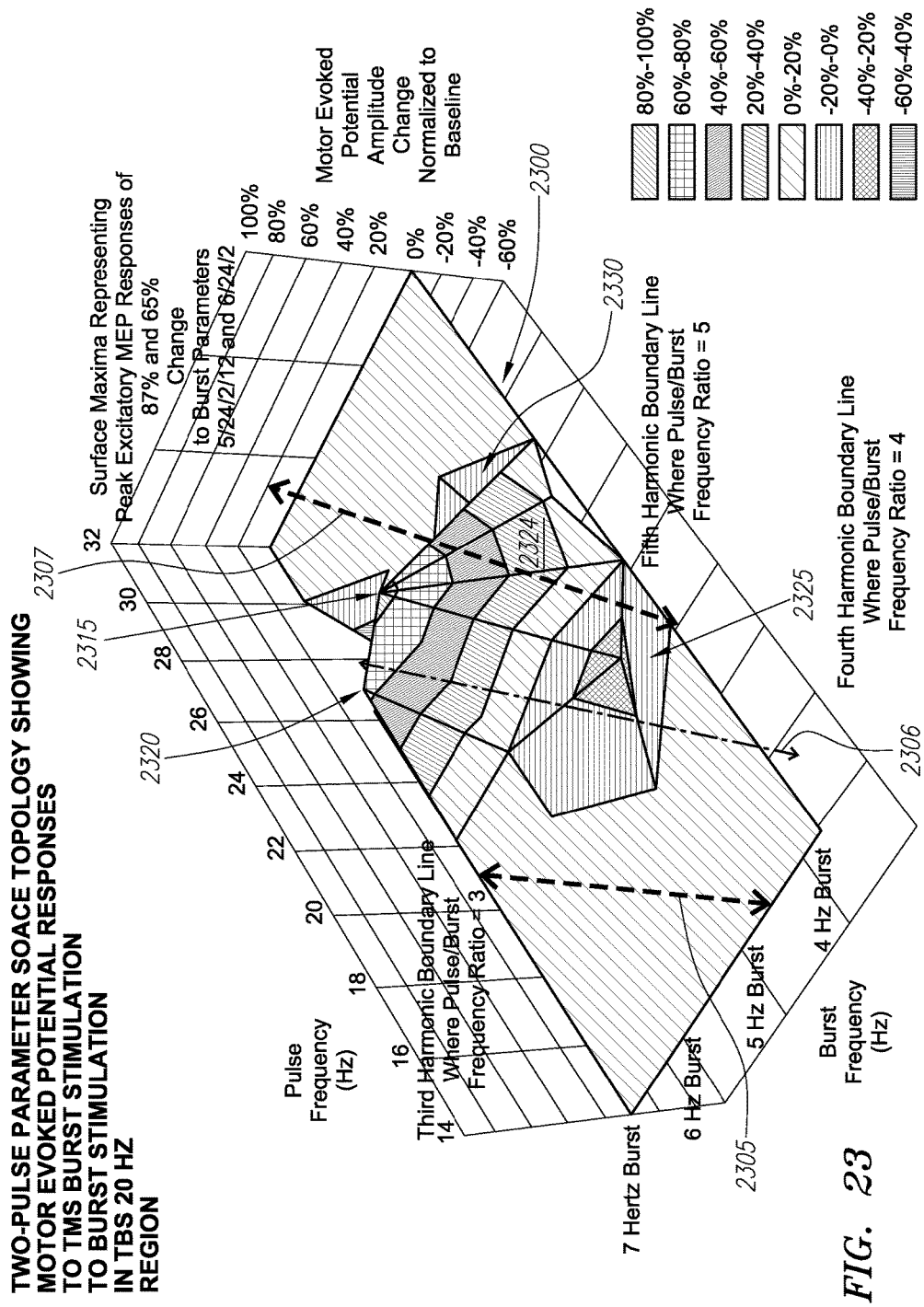
FIG. 23 is a parameter space topology graph (viewed from above) illustrating motor evoked potential responses to burst stimulation in a range around 20 Hertz with a two-pulse burst pattern.

To evaluate these pattern relationships further, the data from FIG. 20A was mapped to a 3-dimensional space, the results of which appear in FIGS. 21-23. More specifically, FIG. 21 is a parameter space topology graph (viewed from above) illustrating motor evoked potential responses to burst stimulation in a range around 20 Hertz with a three-pulse burst pattern, as taken from the data in FIG. 20A. FIG. 22 is a view of the same 3-dimensional parameter space topology graph from below. As shown in FIGS. 21 and 22, a three-dimensional map 2100 based on burst repetition frequency, pulse frequency, and normalized motor evoked potential (MEP) amplitude change comprises various peaks and valleys where unusually pronounced responses have been measured. The burst repetition frequency axis spans from 4 to 7 Hz, the pulse frequency axis spans from 14 to 32 Hz, and the normalized MEP amplitude change spans from +60% to −60%. As shown in FIG. 21 in particular, a large prominence 2124 is present over the area in the range of 5 Hz for burst repetition frequency and 16 Hz for theta burst pulse frequency, and signifies an area of substantial excitatory response to artificial stimuli with a theta burst pattern in that frequency combination range. The peak 2125 of the large prominence 2124 corresponds to the 5/16/3 pattern where an MEP amplitude change of +60% was measured. Also shown in FIG. 21 is a valley region 2120 corresponding to pronounced inhibitory responses. As better seen in the bottom view graph of FIG. 22, the valley 2120 encompasses responses for the 6/20/3 pattern (an inhibitory response in MEP amplitude of −59%) and for the 5/20/3 pattern (an inhibitory response in MEP amplitude of −50%).

Also appearing in the graphs of FIGS. 21 and 22 are dotted lines indicating the locations where the pulse/burst frequency ratios are 3, 4 and 5 respectively. In particular, line 2105 indicates where the pulse/burst frequency ratio is equal to 3, line 2106 indicates where the pulse/burst frequency ratio is equal to 4, and line 2107 indicates where the pulse/burst frequency ratio is equal to 5. As can be observed from FIGS. 21 and 22, the region between lines 2105 and 2107 (with a pulse/burst frequency ratio between 3 and 5) and in the range of about 15 Hz to 26 Hz provides significant MEP amplitude changes, indicating strong efficacy for artificial stimuli, applied within those ranges. By way of comparison, point 2110 represents MEP response for a 6/30/3 pattern, which is on the cusp of the 3 to 5 pulse/burst frequency ratio range, and resulted in an MEP amplitude increase of 31%. However the statistical reliability of that measurement was not shown to be as high as for the other measurements. It appears that while that 6/30/3 pattern yields some MEP response improvement, the patterns within the 3 to 5 pulse/burst frequency ratio range provide the maximum amount of MEP response change, and hence the greatest potential efficacy for TMS therapy.

FIG. 23 is a parameter space topology graph (viewed from above) illustrating motor evoked potential responses to burst stimulation in a range around 20 Hertz, for the two-pulse burst patterns. Thus, similar to FIGS. 21 and 22, FIG. 23 shows a three-dimensional map 2300 based on burst repetition frequency, pulse frequency, and normalized motor evoked potential (MEP) amplitude changes as the parameters. As shown in FIG. 23, there exist regions, as with the three-pulse burst protocols, where particularly significant responses were observed, in terms of MEP amplitude changes (and hence likely efficacy for TMS treatment). Specifically, the three-dimensional map 2300 illustrates a significant prominence 2324 in the positive direction showing substantial MEP amplitude changes for pulse frequencies in the range of about 22-26 Hertz, and most closely centered around 24 Hertz. The tallest peak 2315 of the prominence 2324 corresponds to a burst pattern of 5/24/2, providing an MEP change of 87%, although another tall peak 2320 in the same prominence 2324 corresponds to a burst pattern of 6/24/2. Therefore, it appears that two-pulse treatments in the range of pulse frequencies between 22 and 26 Hertz, with a burst repetition frequency of 4 to 5 Hertz, are particularly effective at modifying MEP response and therefore most likely to be efficacious for therapies involving TMS burst stimulation, where an excitatory response is sought.

Also appearing in FIG. 23 are multiple prominences in the negative direction, such as valleys 2325 and 2330, indicating a pronounced inhibitory response to the patterns with the particular pulse and burst frequency patterns in those ranges, for two-pulse burst patterns. For example, a first negative prominence 2325 appears to be related to pulse frequencies between 20 and 22 Hertz with a burst repetition frequency of between 4 and 6 Hertz, with the most pronounced effect at around a pulse frequency of around 21-22 Hertz and a burst repetition frequency of about 5 Hertz. A second negative prominence 2330 appears to be related to pulse frequencies between 26 and 29 Hertz with a burst repetition frequency of between 4 and 7 Hertz, with the most pronounced effect at around a pulse frequency of around 27-28 Hertz and a burst repetition frequency of either about 5 Hertz or about 7 Hertz.

Thus, it may be concluded from the graphs of FIGS. 21-23 and the underlying data that the pulse frequency, burst repetition frequency, pulse/burst frequency ratio, and number of delivered pulses per burst all may have a material impact on MEP response as well as the efficacy of TMS treatment. Certain combinations of pulse frequency, burst frequency, and number of delivered pulses appear to achieve the most significant results. Again, these findings are highly unexpected, given that heretofore the responsiveness of the brain to these stimulation frequencies had not been appreciated in the field, nor have the natural workings of the brain in relation to electronic activity and neural interaction been completely understood.

It should be noted that while whole number frequency patterns were selected in the experimental parameter combinations described in FIG. 20A for purposes of convenience, simplicity, and ease of comparison, there is no need to limit the parameters to whole frequency numbers. It is certainly possible that fractional values of theta burst frequency and/or frequency between bursts could yield more optimal results, and it is expected that extrapolation could be used to predict those values at least in part, with focus particularly nearby those areas where pronounced effects already have been observed from the FIG. 20A data, as mapped to the graphs shown in FIGS. 21-23.

Yet another surprising and unexpected development was the discovery that only a relatively small number of pulses could generate significant and long-lasting effects in MEP amplitude response, comparable to much longer TMS treatment protocols currently being employed. Conventional TMS protocols typically involve several thousand pulses, delivered over a period of perhaps 20-30 minutes. The shortest TMS delivery sequences used for clinical purposes in humans that have been reported are generally above 300 pulses for TBS and above 1200 pulses for tonic stimulation. Most TBS treatments typically use some multiple of 300 pulses, and most tonic treatments usually use some multiple of 100 pulses. It was discovered, however, that artificial stimuli of only a small number of pulses, in the range of 6 to 39 pulses (although perhaps as low as 3 or 4 pulses), could result in significant MEP amplitude changes comparable to the thousands of pulses currently being delivered in conventional treatments—particularly if delivered at the optimal pulse frequency and burst repetition frequency, with the proper number of pulses per burst. Indeed, the data in the chart of FIG. 20A was obtained using between 12 and 20 pulses, and yet showed very significant MEP amplitude changes—more so in most cases than conventional burst treatments.

Figure 24:
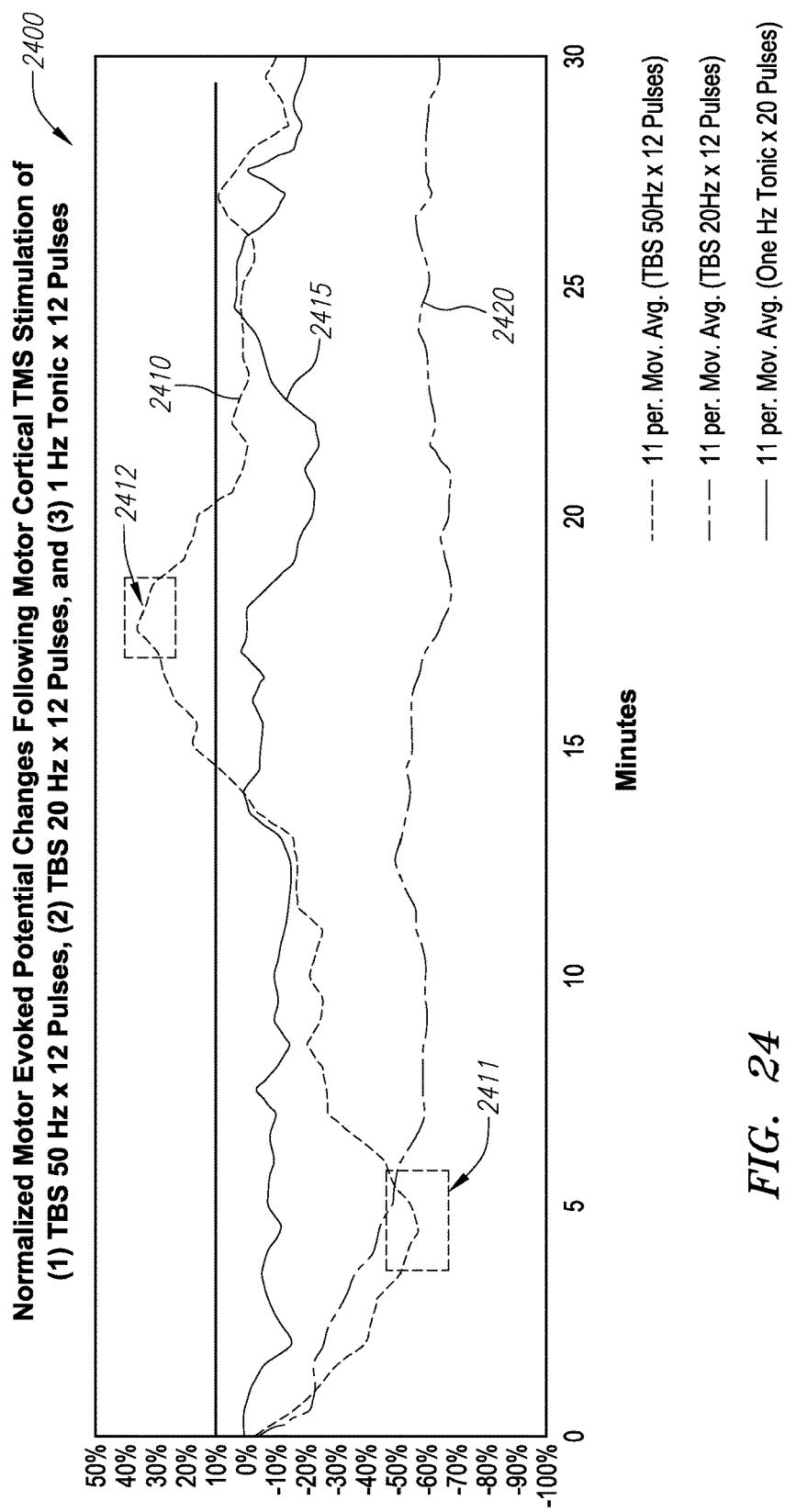
FIG. 24 is a graph illustrating normalized motor evoked potential changes following motor cortical TMS stimulation with short pulse sequences of different types (both burst and tonic).

Quantitative data relating to short pulse sequence protocols is reflected in the graphs and charts of FIGS. 24 through 30A-B. FIG. 24, for example, is a graph 2400 comparing normalized motor evoked potential changes following motor cortical TMS stimulation with short pulse sequences of different types (both burst and tonic). The MEP amplitude changes were measured in a similar manner to the data gathered in connection with FIG. 20A, although they were plotted using a moving average to create the trendlines, and more specifically each point on the graph constitutes an average of the prior eleven raw data points. FIG. 24 shows MEP changes for 12-pulse sequences delivered according to a 5/20/3 pattern, a 5/50/3 pattern, and a 1 Hertz tonic pattern. A first curve 2410 shows the MEP amplitude changes for the 5/50/3 pattern, where a pattern of 12 pulses were delivered over four bursts, with three pulses in each burst, at a burst repetition frequency of 5 Hertz and a pulse frequency within each burst of 50 Hertz. As shown in FIG. 24, the curve 2410 drops over the first five minutes to a region 2411 indicating an MEP amplitude change of about −50%, but then steadily increases over the next 12 minutes until it reaches another region 2412 of about +35%, before tapering off and returning to a value hovering around zero at around 20 minutes, and staying at a range within about ±12% thereafter. Thus, the 5/50/3 pattern appeared to oscillate between negative (inhibitory) and positive (excitatory) MEP response for about 20 minutes, before settling on a very modest inhibitory response level.

A second curve 2415 in FIG. 24 represents the MEP amplitude response to a 12-pulse tonic pulse pattern delivered at 1 Hertz. The MEP response generally remains inhibitory in nature, with the most pronounced effect at about 20 minutes, where it reaches about −22% change in MEP amplitude. However, the third curve 2420 shows a much more significant effect on MEP response level. The third curve 2420 corresponds to the 5/20/3 pattern, where a pattern of 12 pulses were delivered over four bursts, with three pulses in each burst, at a burst repetition frequency of 5 Hertz and a pulse frequency within each burst of 20 Hertz. As shown in FIG. 24, that pattern, despite the small number of total pulses (12), yielded an inhibitory response settling between −60% and −70%, and lasting beyond 30 minutes. This effect is comparable to, if not more significant than, MEP measurements for pulse sequences delivered with thousands of total pulses. Thus, it is apparent from FIG. 24 that certain pulse and burst frequencies can yield MEP responses that are of a duration comparable to convention TMS treatments using thousands of pulses; however, the conventional 5/50/3 pattern is not the pattern that has the most significant effect on MEP response.

Figure 25:
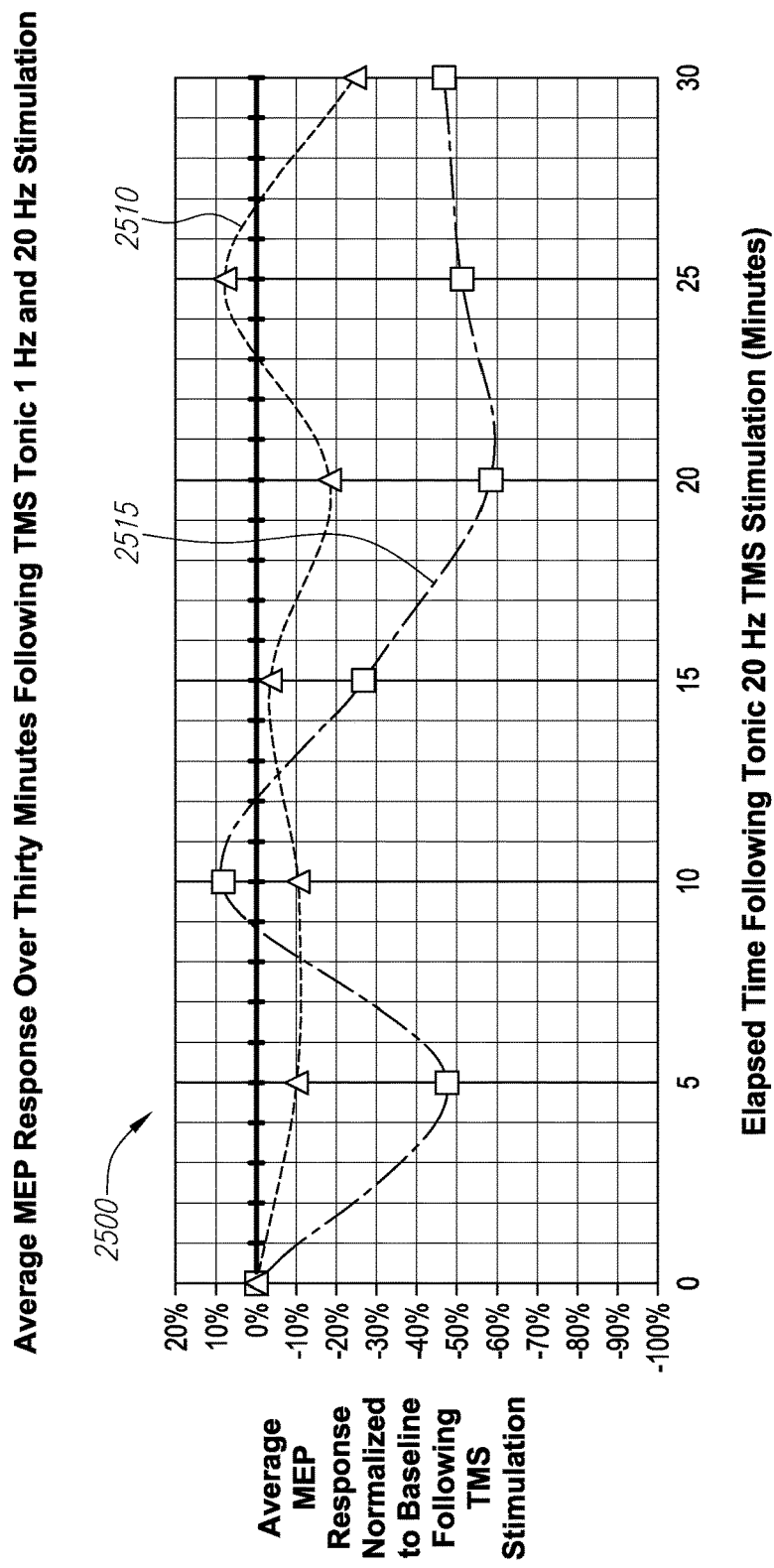
FIG. 25 is a graph comparing motor evoked potential for a period of time following stimulation with theta burst TMS treatment at 20 Hertz as compared to a tonic TMS pulse sequence, both of short duration.

FIG. 25 is a graph 2500 comparing motor evoked potentials for a period of time following stimulation with a tonic TMS pulse sequence as compared to a tonic 1 Hertz sequence, both of short duration. The MEP measurements were taken in a manner similar to that described for FIG. 20A. A first curve 2510 illustrates MEP measurements for up to 30 minutes following an application of 20 pulses at 1 Hertz in a tonic pattern. A second curve 2015 illustrates MEP measurements for up to 30 minutes following an application of 12 pulses at 20 Hertz in a tonic pattern. The first curve 2510 showed only a modest reaction to the 1 Hertz pattern, generally hovering within +10% to −20% in terms of MEP amplitude change. The 20 Hertz tonic pattern, however, after about 20 minutes, settled in a range of about −50% to −60% of MEP amplitude change, showing a significant inhibitory effect. The data in FIG. 25 therefore suggests that the 20 Hertz frequency, by itself, has a substantial effect on MEP amplitude levels and, therefore, a corresponding effect on the brain. The 20 Hertz pulse frequency is therefore likely to yield superior results across a wide variety of patterns, including even tonic patterns. Again, this data was obtained with only very short duration pulse sequences—in the case of the 20 Hertz pattern, only 12 pulses, yet the MEP response lasted beyond 30 minutes.

Figure 26A:
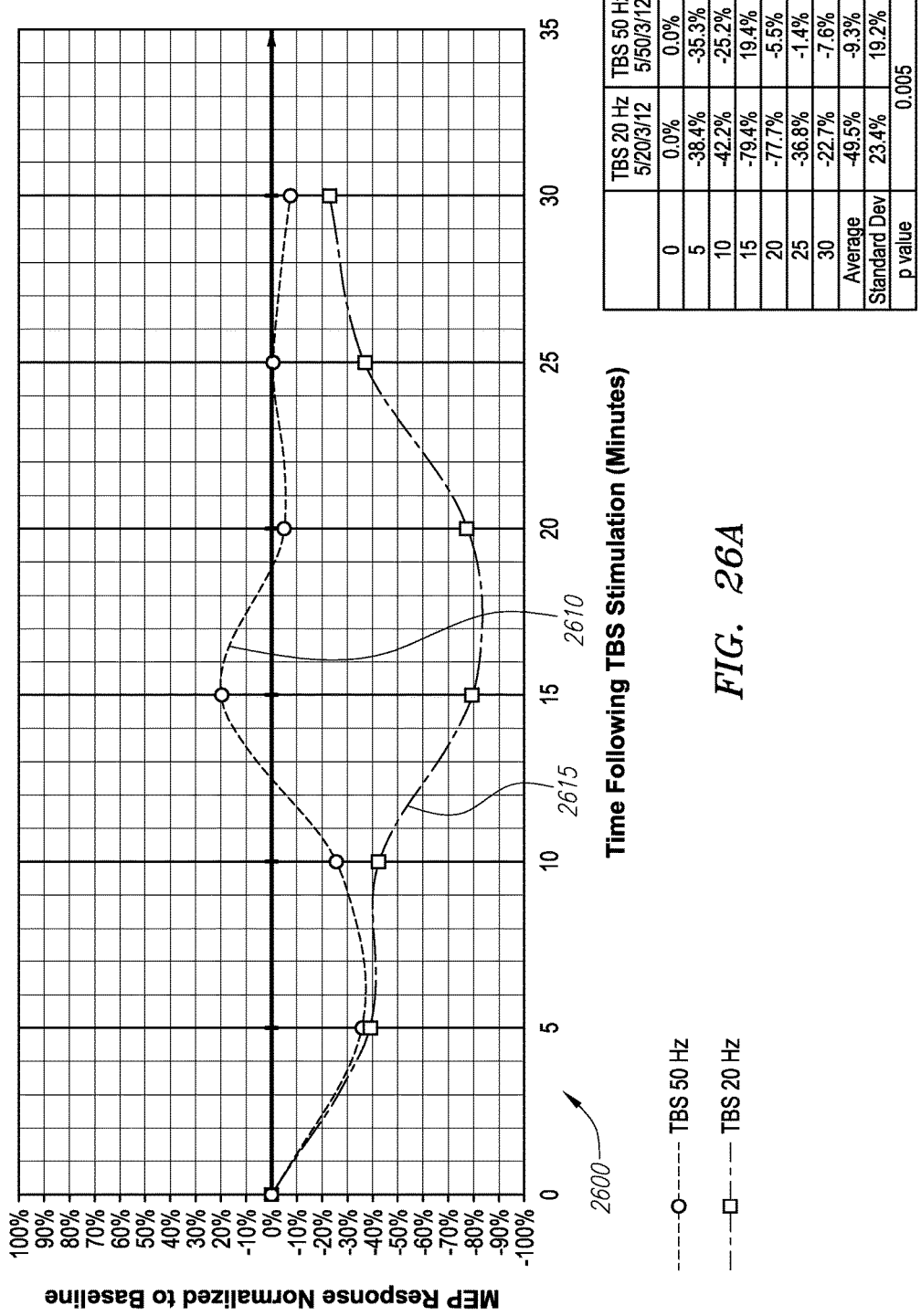
FIG. 26A is a graph comparing responses of motor evoked potential following a relatively short train of pulses of theta burst TMS stimulation at different frequencies.

FIG. 26A is a graph 2600 comparing responses of motor evoked potential following a relatively short train of pulses of theta burst TMS stimulation at different frequencies, measured again in a similar manner to the data obtained in FIG. 20A, and FIGS. 26B, 26C and 26D are charts showing some of the underlying data for the graph of FIG. 26A. FIG. 26A shows MEP changes for 12-pulse sequences delivered according to a 5/20/3 pattern and a 5/50/3 pattern. While FIG. 26A charts responses to the same patterns in FIG. 24, the trendlines are different due to the way in which each data point was determined. For FIG. 26A, one datapoint was graphed for every 5-minute interval by average 5 minutes of data (10 raw data points) into a single graphed point, and then after fitting a polynomial trendline to those fewer points that were separated by 5-minute intervals. A first curve 2610 shows the MEP amplitude changes for the 5/50/3 pattern, where a pattern of 12 pulses were delivered over four bursts, with three pulses in each burst, at a burst repetition frequency of 5 Hertz and a pulse frequency within each burst of 50 Hertz. As shown in FIG. 26, the curve 2610 drops over the first five to ten minutes indicating an MEP amplitude change of about −35%, but then settles after a period of about 20 minutes at a value less than about −10% thereafter. Thus, the 5/50/3 pattern appeared to exhibit some oscillation between negative (inhibitory) and positive (excitatory) MEP response, before settling on a very slight inhibitory response level after 20 minutes. A second trendline 2615 corresponds to the 5/20/3 pattern, where a pattern of 12 pulses were delivered over four bursts, with three pulses in each burst, at a burst repetition frequency of 5 Hertz and a pulse frequency within each burst of 20 Hertz. That pattern, despite the small number of total pulses (12), yielded an inhibitory response exceeding −80% during the period of 15 to 20 minutes after the stimulation, and then gradually returning towards equilibrium, reaching just over −20% after a period of 30 minutes. This effect is generally comparable to pulse sequences delivered with thousands of total pulses.

Figure 27A:
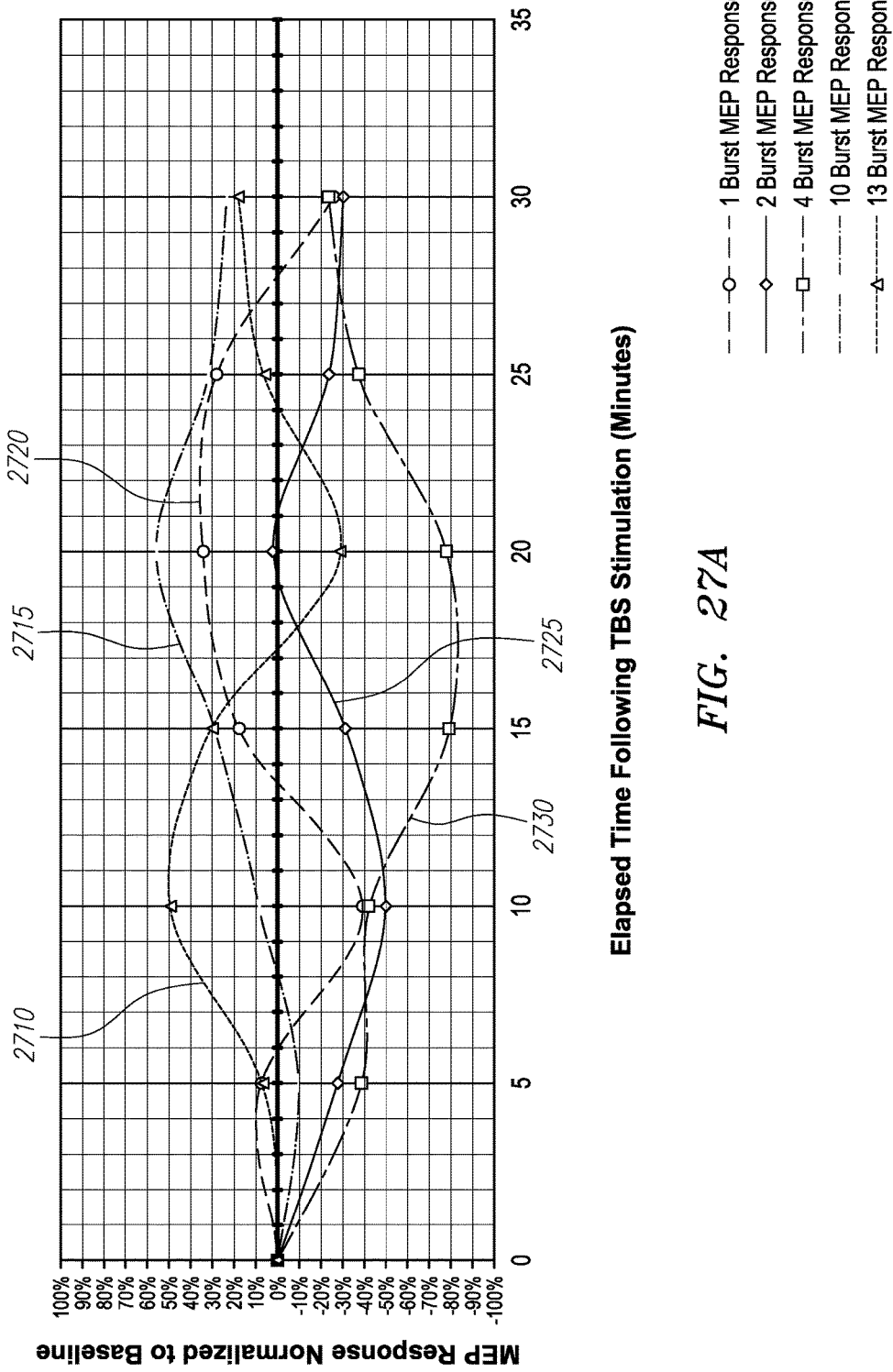
FIG. 27A is a graph comparing normalized changes over a period of time in responses of motor evoked potential following a relatively short train of pulses of theta burst TMS stimulation at 20 Hertz with different numbers of pulses in each burst.

FIG. 27A is a graph 2700 with a set of spline curves showing motor evoked potential changes over time following theta burst TMS stimulation at 20 Hertz applied with different numbers of total pulses. Again, the MEP measurements were made in a manner similar to that described for FIG. 20A, with each single point representing the average of the ten preceding measured points in a given 5-minute interval, and with polynomial trendlines then fit to the data points. FIG. 27B contains the 5-minute average values that were plotted in the graph of FIG. 27A.

In FIG. 27A, each of the trendline curves 2710, 2715, 2720, 2725 and 2730 shows the MEP amplitude changes for the 5/20/3 pattern, where the number of bursts (and hence number of pulses) was varied from 1 to 13 bursts, thus varying the number of applied pulses from 3 to 39, given that there were 3 pulses in each burst. Curve 2720 corresponds to a pulse sequence with one burst (3 pulses total); curve 2725 involved a pulse sequence with two bursts (6 pulses total); curve 2730 involved a pulse sequence with 4 bursts (12 pulses total); curve 2715 involved a pulse sequence with 10 bursts (30 pulses total); and curve 2710 involved a pulse sequence with 13 bursts (39 pulses total). From FIG. 27A, it can be seen that the effect on MEP amplitude changes over the duration of 30 minutes varied depending upon the number of bursts (or pulses) applied, and that furthermore, the same 5/20/3 pattern of pulses could produce either an excitatory or inhibitory effect. The greatest inhibitory effect was observed for the 4-burst (12 pulse) sequence, as reflected in curve 2730, and furthermore the MEP response remained inhibitory throughout the 30 minute duration. This is consistent with the observation in FIG. 20A that the 5/20/3 pattern with 12-pulses produces a pronounced inhibitory effect.

Figure 28:
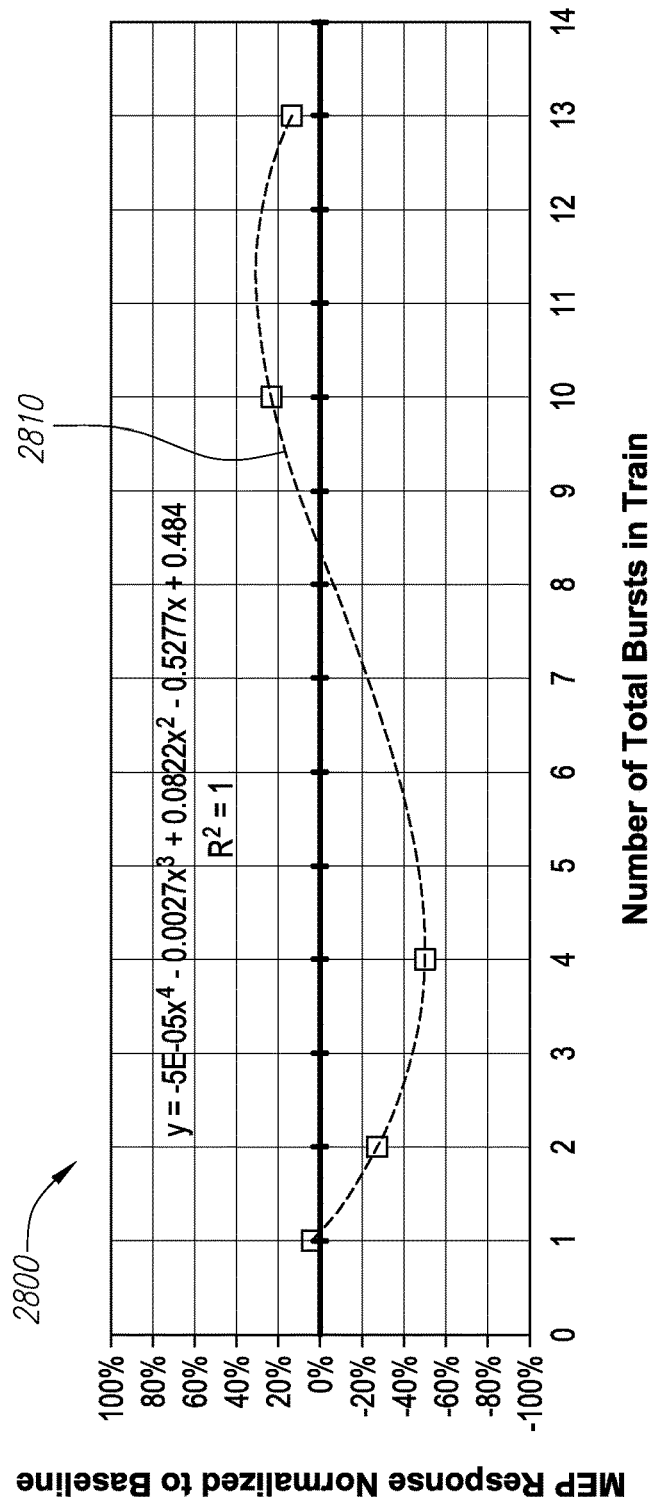
FIG. 28 is a graph comparing net normalized changes in responses of motor evoked potential, averaged over a period of time, following a relatively short train of pulses of theta burst TMS stimulation at 20 Hertz with different numbers of pulses in each burst.

FIG. 28 is a graph comparing the results shown in FIGS. 27A-B in a summary format, illustrating net normalized changes in responses of motor evoked potential, averaged over a period of time, following a relatively short train of pulses of theta burst TMS stimulation at 20 Hertz with different numbers of pulses in each burst. As shown in FIG. 28, the greatest efficacy was observed for a burst train of four in length (12 total pulses), and the efficacy decreased beyond that point.

Figure 29:
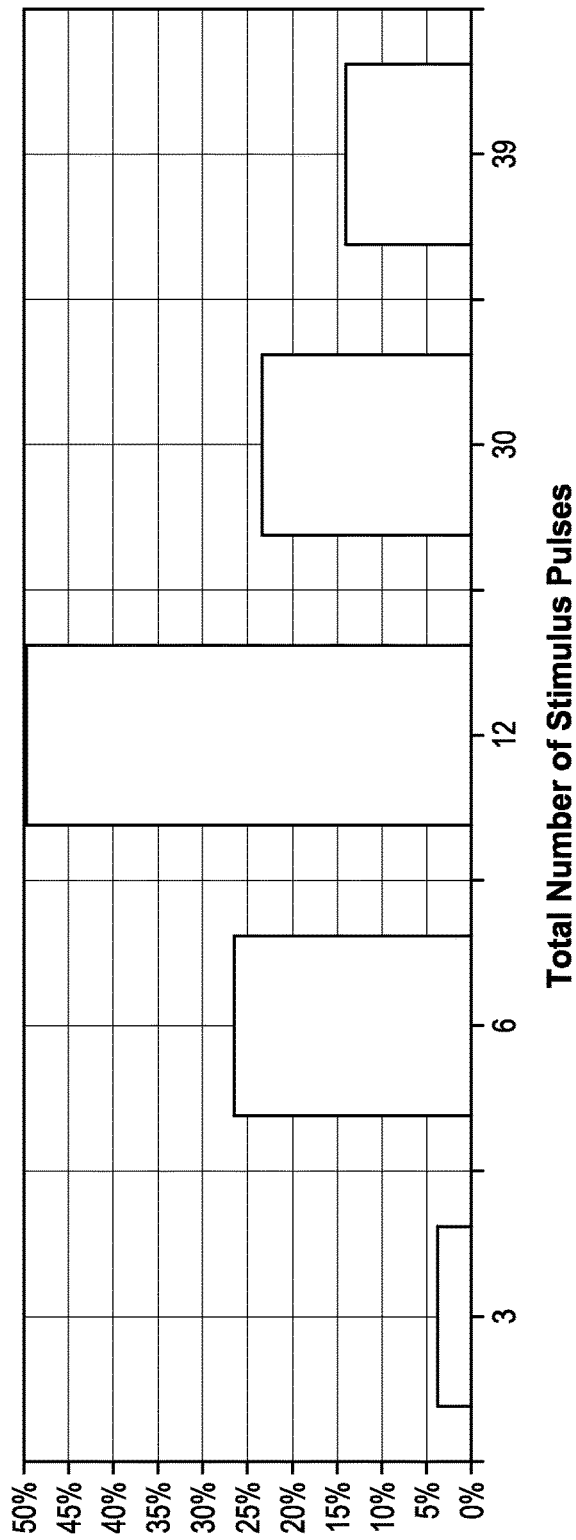
FIG. 29 is a chart comparing the net efficacy of short train of pulses of theta burst TMS stimulation at 20 Hertz with different numbers of bursts or pulses, as measured by responses of motor evoked potential using polarity independent measurement techniques.
Figure 30:
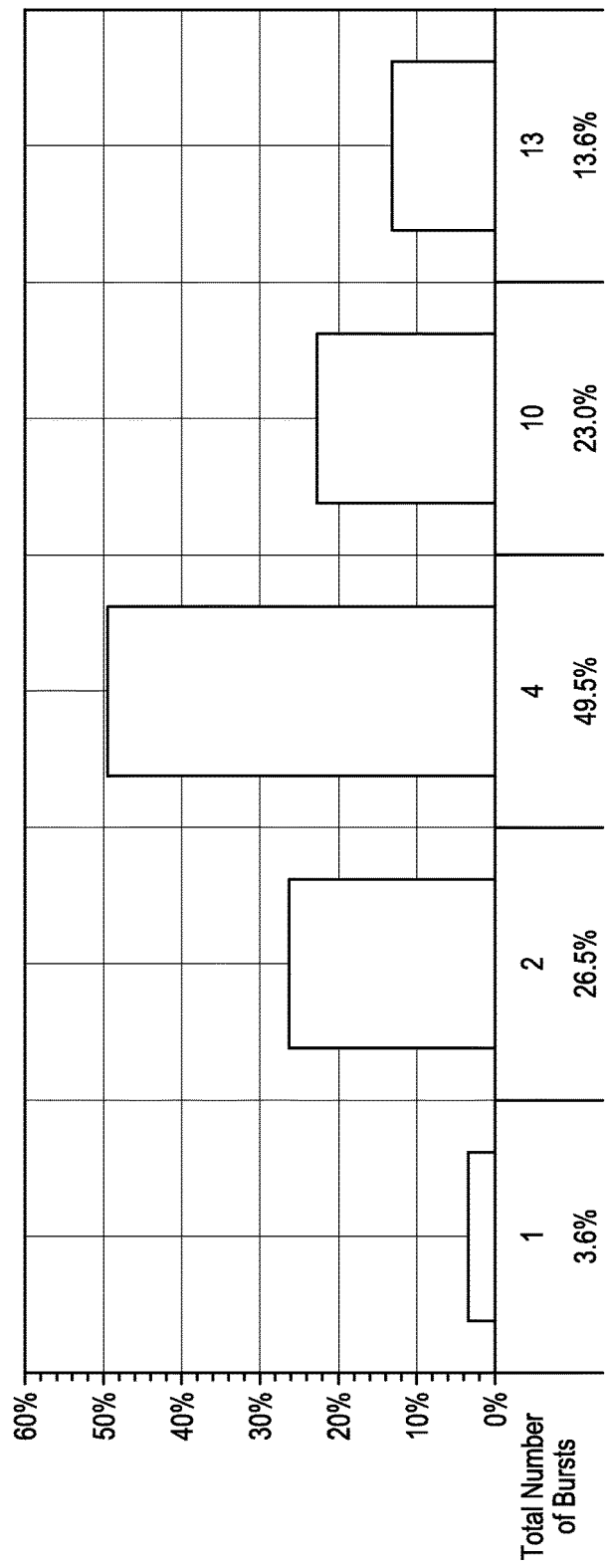
FIG. 30 is a chart illustrating the data in FIG. 29 using the number of bursts instead of number of pulses in short duration treatments of theta burst TMS stimulation at 20 Hertz using different numbers of bursts or pulses.

FIGS. 29 and 30 are charts illustrating the data of FIGS. 27 and 28 from different standpoints. Both characterize the and compare the net efficacy of short train of pulses of theta burst TMS stimulation at 20 Hertz (using the 5/20/3 pattern) with different numbers of total bursts or pulses, as measured by responses of motor evoked potential using polarity independent measurement techniques. In FIG. 29, it can be seen that the 20 Hertz therapy delivered with 12 total pulses provided a significantly greater MEP response than when using other numbers of pulses, either less than or greater than 12. FIG. 30 is a chart illustrating the same data as in FIG. 29 but using the number of bursts instead of number of pulses in short duration treatments of theta burst TMS stimulation at 20 Hertz. The same relative magnitude of the bars in the chart of FIG. 30 appears, and in addition, the net efficacy value is also shown—varying from 3.6% for a therapy of only 3 pulses, to a maximum of 49.5% MEP amplitude change for a therapy of 12 pulses (four bursts) in total, before dropping back down.

Among other things, the data presented and summarized in the graphs and charts of FIGS. 11-30 indicate that a variety of potentially more powerful and effective TMS treatments exist, using different treatment parameters and specifically including at least different burst repetition frequencies, pulse delivery frequencies, pulse/burst ratios, and total number of bursts/pulses. Based on the information presented and summarized in those graphs and charts, it can be concluded that burst stimulation therapy or treatment may deliver unexpectedly superior results with a burst repetition frequency in the range of 0.1-150 Hz, and more preferably a range of 3-8 Hz (theta range or slightly lower), even more preferably a range of 4-7 Hz, and most preferably in a range of approximately 5-6 Hz, and a pulse frequency greater than 0.2 Hz but less than 300 Hz, and more preferably in the range of 14-28 Hz, and even more preferably at approximately 20 Hz. Particular stimulation patterns, such as those involving a pulse frequency in the range of 19-21 Hz for 3 pulses/burst patterns or 22-26 Hz for 2 pulse/burst patterns, may also yield surprisingly efficacious results. Furthermore, it can be concluded that delivery of TMS therapies using pulse/burst frequency ratios that are preferably between 3 and 5, and most preferably in the range in and around 4, are likely to be most efficacious. A number of pulses per burst in these cases is preferably in the range of 2-1000, and more preferably in a range of 2-4 pulses/burst, and most preferably at either 2 pulses/burst or 3 pulses/burst.

In addition to the parameters described in FIG. 20A that could be varied, there are also a number of other parameters that could possibly be varied, and included in various predetermined regimens or protocols. For example, the stimulation parameters in the predetermined regimens or parameters may include different settings relating to electrical current waveform shapes, pulse amplitude variations, pulse sequences that are not based on specific frequency patterns, simultaneous and/or sequential electromagnetic stimulation from more than one TMS coil or from more than one neuromodulation device, variable pulse polarities, analog stimulation unrelated to specific pulse patterns, and neuromodulation paired with sensory or other types of stimuli, all of which represent parameter variations that have been applied or may be applied in the future. The novel pulse parameters described herein are neither invalidated by nor inconsistent with other concomitant parameter variations where neuromodulatory stimuli are modified in ways in ways including but not limited to the above examples.

Another consequence of the discovery that different parameters and combinations have markedly different effects on MEP amplitude changes and therapeutic effectiveness (such as effects on BDI-II scores) is that the door becomes open to the possibility of selecting predetermined therapy regimens for different patient conditions or patient types, using the most efficacious parameter set that has been determined through experience to be effective for the particular patient condition or type. Likewise, that discovery, along with the discovery that short bursts provide substantial information about the patient's reaction to particular parameter combinations, allow for diagnostic and treatment techniques involving rapid searching for and detecting of TMS parameter combinations that are likely to be most effective for a particular patient. In other words, using a number of different short burst sequences applied to a patient, along with MEP response detection (or other suitable response monitoring), in either a manual or automated process, a customized therapy can be determined for a particular patient involving a unique set of TMS therapy parameters. The patient's individualized treatment parameters can be saved and stored by the system for later use for that patient. Further, it can be saved in a database of treatment parameters, and used in combination with the determined individualized parameters for other patients either to establish a particular regimen or a search starting point for patients with similar conditions.

Figure 8A:
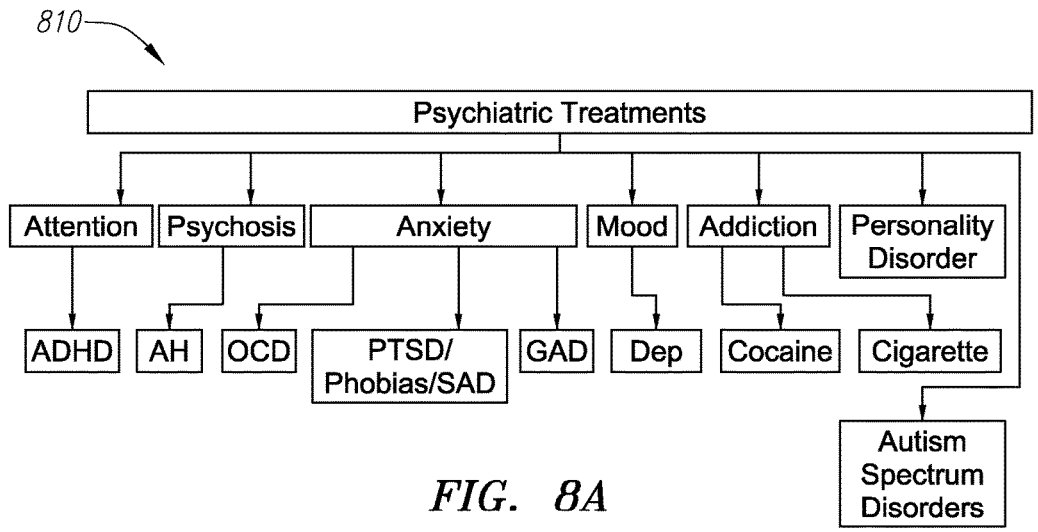
FIG. 8A is a chart providing an illustrative classification of psychiatric conditions that may be treated according to the novel apparatus and methods disclosed herein.
Figure 8B:
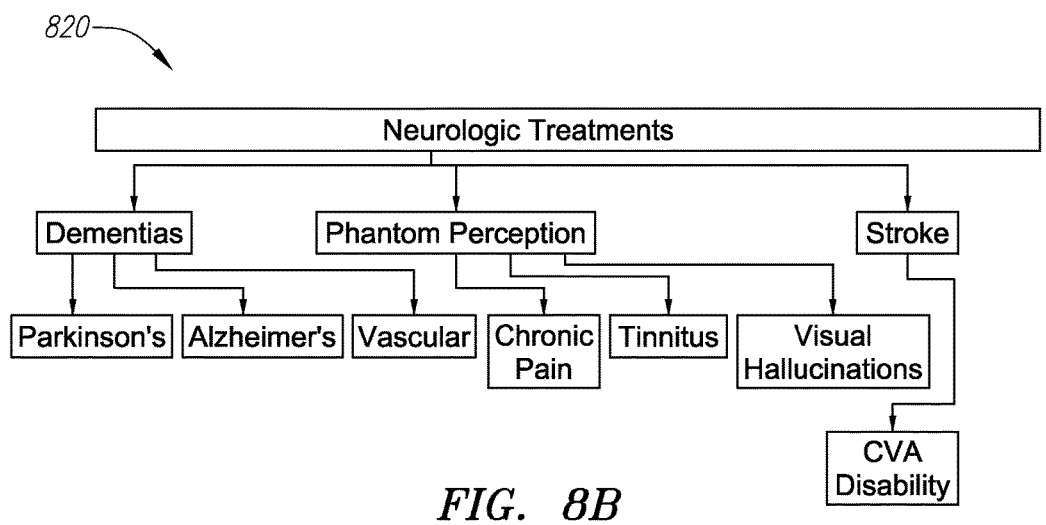
FIG. 8B is a chart providing an illustrative classification of neurologic conditions that may be treated according to the novel apparatus and methods disclosed herein.
Figure 8C:
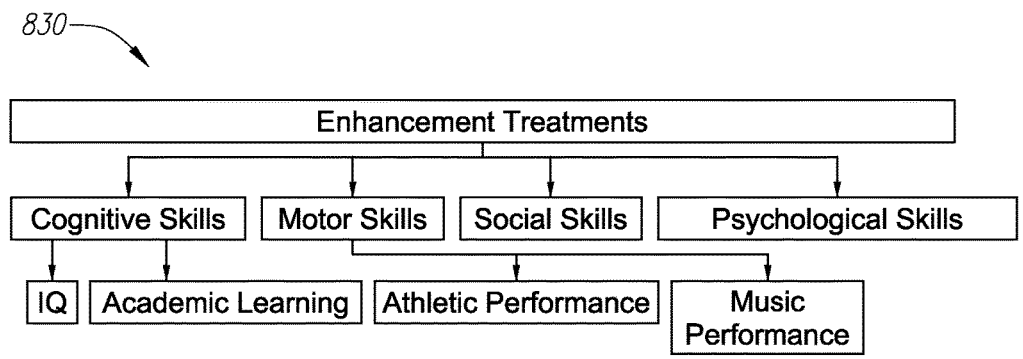
FIG. 8C is a chart providing an illustrative classification of skills or performance traits that potentially may be enhanced according to the novel apparatus and methods disclosed herein.

The pulse therapy treatments described herein are believed to be applicable to a wide variety of settings, and wherever the efficacy of stimulation depends in whole or part on the neurological response of the patient, and more particularly where brain stimulation techniques are involved. Some of the areas of applicability are summarized in FIGS. 8A-8C. Furthermore, the methods and techniques are not limited to treatment of disorders, but also may be used for enhancement of a patient's physical or cognitive functions. FIG. 8A is a chart providing an illustrative classification of some examples of the psychiatric conditions that may be treated according to the novel apparatus and methods disclosed herein. FIG. 8B is a chart providing an illustrative classification of some examples of neurologic conditions that may be treated according to the novel apparatus and methods disclosed herein. FIG. 8C is a chart providing an illustrative classification of skills or performance traits that potentially may be enhanced according to the novel apparatus and methods disclosed herein. These are simply examples of the wide applicability that the invention(s) disclosed herein are expected to have.

4. Exemplary Applications to Medical Conditions

Example A

Depression (Encompassing Unipolar, Bipolar I and II Depressions)

Patients with severe depression may also be successfully treated according to the disclosed exemplary embodiments, as described earlier. In particular, four consecutive unipolar depressed treatment-refractory patients received neuro-navigated TMS. Weekly Beck Depression Inventory II (BDI-II) rating scales assessed depression severity. Two patients with significant anxiety began treatment with bilateral TBS-50 Hz (bursts of three 50 Hz pulses at 5 Hz intervals) and two patients began with unilateral followed by bilateral TBS-50 Hz. After non-remission to TBS-50 Hz, all patients received unilateral TBS-20 Hz (bursts of three 20 Hz pulses at 5 Hz intervals) followed by, in the case of persistent non-remission, bilateral TBS-20 Hz. Protocols were switched if two consecutive weeks passed without BDI-II score improvement. The LDLPFC portions of the TMS were paired with personally selected, emotionally uplifting music administered using headphones. Treatment was well tolerated without adverse effects. Following TBS-50 Hz (mean 38.3 sessions), one patient responded (BDI-II decrease>50%) but none remitted, with average BDI-II scores decreasing from 33.3 to 19.3 (p=0.015). However, following TBS-20 Hz (mean 39.8 sessions), all four patients remitted with average BDI-II scores decreasing from 26.0 to 6.8 (p=0.037). Remissions persisted through follow-up (mean of 8 months) without additional treatment. All patients dramatically improved and entered remission (full recovery) even though they had all lost hope of recovery until having treatment using the disclosed exemplary embodiments. Such a result is surprising considering that many of the treated patients had undergone multiple extensive medication trials for decades with no resolution of their symptoms, and some had also failed to improve with ECT. By way of comparison, the two largest multicenter randomized controlled trials for TMS and depression treated over 500 patients. Both found that only 10-15% of patients remitted after TMS treatment, and these patients were much less ill than the patients discussed above (O'Reardon et al. 2007; George et al. 2010).

Example B

Tinnitus

The stimulation protocols and methods discussed herein may be applied to treat neurologic conditions such as tinnitus. When treating tinnitus, the coil may initially be placed in position over the LDLPFC at Talairach coordinates corresponding to Brodmann Area 46. A preconfigured dynamic or fixed excitatory parameter set could be implemented, such as the TBS-20 Hz protocol applied intermittently with 2 seconds "on" and 8 seconds "off". The sensory system would pair the treatment with a sound file. The sound file could consist of white noise notched around the tinnitus frequency, for example, which would activate neurons on the tonotopic map surrounding the tinnitus frequency, in essence pairing activity in specific cells with the LDLPFC treatment. A fixed number of bursts may be used, ranging from 1 to 1800. If the dynamic parameter regulation is applied to the burst number, for example, stimulation would continue until the activation level of a biomarker related to neuroplasticity reached a critical level as determined by real-time QEEG brain maps or swLoreta imaging. Then the coil would be placed over Brodmann Area 22 in the auditory cortex for the next treatment. A preconfigured static or dynamic inhibitory parameter set, such as continuous 6/20/3 stimulation would then be selected. A fixed number of bursts may be used, ranging from 1 to 1200. If the dynamic parameter regulation is applied to the burst number, for example, stimulation would continue until the activation level of a biomarker related to tinnitus activity decreased to a critical level as determined by real-time QEEG measurements.

Example C

Auditory Hallucinations

Even in the most severe of cases and after all prior efforts fail, patients may be successfully treated for auditory hallucinations using the exemplary embodiments of the disclosed subject matter herein. The inhibitory treatment would occur over the supramarginal gyms in the parietal region of the dominant hemisphere. A preconfigured inhibitory parameter set, such as the 5/20/3 protocol, could be used with dynamic or fixed parameters as described above.

Example D

Generalized Anxiety Disorder

Patients with severe GAD may also be successfully treated using the disclosed embodiments. In particular, RDLPFC inhibitory treatment may be applied alone, without a LDLPFC treatment, in a similar manner to that shown above in the RDLPFC portion of the treatment for depression.

Example E

General Application

Various stimulation techniques as described herein may find useful application in non-invasive brain stimulation or neurological stimulation; however, they are by no means limited to such applications. Rather they may be employed in a variety of different contexts or environments, and may be used, for example, wherever artificial stimuli are used to evoke a neural response.

In one aspect of the embodiments disclosed herein, a therapeutic device is provided for delivering artificial stimulating pulses to a human subject, the device comprising a set of stored stimulation parameters determining a theta burst stimulation sequence, the set of stored stimulation parameters including at least a pulse frequency parameter selected in a range from 12 to 40 Hertz and a burst repetition frequency parameter having a value that is different than the pulse frequency parameter; and a neurological stimulation device configured to stimulate the human subject's brain or nervous system by repetitively emitting electromagnetic pulses according to the set of stored stimulation parameters, the electromagnetic pulses arranged in a plurality of bursts each comprising at least two electromagnetic pulses spaced according to the pulse frequency parameter, the bursts being spaced according to the burst repetition frequency parameter. The burst repetition frequency parameter may be selected in a range from 3 to 8 Hertz; the pulse frequency parameter may be selected in a range from 16 to 28 Hertz; and/or the burst repetition frequency parameter may be selected in a range from 4 to 7 Hertz.

In certain embodiments, the pulse frequency parameter may be selected in a range from 19 to 21 Hertz, the number of electromagnetic pulses per burst may be three, and, optionally, the burst repetition frequency parameter may be selected in a range from 5 to 6 Hertz. In other embodiments, the pulse frequency parameter may be selected in a range from 22 to 26 Hertz, the number of electromagnetic pulses per burst may be two, and, optionally, the burst repetition frequency parameter may be selected in the range from 5 to 6 Hertz. The burst repetition frequency parameter may be selected so that the ratio of the pulse frequency parameter to the burst repetition frequency parameter is in the range from 3 to 5. The bursts may be arranged in a plurality of trains, each train comprising a plurality of said bursts and being separated by an inter-train interval during which no electromagnetic pulses are delivered. Each train may have the same number of bursts, and the inter-train interval may be longer than the duration of each train. The neurological stimulation device may comprise a transcranial magnetic stimulation (TMS) device configured to non-invasively stimulate the human subject's central or peripheral nervous system by repetitively emitting the electronic pulses in the form of a transient electromagnetic field generated from one or more energized coils, or may be selected from the group of: a vagus nerve stimulation device, a peripheral nerve stimulation device, a deep brain stimulation device, a peripheral nerve field stimulation device, a cortical stimulation device, a transcutaneous vagal nerve stimulation device, a transcutaneous electrical nerve stimulation device, an electroconvulsive therapy device, a transcranial direct current stimulation device, a transcranial alternating current device, a transcranial random noise device, a trigeminal nerve stimulation device, or a paired associative stimulation device.

The set of stored stimulation parameters may further comprise a number of pulses per burst parameter, a number of bursts per train parameter, and one or more train length parameters, wherein each train comprises the same number of plurality of bursts. The set of stored stimulation parameters may be entered via a user interface and temporarily stored during a treatment session involving delivery of the electromagnetic pulses to the human subject, and thereafter discarded. The set of stored stimulation parameters may be selected so as to induce an inhibitory neural response in the human subject, to induce an excitatory neural response in the human subject, or to augment the response to another central or peripheral nervous system treatment. The neurological stimulation device may further comprise a pulse command generator responsive to the stimulation parameters for generating pulse commands according to the pulse frequency parameter and the burst repetition frequency parameter; and a pulse delivery mechanism responsive to the pulse commands generated by the pulse command generator, for generating a central or peripheral nerve stimulating pulse corresponding to each pulse command. The pulse frequency parameter may be stored as a time duration corresponding to the frequency represented by the pulse frequency parameter, and the burst repetition frequency parameter may be stored as a time duration corresponding to the frequency represented by the burst repetition frequency parameter.

In another aspect of the embodiments disclosed herein, a therapeutic system is provided comprising a set of stored stimulation parameters determining a burst stimulation sequence, the set of stored stimulation parameters including at least a pulse frequency parameter selected in a range from 12 to 40 Hertz and a burst repetition frequency parameter having a value that is different than the pulse frequency parameter; a pulse command generator responsive to the set of stored stimulation parameters, configured to output pulse commands with a pattern based upon the set of stored stimulation parameters including the pulse frequency parameter and the burst repetition frequency parameter; and a non-invasive brain stimulation device response to the pulse commands, configured to stimulate the human subject's brain by repetitively emitting electromagnetic pulses according to the pattern of pulse commands, the electromagnetic pulses arranged in a plurality of bursts each comprising at least two electromagnetic pulses spaced according to the pulse frequency parameter, the bursts being spaced according to the burst repetition frequency parameter.

The burst repetition frequency parameter may be selected in a range from 3 to 8 Hertz, and more preferably in the range from 4 to 7 Hertz, and most preferably in the range of 5 to 6 Hertz; and the pulse frequency parameter may be selected in a range from 16 to 28 Hertz. In certain embodiments, the pulse frequency parameter may be selected in a range from 19 to 21 Hertz, the burst repetition frequency parameter may be selected in a range from 4 to 7 Hertz, and/or the number of electromagnetic pulses per burst may be three. In other embodiments, the pulse frequency parameter may be selected in a range from 22 to 26 Hertz, the burst repetition frequency parameter may be selected in a range from 4 to 7 Hertz, and/or the number of electromagnetic pulses per burst may be two. The burst repetition frequency parameter may be selected in a range from 5 to 6 Hertz, with the number of electromagnetic pulses per burst being two. The burst repetition frequency parameter may be selected so that the ratio of the pulse frequency parameter to the burst repetition frequency parameter is in the range from 3 to 5. The bursts may be arranged in a plurality of trains, each train comprising a plurality of said bursts and being separated by an inter-train interval during which no electromagnetic pulses are delivered. Each train may have the same number of bursts, and the inter-train interval may be longer than the duration of each train.

The non-invasive brain stimulation device may comprise a transcranial magnetic stimulation (TMS) device configured to stimulate the human subject's brain by repetitively emitting the electronic pulses in the form of a transient electromagnetic field generated from one or more energized coils. The set of stored stimulation parameters may further comprise a number of pulses per burst parameter, a number of bursts per train parameter, and a train length parameter, wherein each train comprises the same number of plurality of bursts. The set of stored stimulation parameters may be entered via a user interface and temporarily stored during a treatment session involving delivery of the electromagnetic pulses to the human subject, and thereafter discarded. The set of stored stimulation parameters may be selected so as to induce an inhibitory neural response in the human subject, an excitatory neural response in the human subject, or to augment the response to another central or peripheral nervous system treatment.

In another aspect of the embodiments disclosed herein, a therapeutic device for delivering artificial stimulating pulses to a human subject is provided, comprising a plurality of pre-stored therapy regimens, one or more of the pre-stored therapy regimens comprising a set of associated stimulation parameters determining a burst stimulation sequence, the stimulation parameters including parameters defining a pulse frequency and a burst repetition frequency; and a neurological stimulation device configured to stimulate the human subject's brain or nervous system, in response to a selected pre-stored therapy regimen, by repetitively emitting electromagnetic pulses according to the set of stimulation parameters associated with the selected pre-stored therapy regimen, the electromagnetic pulses arranged in a plurality of bursts each comprising at least two electromagnetic pulses spaced according to said pulse frequency, and the bursts being spaced according to said burst repetition frequency.

The therapeutic device may further comprise a display for graphically displaying stimulation parameters of the pre-stored therapy regimens in response to a user request, and a user input for receiving a user selection of one of the pre-stored therapy regimens. The user input may be configured to receive user commands to override one or more stimulation parameters of a selected pre-stored therapy regimen or to bypass the pre-stored therapy regimens through user-entered stimulation parameters. In response to the user selection of one of the pre-stored therapy regimens, the neurological stimulation device may load the stimulation parameters from the selected pre-stored therapy regimen into one or more counters and timers, according to which the neurological stimulation device repetitively generates and emits the electromagnetic pulses in a plurality of bursts to stimulate the patient's brain or nervous system. In response to a save command entered via the user input, a new set of stimulation parameters may be saved and stored in association with a new therapy regimen that is thereafter available for retrieval and use as one of the pre-stored therapy regimens. The new set of stimulation parameters may be obtained from values entered via the user input, or by using an automated search routine executed by the neurological stimulation device using at least two different sets of stimulation parameters. The automated search routine executed by the neurological stimulation device may involve repetitively emitting electromagnetic pulses according to at least two different sets of stimulation parameters, and the therapeutic device may further include a measurement device for measuring the human subject's response to the delivery of electromagnetic pulses according to the at least two different sets of stimulation parameters.

The neurological stimulation device may comprise a transcranial magnetic stimulation (TMS) device configured to non-invasively stimulate the human subject's brain or nervous system by repetitively emitting the electronic pulses in the form of a transient electromagnetic field generated from one or more energized coils. The measurement device may comprise an EEG sensor, an EMG sensor, an infrared sensor, or an optical activity sensor, and may be configured to measure changes in the human subject's motor evoked potential (MEP).

In certain embodiments, one or more of the pre-stored therapy regimens may be customized for individual human subjects and stored in association with information identifying the associated individual human subject. At least one of the pre-stored therapy regimens may comprise either (i) a set of stimulation parameters defining a pulse frequency in a range from 19 to 21 Hertz and a number of pulses per burst equal to three, or (ii) a set of stimulation parameters defining a pulse frequency in a range from 22 to 26 Hertz and a number of pulses per burst equal to two. At least one of the pre-stored therapy regimens comprises both (i) a set of stimulation parameters defining a pulse frequency in a range from 19 to 21 Hertz, a burst repetition frequency in a range from 4 to 7 Hertz, and a number of pulses per burst equal to three, and (ii) a set of stimulation parameters defining a pulse frequency in a range from 22 to 26 Hertz, a burst repetition frequency in a range from 4 to 7 Hertz, and a number of pulses per burst equal to two.

The neurological stimulation device may comprise a device selected from the group of: a vagus nerve stimulation device, a peripheral nerve stimulation device, a deep brain stimulation device, a peripheral nerve field stimulation device, a cortical stimulation device, a transcutaneous vagal nerve stimulation device, a transcutaneous electrical nerve stimulation device, an electroconvulsive therapy device, a transcranial direct current stimulation device, a transcranial alternating current device, a transcranial random noise device, a trigeminal nerve stimulation device, a multi-coil transcranial magnetic stimulation device, a paired associative stimulation device, or a combination of the aforementioned devices.

The set of stored stimulation parameters may further comprise a number of pulses per burst parameter, a number of bursts per train parameter, and a train length parameter, wherein each train comprises the same number of plurality of bursts. The set of stored stimulation parameters may be selected so as to induce an inhibitory neural response in the human subject, an excitatory neural response in the human subject, or to augment the response to another central or peripheral nervous system treatment. The neurological stimulation device may comprise a pulse command generator responsive to the stimulation parameters from the selected pre-stored therapy regimen for generating pulse commands according to the pulse frequency and the burst repetition frequency indicated by the stimulation parameters; and a brain-stimulation pulse delivery mechanism responsive to the pulse commands generated by the pulse command generator, for generating a non-invasive central or peripheral nervous system stimulating pulse corresponding to each pulse command. The pulse frequency may be stored as a pulse spacing time duration parameter corresponding to the pulse frequency, and the burst repetition frequency may be stored as a burst spacing time duration parameter corresponding to the burst repetition frequency.

In another aspect of the embodiments disclosed herein, a therapeutic system for delivering non-invasive artificial stimulating pulses to a human subject's brain is provided, the device comprising a plurality of pre-stored therapy regimens, one or more of the pre-stored therapy regimens comprising a set of associated stimulation parameters determining a burst stimulation sequence, the stimulation parameters including parameters defining a pulse frequency and a burst repetition frequency; a pulse command generator responsive to a selected one of the pre-stored therapy regimens, configured to output pulse commands with a pattern based upon the set of associated stimulation parameters of the selected pre-stored therapy regimen including the parameters defining the pulse frequency and burst repetition frequency; and a non-invasive brain stimulation device response to the pulse commands, configured to stimulate the human subject's brain by repetitively emitting electromagnetic pulses according to the pattern of pulse commands, the electromagnetic pulses arranged in a plurality of bursts each comprising electromagnetic pulses spaced according to the pulse frequency, the bursts being spaced according to the burst repetition frequency.

The therapeutic system may further comprise a display for graphically displaying stimulation parameters of the pre-stored therapy regimens in response to a user request, and a user input for receiving a user selection of one of the pre-stored therapy regimens. The user input may be configured to receive user commands to override one or more stimulation parameters of a selected pre-stored therapy regimen or to bypass the pre-stored therapy regimens through user-entered stimulation parameters. In response to the user selection of one of the pre-stored therapy regimens, the non-invasive brain stimulation device may load the stimulation parameters from the selected pre-stored therapy regimens into one or more counters and timers, according to which the non-invasive brain stimulation device repetitively generates and emits the electromagnetic pulses in a plurality of bursts directed to the patient's brain. In response to a save command entered via the user input, a new set of stimulation parameters may be saved and stored in association with a new therapy regimen that is thereafter available for retrieval and use as one of the pre-stored therapy regimens. The new set of stimulation parameters may be obtained from values entered via the user input, or using an automated search routine executed by the non-invasive brain stimulation device using at least two different sets of stimulation parameters, wherein at least one of the pulse frequency and the burst repetition frequency is varied. The automated search routine may involve repetitively emitting electromagnetic pulses according to the at least two different sets of stimulation parameters, and the therapeutic device may further comprises a measurement device for measuring the human subject's response to the delivery of electromagnetic pulses according to the at least two different sets of stimulation parameters.

The non-invasive brain stimulation device may comprise a transcranial magnetic stimulation (TMS) device configured to non-invasively stimulate the human subject's brain by repetitively emitting the electronic pulses in the form of a transient electromagnetic field generated from one or more energized coils. The measurement device may comprise an EEG sensor, an EMG sensor, an optical sensor or an infrared sensor, and may be configured to measure changes in the human subject's motor evoked potential (MEP).

One or more of the pre-stored therapy regimens may be customized for individual human subjects and stored in association with information identifying the associated individual human subject. At least one of said pre-stored therapy regimens comprises either (i) a set of stimulation parameters defining a pulse frequency in a range from 19 to 21 Hertz and a number of pulses per burst equal to three, or (ii) a set of stimulation parameters defining a pulse frequency in a range from 22 to 26 Hertz and a number of pulses per burst equal to two. At least one of said pre-stored therapy regimens comprises both (i) a set of stimulation parameters defining a pulse frequency in a range from 19 to 21 Hertz, a burst repetition frequency in a range from 4 to 7 Hertz, and a number of pulses per burst equal to three, and (ii) a set of stimulation parameters defining a pulse frequency in a range from 22 to 26 Hertz, a burst repetition frequency in a range from 4 to 7 Hertz, and a number of pulses per burst equal to two. The set of stored stimulation parameters may further comprise a number of pulses per burst parameter, a number of bursts per train parameter, and one or more train length parameters, wherein each train comprises the same number of plurality of bursts. The set of stored stimulation parameters may be selected so as to induce an inhibitory neural response in the human subject, an excitatory neural response in the human subject, or augment the response to another central or peripheral nervous system treatment. The pulse frequency may be stored as a pulse spacing time duration parameter corresponding to the pulse frequency, and the burst repetition frequency may be stored as a burst spacing time duration parameter corresponding to the burst repetition frequency.

In another aspect of the embodiments disclosed herein, a method for delivering artificial stimulating pulses to a human subject using a therapeutic neurological stimulation device is provided, the method comprising pre-storing a plurality of therapy regimens in a durable memory, one or more of the pre-stored therapy regimens comprising a set of associated stimulation parameters determining a burst stimulation sequence, the stimulation parameters including parameters defining a pulse frequency and a burst repetition frequency; selecting one of the pre-stored therapy regimens; and stimulating the human subject's brain or nervous system, in response to the selected pre-stored therapy regimen, by repetitively emitting electromagnetic pulses from the neurological stimulation device according to the set of stimulation parameters associated with the selected pre-stored therapy regimen, the electromagnetic pulses arranged in a plurality of bursts each comprising at least two electromagnetic pulses spaced according to said pulse frequency, and the bursts being spaced according to said burst repetition frequency.

The method may further include displaying stimulation parameters of the pre-stored therapy regimens on a graphic display in response to a user request, and receiving a user input to select one of the pre-stored therapy regimens. The user input may be manually entered via a keyboard, mouse, touchscreen, or control panel. The method may further include overriding, in response to a further user input, one or more stimulation parameters of the selected pre-stored therapy regimen, or bypassing the pre-stored therapy regimens in favor of user-entered stimulation parameters. The method may further include, in response to the user selection of one of the pre-stored therapy regimens, loading the stimulation parameters from the selected pre-stored therapy regimen into one or more counters and timers, and repetitively generating and emitting the electromagnetic pulses in a plurality of bursts to stimulate the patient's brain or nervous system according to the loaded stimulation parameters. The method may further comprise saving and storing a new set of stimulation parameters in association with a new therapy regimen in response to a user command, and thereafter making available the new therapy regimen for retrieval and use as one of the pre-stored therapy regimens. The new set of stimulation parameters may be obtained from values entered via the user input. The method may further comprise executing an automated search routine by systematically configuring and operating the neurological stimulation device with at least two different sets of stimulation parameters run at different times, and using results of the automated search routine for the new set of stimulation parameters. Executing the automated search routine may involve repetitively emitting electromagnetic pulses according to the at least two different sets of stimulation parameters using the neurological stimulation device, and the method may include measuring the human subject's response to the delivery of electromagnetic pulses according to the at least two different sets of stimulation parameters using, for example, an EEG sensor, an EMG sensor, an infrared sensor, or an optical activity sensor. Measuring the human subject's response may comprise measuring changes in the human subject's motor evoked potential (MEP). The neurological stimulation device may comprise a transcranial magnetic stimulation (TMS) device configured to non-invasively stimulate the human subject's brain by repetitively emitting the electronic pulses in the form of a transient electromagnetic field generated from one or more energized coils. The method may further include storing one or more of the pre-stored therapy regimens in association with information identifying a respective associated individual human subject, the one or more pre-stored therapy regimens being customized for the respective associated individual human subject, and may include storing one or more of the pre-stored therapy regimens in association with information identifying a type of physiological, neurological or other condition to be treated using the stimulating pulses associated with the pre-stored therapy regimen. The neurological stimulation device may be selected from the group of: a vagus nerve stimulation device, a peripheral nerve stimulation device, a deep brain stimulation device, a peripheral nerve field stimulation device, a cortical stimulation device, a transcutaneous vagal nerve stimulation device, a transcutaneous electrical nerve stimulation device, an electroconvulsive therapy device, or a transcranial direct current stimulation device, a transcranial alternating current device, a transcranial random noise device, a trigeminal nerve stimulation device, a multi-coil transcranial magnetic stimulation device, a paired associative stimulation device, or a combination of the aforementioned devices.

At least one of said pre-stored therapy regimens may comprise either (i) a set of stimulation parameters defining a pulse frequency in a range from 19 to 21 Hertz and a number of pulses per burst equal to three, or (ii) a set of stimulation parameters defining a pulse frequency in a range from 22 to 26 Hertz and a number of pulses per burst equal to two. The set of stored stimulation parameters for one or more of the pre-stored therapy regimens may further comprise a number of pulses per burst parameter, a number of bursts per train parameter, and a train length parameter, wherein each train comprises the same number of plurality of bursts. The set of stored stimulation parameters for at least one of the pre-stored therapy regimens may be selected so as to induce an inhibitory neural response in the human subject, to induce an excitatory neural response in the human subject, or to augment the response to another central or peripheral nervous system treatment.

In another aspect of the embodiments disclosed herein, a therapeutic device for delivering artificial stimulating pulses to a human subject is provided, comprising a set of stored stimulation parameters determining a burst stimulation sequence, the set of stored stimulation parameters defining at least a pulse frequency, a burst repetition frequency, and a total number of pulses set to a value of 100 or less for the burst stimulation sequence; and a neurological stimulation device configured to stimulate the human subject's brain or nervous system by repetitively emitting electromagnetic pulses according to the set of stored stimulation parameters, the electromagnetic pulses equaling the value of the total number of pulses and arranged in a plurality of bursts each comprising electromagnetic pulses spaced according to the pulse frequency, the bursts being spaced according to the burst repetition frequency.

In some embodiments, the burst repetition frequency may be selected in a range from 3 to 8 Hertz, and the pulse frequency may be selected in a range of 12 to 40 Hertz. In other embodiments, the burst repetition frequency may be selected in a range from 4 to 7 Hertz, and the pulse frequency selected in a range from 16 to 28 Hertz. The total number of pulses may be set to a value in a range from 3 to 39. The burst repetition frequency may be selected in a range from 3 to 8 Hertz, and the pulse frequency selected in a range of 12 to 40 Hertz. The burst repetition frequency may be selected in a range from 4 to 7 Hertz, and the pulse frequency selected in a range from 16 to 28 Hertz. The number of electromagnetic pulses per burst is three. The burst repetition frequency may be selected in a range from 5 to 6 Hertz, and the pulse frequency selected in a range from 19 to 21 Hertz. The number of electromagnetic pulses per burst may be two. The burst repetition frequency may be selected in a range from 5 to 6 Hertz, and the pulse frequency selected in a range from 22 to 26 Hertz. The burst repetition frequency and the pulse frequency may be selected so that the ratio of the pulse frequency to the burst repetition frequency is in the range from 3 to 5, and the number of electromagnetic pulses per burst may be three; in such as case, the number of bursts may be between one and thirteen and, more preferably, may be between four and ten. The number of electromagnetic pulses per burst may be two; in such as case, the number of bursts may be between one and thirteen and, more preferably, may be between four and ten. The bursts may be arranged in a plurality of trains, each train comprising a plurality of said bursts and being separated by an inter-train interval during which no electromagnetic pulses are delivered. One or more trains each train may have the same number of bursts, wherein the inter-train interval is longer than the duration of each train.

The neurological stimulation device may comprise a transcranial magnetic stimulation (TMS) device configured to non-invasively stimulate the human subject's brain or nervous system by repetitively emitting the electronic pulses in the form of a transient electromagnetic field generated from one or more energized coils. The neurological stimulation device may be selected from the group of: a vagus nerve stimulation device, a peripheral nerve stimulation device, a deep brain stimulation device, a peripheral nerve field stimulation device, a cortical stimulation device, a transcutaneous vagal nerve stimulation device, a transcutaneous electrical nerve stimulation device, an electroconvulsive therapy device, or a transcranial direct current stimulation device a transcranial alternating current device, a transcranial random noise device, a trigeminal nerve stimulation device, a multi-coil transcranial magnetic stimulation device, a paired associative stimulation device, or a combination of the aforementioned devices.

The set of stored stimulation parameters may be entered via a user interface and temporarily stored during a treatment session involving delivery of the electromagnetic pulses to the human subject, and thereafter discarded. The set of stored stimulation parameters including the number of pulses may be selected so as to induce an inhibitory neural response in the human subject, to induce an excitatory neural response in the human subject, or to augment the response to another central or peripheral nervous system treatment.

In another aspect of the embodiments disclosed herein, a therapeutic or diagnostic system is provided, comprising a set of stored stimulation parameters determining a burst stimulation sequence, the set of stored stimulation parameters defining at least a pulse frequency, a burst repetition frequency, and a total number of pulses set to a value of 100 or less for the burst stimulation sequence; a pulse command generator responsive to the set of stored stimulation parameters, configured to output pulse commands equal to the total number of pulses with a pattern based upon the set of stored stimulation parameters including the pulse frequency and the burst repetition frequency; and a non-invasive brain stimulation device responsive to the pulse commands, configured to stimulate the human subject's brain by repetitively emitting electromagnetic pulses according to the pattern of pulse commands, the electromagnetic pulses arranged in a plurality of bursts each comprising at least two electromagnetic pulses spaced according to the pulse frequency, the bursts being spaced apart according to the burst repetition frequency.

The burst repetition frequency may be selected in a range from 3 to 8 Hertz, and the pulse frequency selected in a range of 12 to 40 Hertz; more preferably, the burst repetition frequency may be selected in a range from 4 to 7 Hertz, and the pulse frequency selected in a range from 16 to 28 Hertz. The total number of pulses may be set to a value in a range from 3 to 39. The number of electromagnetic pulses per burst may three, wherein the burst repetition frequency is selected in a range from 5 to 6 Hertz, and the pulse frequency is selected in a range from 19 to 21 Hertz. The number of electromagnetic pulses per burst is two, wherein the burst repetition frequency is selected in a range from 5 to 6 Hertz, and the pulse frequency is selected in a range from 22 to 26 Hertz. The burst repetition frequency and the pulse frequency may be selected so that the ratio of the pulse frequency to the burst repetition frequency is in the range from 3 to 5, and the number of electromagnetic pulses per burst may be three. The number of bursts may be between one and thirteen and, more preferably, between four and ten. The number of electromagnetic pulses per burst may be two, wherein the number of bursts is between one and thirteen and, more preferably, between four and ten. The bursts may be arranged in a plurality of trains, each train comprising a plurality of said bursts and being separated by an inter-train interval during which no electromagnetic pulses are delivered.

The neurological stimulation device may comprise a transcranial magnetic stimulation (TMS) device configured to non-invasively stimulate the human subject's brain by repetitively emitting the electronic pulses in the form of a transient electromagnetic field generated from one or more energized coils. The set of stored stimulation parameters including the number of pulses may be selected so as to induce an inhibitory neural response in the human subject, to induce an excitatory neural response in the human subject, or to augment the response to another central or peripheral nervous system treatment. The therapeutic or diagnostic system may further comprise a measuring device to detect the human subject's response to the electromagnetic pulses and, more specifically, may comprise a device to measure the human subject's motor evoked potential.

In another aspect of the embodiments disclosed herein, a method for delivering artificial stimulating pulses to a human subject using a therapeutic or diagnostic neurological stimulation device is provided, comprising setting a pulse frequency parameter; setting a burst repetition frequency parameter; setting a total number of pulses for a pulse sequence to be delivered, the total number of pulses being less than 100; and stimulating the human subject's brain or nervous system by repetitively emitting a total number of electromagnetic pulses from the neurological stimulation device equal to the selected total number of pulses, in a pattern with the electromagnetic pulses arranged in a plurality of bursts each comprising at least two electromagnetic pulses spaced according to said pulse frequency, and the bursts being spaced according to said burst repetition frequency.

The burst repetition frequency of the method may be selected in a range from 3 to 8 Hertz, and the pulse frequency may be selected in a range of 12 to 40 Hertz; more preferably, the burst repetition frequency may be selected in a range from 4 to 7 Hertz, and the pulse frequency may be selected in a range from 16 to 28 Hertz. The total number of pulses may be set to a value in a range from 3 to 39, wherein the burst repetition frequency is selected in a range from 3 to 8 Hertz, and the pulse frequency is selected in a range of 12 to 40 Hertz, and more preferably, the burst repetition frequency is selected in a range from 4 to 7 Hertz, and the pulse frequency is selected in a range from 16 to 28 Hertz. The number of electromagnetic pulses per burst may be three; the burst repetition frequency may be selected in a range from 5 to 6 Hertz, and the pulse frequency selected in a range from 19 to 21 Hertz. The number of electromagnetic pulses per burst may be two; the burst repetition frequency may be selected in a range from 5 to 6 Hertz, and the pulse frequency selected in a range from 22 to 26 Hertz. The burst repetition frequency and the pulse frequency may be selected so that the ratio of the pulse frequency to the burst repetition frequency is in the range from 3 to 5; and the number of electromagnetic pulses per burst may be three. The number of bursts may be between two and thirteen and, more preferably, between four and ten. The number of electromagnetic pulses per burst may be two. The number of bursts may be between one and thirteen and, more preferably, between four and ten. The bursts may be arranged in a plurality of trains, each train comprising a plurality of said bursts and being separated by an inter-train interval during which no electromagnetic pulses are delivered.

The neurological stimulation device may comprise a transcranial magnetic stimulation (TMS) device configured to non-invasively stimulate the human subject's brain by repetitively emitting the electronic pulses in the form of a transient electromagnetic field generated from one or more energized coils. The neurological stimulation device may also be selected from the group of: a vagus nerve stimulation device, a peripheral nerve stimulation device, a deep brain stimulation device, a peripheral nerve field stimulation device, a cortical stimulation device, a transcutaneous vagal nerve stimulation device, a transcutaneous electrical nerve stimulation device, an electroconvulsive therapy device, a transcranial direct current stimulation device, a transcranial alternating current device, a transcranial random noise device, a trigeminal nerve stimulation device, a multi-coil transcranial magnetic stimulation device, a paired associative stimulation device, or a combination of the aforementioned devices. The pattern and total number of electromagnetic pulses may be selected so as to induce an inhibitory neural response in the human subject, to induce an excitatory neural response in the human subject, to increase the neuroplasticity in a region of the human subject's brain, or to augment the response to another central or peripheral nervous system treatment. The electromagnetic pulses may be applied to the left dorsolateral prefrontal cortex, right dorsolateral prefrontal cortex, or cingulate cortex of the human subject's brain.

While certain embodiments have been described, the embodiments have been presented by way of example only and are not intended to limit the scope of the inventions. Indeed, the novel devices and methods described herein may be embodied in a variety of other forms; furthermore, various omissions, substitutions, and changes in the form of the devices and methods described herein may be made without departing from the spirit of the inventions. For example, techniques, systems, subsystems, and methods described and illustrated in the various embodiments as discrete or separate may be combined or integrated with other systems, modules, techniques, or methods without departing from the scope of and the present disclosure. Other items shown or discussed as coupled or directly coupled or communicating with each other may be indirectly coupled or communicating through some interface, device, or intermediate component whether electrically, mechanically, or otherwise. The accompanying claims and their equivalents are intended to cover such forms or modifications as would fall within the scope and spirit of the invention(s). Indeed, none of the description in the present application should be read as implying that any particular element, step, or function is an essential element that must be included in the claim scope. In contrast, the scope of the patented subject matter is defined only by the allowed claims. Moreover, none of the claims is intended to invoke paragraph six of 35 U.S.C. section 112 unless the exact words "means for" are followed by a participle. The claims as filed as intended to cover the widest scope possible, and no subject matter is intentionally relinquished, dedicated, or abandoned.

While preferred embodiments of the invention have been described herein, many variations are possible which remain within the concept and scope of the invention. Such variations would become clear to one of ordinary skill in the art after inspection of the specification and the drawings. The invention therefore is not to be restricted except within the spirit and scope of any appended claims.

What is claimed is:

1. A therapeutic device for delivering artificial stimulating pulses to a human subject, comprising:
    a set of stored stimulation parameters determining a theta burst stimulation sequence, the set of stored stimulation parameters including at least a pulse frequency parameter having a pulse value selected in a range from 19 to 21 Hertz and a burst repetition frequency parameter having a repetition value that is in a range of 5 to 6 Hertz; and
    a neurological stimulation device configured to stimulate the human subject's brain or nervous system by repetitively emitting a series of bursts that each include at least two electromagnetic pulses, a frequency of the pulses within each burst being spaced according to the pulse value, the pulse value being the same for each burst, the first pulse of each burst being spaced from the first pulse of an adjacent burst according to the repetition value.

2. The therapeutic device of claim 1, wherein the bursts are arranged in a plurality of trains, each train comprising a plurality of said bursts and being separated by an inter-train interval during which no electromagnetic pulses are delivered.

3. The therapeutic device of claim 2, wherein each train has the same number of bursts, and wherein the inter-train interval is longer than the duration of each train.

4. The therapeutic device of claim 1, wherein the neurological stimulation device comprises a transcranial magnetic stimulation (TMS) device configured to non-invasively stimulate the human subject's central or peripheral nervous system by repetitively emitting the electronic pulses in the form of a transient electromagnetic field generated from one or more energized coils.

5. The therapeutic device of claim 1, wherein the neurological stimulation device comprises a device selected from the group consisting of: a vagus nerve stimulation device, a peripheral nerve stimulation device, a deep brain stimulation device, a peripheral nerve field stimulation device, a cortical stimulation device, a transcutaneous vagal nerve stimulation device, a transcutaneous electrical nerve stimulation device, an electroconvulsive therapy device, a transcranial direct current stimulation device, a transcranial alternating current device, a transcranial random noise device, a trigeminal nerve stimulation device, or a paired associative stimulation device.

6. The therapeutic device of claim 1, wherein the set of stored stimulation parameters further comprises a number of pulses per burst parameter, a number of bursts per train parameter, and one or more train length parameters, wherein each train comprises the same number of plurality of bursts.

7. The therapeutic device of claim 1, wherein the set of stored stimulation parameters are entered via a user interface and are temporarily stored during a treatment session involving delivery of the electromagnetic pulses to the human subject, and are thereafter discarded.

8. The therapeutic device of claim 1, wherein the set of stored stimulation parameters induce an inhibitory neural response in the human subject.

9. The therapeutic device of claim 1, wherein the set of stored stimulation parameters induce an excitatory neural response in the human subject.

10. The therapeutic device of claim 1, wherein the set of stored stimulation parameters augment the response to another central or peripheral nervous system treatment.

11. The therapeutic device of claim 1, wherein the neurological stimulation device comprises:
   a pulse command generator responsive to the stimulation parameters for generating pulse commands according to the pulse frequency parameter and the burst repetition frequency parameter; and
   a pulse delivery mechanism responsive to the pulse commands generated by the pulse command generator, for generating a central or peripheral nerve stimulating pulse corresponding to each pulse command.

12. The therapeutic device of claim 1, wherein the pulse frequency parameter is stored as a time duration corresponding to the frequency represented by the pulse frequency parameter, and wherein the burst repetition frequency parameter is stored as a time duration corresponding to the frequency represented by the burst repetition frequency parameter.

13. A method for delivering artificial stimulating pulses to a human subject, comprising: stimulating the human subject's brain or nervous system with a non-invasive neurological stimulation device that repetitively emits a series of bursts that each include at least two electromagnetic pulses, a frequency of the pulses within each burst being spaced according to a pulse value of a pulse frequency parameter in a range from 19-21 Hertz, the pulse value being the same for each burst, the first pulse of each burst being spaced from the first pulse of an adjacent burst according to a repetition value of a burst repetition frequency parameter that is in a range of 5 to 6 Hertz.

14. The method of claim 13, wherein the step of stimulating induces an inhibitory neural response in the human subject.

15. The method of claim 13, wherein the step of stimulating induces an excitatory neural response in the human subject.

16. The method of claim 13, wherein the step of stimulating augments the response to another central or peripheral nervous system treatment.

* * * * *